(12) United States Patent
Saze et al.

(10) Patent No.: US 8,476,582 B2
(45) Date of Patent: Jul. 2, 2013

(54) DEVICE FOR MEASURING RADIATION INTENSITY OF SMALL SEALED RADIOACTIVE SOURCE FOR CANCER THERAPY

(75) Inventors: Takuya Saze, Tokushima (JP); Shintaro Nakayama, Tokushima (JP); Shunsuke Furutani, Tokushima (JP); Yoshinori Kuwahara, Tokushima (JP); Tsutomu Morimoto, Tokushima (JP); Yusuke Kinoshita, Tokushima (JP); Yutaka Kurosaki, Takasago (JP); Takaharu Yamada, Anan (JP); Toshinori Shinohara, Anan (JP)

(73) Assignee: The University of Tokushima, Tokushima (JP)

( * ) Notice: Subject to any disclaimer, the term of this patent is extended or adjusted under 35 U.S.C. 154(b) by 0 days.

(21) Appl. No.: 13/513,419

(22) PCT Filed: Nov. 30, 2010

(86) PCT No.: PCT/JP2010/006990
§ 371 (c)(1),
(2), (4) Date: Aug. 13, 2012

(87) PCT Pub. No.: WO2011/067925
PCT Pub. Date: Jun. 9, 2011

(65) Prior Publication Data
US 2012/0326035 A1 Dec. 27, 2012

(30) Foreign Application Priority Data

Dec. 1, 2009 (JP) .................................. 2009-273344
Jun. 1, 2010 (JP) .................................. 2010-126136

(51) Int. Cl.
*G01T 1/16* (2006.01)

(52) U.S. Cl.
USPC ..................................... 250/252.1; 250/336.1

(58) Field of Classification Search
USPC .......................................... 250/252.1, 336.1
See application file for complete search history.

(56) References Cited

FOREIGN PATENT DOCUMENTS

| EP | 1 529 553 | 5/2005 |
| GB | 1 211 316 | 11/1970 |
| JP | 2006-263353 | 10/2006 |
| JP | 3132529 | 5/2007 |

OTHER PUBLICATIONS

Extended European Search Report for European Application 10 83 4379 (Apr. 8, 2013).

*Primary Examiner* — Mark R Gaworecki
(74) *Attorney, Agent, or Firm* — Edwards Wildman Palmer LLP; David G. Conlin; Steven M. Jensen

(57) ABSTRACT

A radiation intensity measuring apparatus is provided for an encapsulated sealed radioactive source for brachytherapy, which is capable of measuring radiation intensity of sources with a cartridge enclosed under sterile conditions. The radiation intensity measuring apparatus includes a radiation intensity measuring device for measuring radiation emitted from a source, a holding device for holding a cartridge, and a moving mechanism for moving the holding device to the radiation intensity measuring device. The moving device includes a guide portion for guiding the movement of the holding device so that the holding device moves along a direction perpendicular to an axial direction of a slit, and a moving portion for moving the holding device so that all the sources loaded in the cartridge pass through a position of the slit in a housing space of a housing portion.

30 Claims, 21 Drawing Sheets

F I G. 3
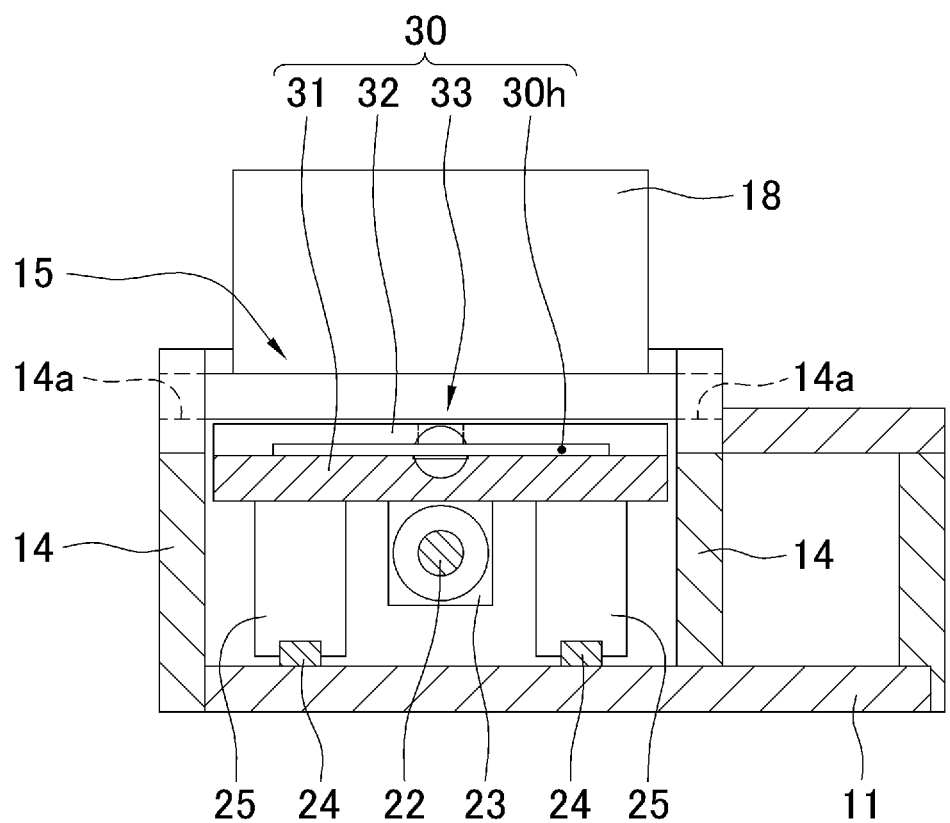

(A)

(B)

(A)

(B)

(A)

(B)

(A)  (B)

(A)

(B)

(C)

(A)

(B)

(C)

F I G. 2 1
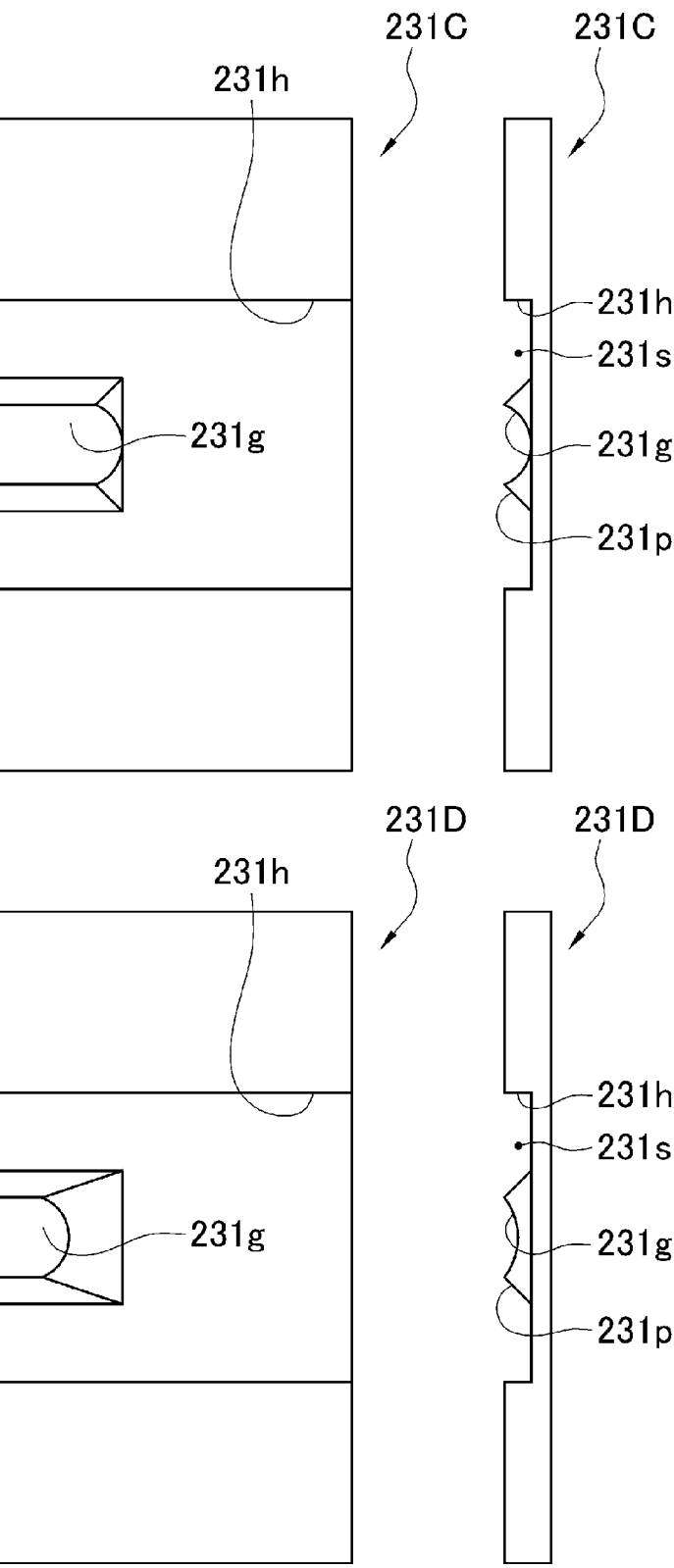

DEVICE FOR MEASURING RADIATION INTENSITY OF SMALL SEALED RADIOACTIVE SOURCE FOR CANCER THERAPY

TECHNICAL FIELD

The present invention relates to a radiation intensity measuring apparatus for an encapsulated sealed radioactive source for brachytherapy and, more particularly, to a radiation intensity measuring apparatus for an encapsulated sealed radioactive source for brachytherapy adapted to measure radiation intensity of an encapsulated sealed radioactive source used for brachytherapy for prostate cancer.

BACKGROUND ART

Brachytherapy for prostate cancer is mainly performed by inserting a source obtained by tightly enclosing iodine-125 of a radioactive substance in a capsule made of titanium (hereinafter, simply referred to as a source) into a prostate. A cartridge loaded with 5 or 15 of such sources is usually provided and such cartridge C is provided to be tightly enclosed in a bag under sterile conditions. Sources S are loaded in the cartridge C with their axial directions aligned (the axial directions are parallel to each other) (FIG. 15(A)).

In the brachytherapy, the number of sources inserted into a prostate and insertion positions thereof are determined depending on a state of prostate cancer of each person on the precondition that amounts of radioactivity of a radioactive substance tightly enclosed in the respective sources are the same. The number of sources to be inserted is approximately 70 to 100 for one brachytherapy.

It is, however, said that there are defective sources having an amount of radioactivity different from a nominal value suggested by a supplier of cartridges among a plurality of sources on the order of one out of several hundreds or on the order of two out of one hundred in the case of poor-quality sources. For example, a source having almost no radioactivity or a source having a larger amount of radioactivity than the nominal value may be included. When such a defective source is used, problems occur such that a desired therapeutic effect cannot be achieved due to a shortage of an exposure dose, or conversely, other tissues are affected due to an excessive exposure dose, or the like. The American Association of Physicists in Medicine (AAPM) therefore recommends that at least 10% of sources to be used or all the sources, if possible, are measured at each of the facilities.

Properly speaking, radiation intensity of all sources should be measured at respective facilities where sources are used. However, amounts of radioactivity in capsules have to be measured one by one according to generally employed radiation intensity measuring methods using an ionization chamber (radiation measuring apparatus). This brings the following disadvantages (1) to (7), and in fact, it is very difficult to measure radiation intensity of all sources at each of the facilities.
(1) A wrapped cartridge under sterile conditions needs to be taken out of a bag.
(2) Sources need to be taken out of the cartridge.
(3) The sources are measured one by one, thereby requiring a large amount of time.
(4) The sources taken out of the cartridge need to be loaded in the cartridge again.
(5) The cartridge again loaded with the sources needs to be sterilized again.
(6) It is difficult for hands and fingers of a worker to be prevented from being exposed to radiation during the operation of (1) to (5).
(7) A calibrated ionization chamber for exclusive use is required.

In order to solve the above problems, a measuring apparatus for measuring radiation intensity of each source with sources loaded in a cartridge has been developed (Patent Literature 1).

Patent Literature 1 discloses a technique related to a measuring apparatus for measuring radiation intensity of sources. The measuring apparatus includes a reception portion for receiving a cartridge loaded with encapsulated sealed radioactive sources inside thereof, and further, is provided with an insertion opening through which the cartridge is inserted into the reception portion from the outside and a plurality of apertures extending through between the reception portion and the outside.

According to the configuration, the cartridge is inserted into the reception portion of the measuring apparatus from the insertion opening, and the measuring apparatus is provided on X-ray film so that the plurality of apertures come into contact with the X-ray film. Then, radiations emitted from the respective sources leak outside the measuring apparatus via corresponding apertures. The X-ray film in contact with the measuring apparatus is then exposed to the radiations, and therefore, information about radiation intensity of each source is recorded on the film. Consequently, desired information can be obtained by analyzing the record on the film.

The measuring apparatus in Patent Literature 1 measures the sources loaded in the cartridge as they are and thereby the above problems (2) to (4) may be solved. However, the cartridge wrapped under sterile conditions cannot be measured without being taken out of a bag, leading to failure in solving the above problems (1) and (5).

Moreover, there is a high possibility that the worker is exposed to radiation because the operation is performed by taking the cartridge out of the bag, also leading to failure in solving the above problem (6).

Although the measuring apparatus in Patent Literature 1 can solve the problems (2) to (4), measuring accuracy of radiation intensity disadvantageously decreases.

In the case of the measuring apparatus in Patent Literature 1, the measuring apparatus is for exposing the X-ray film to radiations leaking from a plurality of apertures h. In order to obtain information of radiation intensity of each source S, central axes of the plurality of the sources S and central axes of the plurality of the apertures h have to be all aligned correctly so that each of the apertures h corresponds to one source (FIG. 15(B)).

However, not all the sources S loaded in the cartridge C are loaded at the same intervals and thereby there is a slight difference in placement of the sources S among respective cartridges C. Thus, when the plurality of apertures h are positioned at regular intervals according to an average diameter (0.8 mm) of the sources S, the central axes of the sources S and the central axes of the apertures h may be deviated from each other. This happens in the case where the loading intervals are different from the average diameter such as the case where sources S not having the average diameter are loaded. As a result, the radiation intensity of each of the sources S cannot be measured correctly (FIG. 15 (C)).

As described above, the measuring apparatus in Patent Literature 1 cannot solve the conventional problems (1) to (7), and therefore, a development of a measuring apparatus capable of solving the problems has been desired.

[Citation List]

[Patent Literature]

Patent Literature 1: Japanese Utility Model Registration No. 3132529

SUMMARY OF INVENTION

Technical Problem

In view of the above circumstances, an object of the present invention is to provide a radiation intensity measuring apparatus for an encapsulated sealed radioactive source for brachytherapy capable of easily and accurately measuring radiation intensity of a source with a cartridge wrapped under sterile conditions.

Solution to Problem

A radiation intensity measuring apparatus for an encapsulated sealed radioactive source for brachytherapy according to a first feature of the present invention is an apparatus adapted to measure radiation intensity of sources loaded in a cartridge, including: radiation intensity measuring means for measuring radiations emitted from the sources; holding means for holding the cartridge; and moving means for moving the holding means to the radiation intensity measuring means, wherein the radiation intensity measuring means includes: housing space in which the cartridge held by the holding means is brought; and an housing portion provided with a slit communicating between the housing space and an outside, the slit provided on the housing portion is formed so that a width thereof is narrower than a diameter of the sources, the holding means includes: a holding mechanism for holding the cartridge so that an axial direction of the sources loaded in the cartridge is parallel to an axial direction of the slit, and the moving means includes: a guide portion for guiding a movement of the holding means so that the holding means moves along a direction perpendicular to the axial direction of the slit; and a moving portion for moving the holding means so that the sources loaded in the cartridge pass through a position of the slit in the housing space of the housing portion.

A radiation intensity measuring apparatus for an encapsulated sealed radioactive source for brachytherapy according to a second feature of the present invention is the first feature of the present invention, wherein the cartridge includes: a substantially cylindrical magazine; and a seed cartridge provided on a tip of the magazine and having a plate shape with a thickness thinner than a diameter of the magazine, the seed cartridge can be loaded with the sources thereinside so that a surface of the seed cartridge is parallel to the axial direction of the sources, the holding means holds the cartridge tightly enclosed in a bag, the holding mechanism includes: a clearance extending along a moving direction of the holding means and having a height narrower than the thickness of the seed cartridge, the clearance is provided with a tip holding region of space communicating with one aperture of the clearance, a fixed groove obtained by recessing a surface having the clearance formed is formed in the tip holding region, and the fixed groove is formed so that a tip surface thereof is parallel to the axial direction of the slit and a distance from a bottom surface of the fixed groove to the other surface having the clearance formed is smaller than a thickness obtained by adding a thickness of the bag including the cartridge and the thickness of the seed cartridge to an extent that a tip portion of the seed cartridge can be inserted into the tip holding region.

A radiation intensity measuring apparatus for an encapsulated sealed radioactive source for brachytherapy according to a third feature of the present invention is the second feature of the present invention, wherein a coupling region of space coupling between an end of the one aperture and the tip holding region is formed at the clearance, and an inclined plane coupling between the bottom surface of the fixed groove and the end of the one aperture is formed in the coupling region.

A radiation intensity measuring apparatus for an encapsulated sealed radioactive source for brachytherapy according to a fourth feature of the present invention is the first, second or third feature of the present invention, further including supplying means for supplying the cartridge enclosed in the bag to the holding means, wherein the sources are loaded in the cartridge so that the axial direction is perpendicular to an axial direction of the magazine in the cartridge, the supplying means includes: a bag holding mechanism for holding the bag including the cartridge; a positioning mechanism provided between the bag holding mechanism and the holding mechanism, the positioning mechanism moving relatively close to and apart from the bag holding mechanism in a direction of a reference axis coaxial with a central axis of the magazine in the cartridge held by the holding means; and a cartridge supplying mechanism for supplying the cartridge positioned by a positioning portion of the positioning mechanism to the holding means, and the positioning mechanism includes: the positioning portion for positioning the cartridge so that the positioning portion approaches the cartridge enclosed in the bag held by the bag holding mechanism and the central axis of the magazine of the cartridge becomes coaxial with the reference axis.

A radiation intensity measuring apparatus for an encapsulated sealed radioactive source for brachytherapy according to a fifth feature of the present invention is the fourth feature of the present invention, wherein the bag holding mechanism includes: a pair of bag holding portions provided at positions sandwiching an perpendicular plane with respect to the axial direction of the slit, the pair of bag holding portions are provided so as to hold the bag in the vicinity of a central plane including the reference axis and perpendicular to the perpendicular plane, the positioning portion of the positioning mechanism includes: a pair of positioning members provided so as to sandwich the central plane, magazine housing space is formed between the pair of positioning members, the magazine housing space housing the magazine of the cartridge so as to be positioned when the positioning mechanism approaches the bag holding mechanism, the magazine housing space is formed so that a central axis thereof is coaxial with the reference axis, and opposite surfaces of the magazine housing space in the pair of positioning members are formed in a shape allowing a posture of the cartridge to change so that the central axis of the magazine in the cartridge becomes coaxial with the reference axis when the magazine of the cartridge is housed in the magazine housing space.

A radiation intensity measuring apparatus for an encapsulated sealed radioactive source for brachytherapy according to a sixth feature of the present invention is the fifth feature of the present invention, wherein one of the pair of positioning members includes: a pair of shaft-like members whose axial direction is parallel to the reference axis, the other positioning member includes: a supporting member provided so as to sandwich the central plane with the pair of shaft-like members and form the magazine housing space between the supporting member and the pair of shaft-like members, the positioning mechanism includes: a shaft-like member moving portion causing the pair of shaft-like members to move close to and apart from the bag holding mechanism along a direction of the reference axis, the pair of shaft-like members are provided so that a distance between the pair of the shaft-like members and/or a distance between the pair of the shaft-like members and the supporting member is shorter than a diameter of the magazine in the cartridge, and a distance from the reference axis becomes longer as getting close to a tip of a tip portion of each shaft-like member.

A radiation intensity measuring apparatus for an encapsulated sealed radioactive source for brachytherapy according to a seventh feature of the present invention is the fourth, fifth or sixth feature of the present invention, wherein the positioning mechanism includes: a position changing portion for changing a relative position between the positioning portion and the bag holding mechanism along a direction perpendicular to the perpendicular plane and parallel to the central plane.

A radiation intensity measuring apparatus for an encapsulated sealed radioactive source for brachytherapy according to a eighth feature of the present invention is the seventh feature of the present invention, wherein the position changing portion causes the bag holding mechanism to move back and forth.

A radiation intensity measuring apparatus for an encapsulated sealed radioactive source for brachytherapy according to a ninth feature of the present invention is the sixth, seventh or eighth feature of the present invention, wherein the supporting member includes: a pair of shaft-like portions parallel to the pair of shaft-like members and provided so as to form the magazine housing space between the pair of shaft-like members and the pair of shaft-like portions; the pair of shaft-like portions are provided so that a distance between the pair of shaft-like portions is shorter than the diameter of the magazine in the cartridge and a distance between one of the shaft-like members and one of the shaft-like portions located on a diagonal line in the magazine housing space is slightly longer than the diameter of the magazine in the cartridge.

A radiation intensity measuring apparatus for an encapsulated sealed radioactive source for brachytherapy according to a tenth feature of the present invention is any one of the fourth to ninth features of the present invention, wherein the positioning portion is provided on the holding means.

A radiation intensity measuring apparatus for an encapsulated sealed radioactive source for brachytherapy according to a eleventh feature of the present invention is the first or second feature of the present invention, wherein a width of the clearance is formed so as to be wider than a width of the bag, and the clearance includes: a magazine holding region provided between one aperture of the clearance and the tip holding region, the magazine holding region being space communicating with the tip holding region formed by recessing both surfaces of the clearance and substantially cylindrical space for housing the magazine.

A radiation intensity measuring apparatus for an encapsulated sealed radioactive source for brachytherapy according to a twelfth feature of the present invention is the eleventh feature of the present invention, wherein a coupling region of space coupling between the tip holding region and the magazine holding region is formed at the clearance, and an inclined plane coupling between the bottom surface of the fixed groove and a concave surface of the magazine holding region is formed in the coupling region.

A radiation intensity measuring apparatus for an encapsulated sealed radioactive source for brachytherapy according to a thirteenth feature of the present invention is any one of the first to twelfth features of the present invention, wherein the housing portion of the radiation intensity measuring means includes: a slit plate provided with a slit communicating between the magazine housing space and an outside and having a pair of slit forming plates, one end surface of each of the slit forming plates is provided with a reference surface, a slide surface parallel to the reference surface and offset with respect to the reference surface by a width of the slit, and a coupling surface for coupling the slide surface and the reference surface, and the slit plate is formed by coupling the reference surface of one of the pair of slit forming plates to the slide surface of the other slit forming plate so as to come into surface contact with each other.

A radiation intensity measuring apparatus for an encapsulated sealed radioactive source for brachytherapy according to a fourteenth feature of the present invention is any one of the first to twelfth features of the present invention, wherein the housing portion of the radiation intensity measuring means includes: a slit plate having the slit formed; and a body portion having the slit plate fixed thereto, the slit plate is formed by joining two plate-like members with end surfaces thereof coming into surface contact with each other, and a concave portion is provided on the end surface coming into surface contact with the other plate-like member of the plate-like members, the concave portion forming the slit obtained by recessing the end surface.

A radiation intensity measuring apparatus for an encapsulated sealed radioactive source for brachytherapy according to a fifteenth feature of the present invention is any one of the first to fourteenth features of the present invention, wherein the radiation intensity measuring means includes: a radiation-blocking member provided so as to surround a periphery of the slit, and the radiation-blocking member includes: a measuring apparatus housing portion having the measuring apparatus provided therein.

Advantageous Effects of Invention

According to the first feature of the present invention, when the moving means moves the holding mechanism holding the cartridge to the radiation intensity measuring means, variations in amount of radiations passing through the slit can be measured because the plurality of sources (for example, all sources) sequentially pass through a position of the slit. Radioactivity of each of the sources can be calculated based on the variations in amount of radiations. Accordingly, radiation intensity of each of the sources can be measured at one measurement with the plurality of sources loaded in the cartridge, thereby enabling to measure radioactivity of the plurality of sources for a short time. Moreover, a peak value of a variation curve of radiation intensity, or the presence or absence of the peak value can be grasped even if a slight deviation lies among loading intervals for the sources because the variations in amount of the radiations are measured with the sources being moved. Radiation intensity of each of the sources can therefore be correctly measured even if a slight deviation occurs among positions of the sources.

According to the second feature of the present invention, radiation intensity can be easily measured for further shorter time because radiation intensity of each of the sources can be measured with the cartridge in the bag under the sterile conditions. Additionally, simply by pressing the seed cartridge into the tip holding region, the seed cartridge can be fixed in the tip holding region. Further, simply by pressing the tip of the seed cartridge against the tip surface of the fixed groove in the tip holding region, the axial direction of the sources and the axial direction of the slit can be parallel to each other. The cartridge can therefore be easily fixed to the holding means for a short time so as to be in a correct position/posture even if a worker wears protective gloves.

According to the third feature of the present invention, the coupling region has the inclined plane. Therefore, by pressing the cartridge, the inclined plane allows the posture of the cartridge to be adjusted so that the axial direction of the sources and the axial direction of the slit are parallel to each other even if the seed cartridge is inclined at the time of inserting the cartridge. This enables to adjust the seed cartridge to be in the same posture every time.

According to the fourth feature of the present invention, when the bag holding mechanism holds the bag housing the cartridge, the positioning mechanism allows the cartridge to be positioned so that the central axis of the magazine is coaxial with the reference axis. When the cartridge supplying mechanism supplies the cartridge to the holding means with the cartridge being positioned, the holding means can hold the cartridge enclosed in the bag in a predetermined posture. That is, simply by causing the bag holding mechanism to hold the bag housing the cartridge, the holding means can hold the cartridge in the predetermined posture. When the moving means causes the holding mechanism holding the cartridge to move to the radiation intensity measuring means, variations in amount of radiations passing through the slit can be measured because the plurality of sources (for example, all sources) can sequentially pass through a position of the slit. That is, simply by causing the bag holding mechanism to hold the bag housing the cartridge, the holding means can hold the cartridge in the predetermined posture. Radiation intensity of the plurality of sources can therefore be measured substantially automatically with the cartridge enclosed in the bag.

According to the fifth feature of the present invention, when the cartridge is located in the magazine housing space, the cartridge can be easily positioned for a short time because the posture of the cartridge is changed so that the central axis of the magazine corresponds to the reference axis.

According to the sixth feature of the present invention, the pair of shaft-like members is provided so that a distance between the pair of the shaft-like members and/or a distance between the pair of the shaft-like members and the supporting member is shorter than the diameter of the magazine in the cartridge. Moreover, the distance between the pair of shaft-like members and the distance between the pair of shaft-like members and the supporting member become longer as getting close to the tip. Accordingly, the shaft-like member moving portion simply causes the pair of shaft-like members to approach the bag held by the bag holding mechanism, and thereby the cartridge enclosed in the bag can be positioned so that the axial direction of the magazine becomes coaxial with the reference axis. The positioning mechanism therefore has a simple structure achieving a simple structure of the apparatus, thereby making the apparatus compact.

According to the seventh feature of the present invention, when the position changing portion changes a relative position between the positioning portion and the bag holding mechanism in a direction of the central plane, the cartridge enclosed in the bag can be rotated around the central axis. The posture of the cartridge can therefore be adjusted to a predetermined posture allowing the holding means to hold the cartridge without a worker adjusting the posture of the cartridge even if the cartridge in the bag held by the bag holding mechanism has been in a rotated state from the predetermined posture in which the cartridge is held by the holding means. This enables to reduce a possibility of the worker being exposed to radiation because a period of time for which the worker is in contact with the cartridge in the bag can be shortened at the time of radiation intensity measurement of the sources.

According to the eighth feature of the present invention, the relative position between the positioning portion and the bag holding mechanism in the direction of the central plane is changed by moving the bag holding mechanism along the direction of the central plane. A mechanism for adjusting the cartridge posture can therefore have a simple structure.

According to the ninth feature of the present invention, the cartridge can be easily provided in the magazine housing space because the magazine housing space is formed with four shaft-like members.

According to the tenth feature of the present invention, the cartridge can be held by the holding means in a state of the cartridge being certainly positioned by the positioning means. This is because a relative position between the positioning portion and the holding means is fixed.

According to the eleventh feature of the present invention, radiation intensity can be easily measured for further shorter time because radiation intensity of each of the sources can be measured with the cartridge housed in the bag under the sterile conditions. Additionally, simply by pressing the seed cartridge into the tip holding region, the seed cartridge can be fixed in the tip holding region. Further, simply by pressing the tip of the seed cartridge against the tip surface of the fixed groove in the tip holding region, the axial direction of the sources and the axial direction of the slit can be parallel to each other. The cartridge can therefore be easily fixed to the holding means for a short time so as to be in a correct position/posture even if a worker wears protective gloves.

According to the twelfth feature of the present invention, the coupling region has the inclined plane. Therefore, by pressing the cartridge, the inclined plane allows the posture of the seed cartridge to be adjusted to the same posture every time so that the axial direction of the sources and the axial direction of the slit are parallel to each other even if the seed cartridge is inclined at the time of inserting the cartridge.

(Slit Plate)

According to the thirteenth feature of the present invention, coupling the pair of slit forming plates allows a slit to be formed between slide surfaces of the pair of slit forming plates. A length of the slit can be changed by changing a relative position between the reference surface of one slit forming plate and the slide surface of the other slit forming plate along the axial direction of the slit with the surfaces being in surface contact with each other. This allows the length of the slit to be adjusted according to the sources to be subjected to the radiation intensity measurement, allowing one slit plate to measure a plurality of sources. Another slit plate need not to be prepared according to sources to be measured, thereby reducing components of the apparatus and easily performing slit adjustment at the time of changing the sources.

According to the fourteenth feature of the present invention, when a concave portion is formed by cutting the end surface of the plate-like member, a slit can be formed by the concave portion by joining the end surface having the concave portion to the end surface of the other plate-like member. The slit can also be correctly and easily formed even if a width of the slit is very narrow because the width can be adjusted simply by adjusting a depth of the concave portion of the end surface.

(Radiation-Blocking Member)

According to the fifteenth feature of the present invention, it is possible to prevent scattered radiations of the sources or outside radiations from entering into a region where the measuring apparatus detects radiations passing through the slit. The radiations passing through the slit can therefore be accurately measured even if there is an agent, equipment and the like emitting radiations around the apparatus such as in a medical site.

BRIEF DESCRIPTION OF DRAWINGS

FIG. 3 is a cross sectional view taken along a line of FIG. 1.

FIG. 12 illustrates explanatory views when a cartridge C is rotated by moving a moving wall 150a.

FIG. 21(A) is a schematic view of another holding base 231C alone in the holding means 230, and FIG. 21(B) is a schematic view of another holding base 231D alone in the holding means 230.

DESCRIPTION OF EMBODIMENTS

Embodiments of the present invention will now be described with reference to the drawings.

A radiation intensity measuring apparatus for an encapsulated sealed radioactive source for brachytherapy according to the present invention is used for measuring an amount of radioactivity of a radioactive substance tightly enclosed in sources used for brachytherapy for prostate cancer, and is adapted to be able to measure intensity of radiations emitted from the sources loaded in the cartridge.

(Description of Source and Cartridge)

A source and a cartridge loaded with such sources will be simply described before describing a radiation intensity measuring apparatus for an encapsulated sealed radioactive source for brachytherapy (hereinafter, simply referred to as a radiation intensity measuring apparatus) according to the present invention.

A source S is obtained by tightly enclosing iodine-125 of a radioactive substance in a capsule made of titanium, whose length in an axial direction is longer than a diameter thereof. Each of the sources S generally used has a diameter of 0.80 to 0.95 mm and an axial length of 4.50 to 4.55 mm with slight variations.

Figure 15:
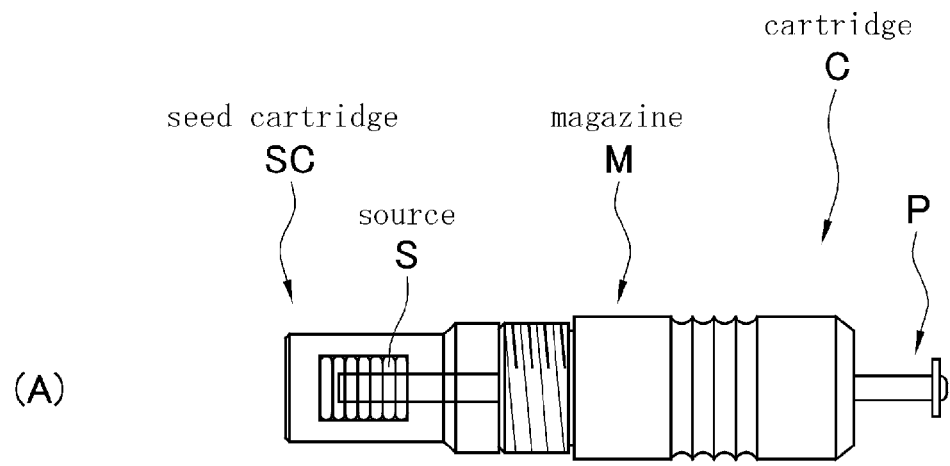
FIG. 15(A) is a schematic view of the cartridge C, and each
FIG. 15(B), 15(C) is schematic view of portions of slits h when the cartridge C is inserted into a measuring apparatus according to Patent Literature 1.
Figure 15:
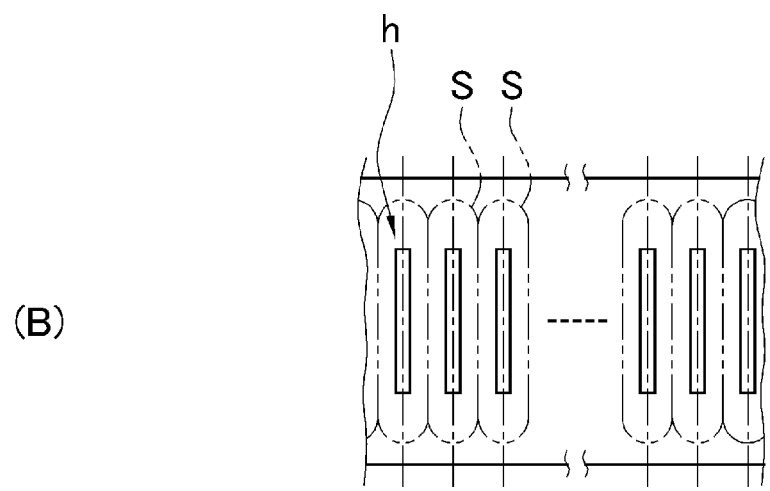
Figure 15:
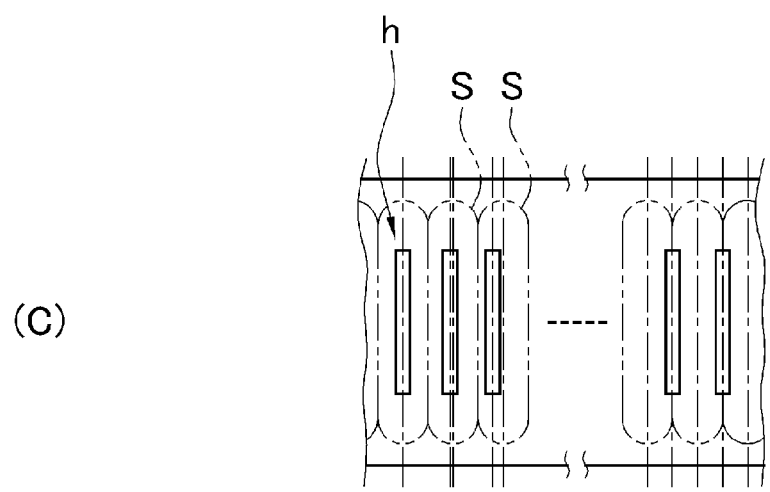

As illustrated in FIG. 15(A), a cartridge C is generally used for brachytherapy for prostate cancer. The cartridge C includes a substantially cylindrical magazine M, a seed cartridge SC provided at one axial end of the magazine M and loaded with a plurality of sources S, and a stick-like pusher P extending through a central axis of the magazine M. A tip of the pusher P reaches space loaded with the sources S in the seed cartridge SC, and has a function of holding the plurality of sources S in the seed cartridge SC so as to bring the sources S into intimate contact with each other.

The seed cartridge SC is provided so as to be located on the central axis of the magazine M. The seed cartridge SC is a plate-like member (a thickness thereof is approximately 3.1 mm) and is formed so that a tip surface thereof is formed into a flat surface perpendicular to the central axis of the magazine M and a surface thereof is parallel to the central axis of the magazine M. The seed cartridge SC has the space loaded with the sources S inside, as described above. The space is formed to have a height of a cross section thereof substantially the same as the diameter of the source S, as well as a width of the cross section substantially the same as a length of the source S. When the pusher P holds the plurality of sources S being in intimate contact with each other, an axial direction of the plurality of sources S becomes parallel to the tip surface and the surface of the seed cartridge SC.

Although the number of the sources S loaded in the space of the seed cartridge SC is not particularly limited, five or fifteen sources S are commonly loaded therein.

Additionally, the description refers to "substantially cylindrical magazine M", while a concept of the substantially cylindrical shape herein includes a shape used for magazines M of general cartridges C such as a hexagon or an octagon.

The cartridge C is provided to be tightly enclosed in a bag B under sterile conditions. The bag B includes a sheet made of paper (pasteboard) with its thickness of approximately 0.18 mm and a sheet made of synthetic resin (cover sheet) with its thickness of approximately 0.05 mm, and has a structure where peripheries of the both sheets are stuck together with the cartridge C sandwiched therebetween, followed by tightly enclosing.

(Description of Radiation Intensity Measuring Apparatus)

A radiation intensity measuring apparatus 1 in a first embodiment will now be described.

The radiation intensity measuring apparatus 1 according to the first embodiment is characterized by allowing an amount of radiations emitted from the sources S to be measured, even if the cartridge C loaded with the plurality of sources S is tightly enclosed in the bag B under sterile conditions.

Figure 1:
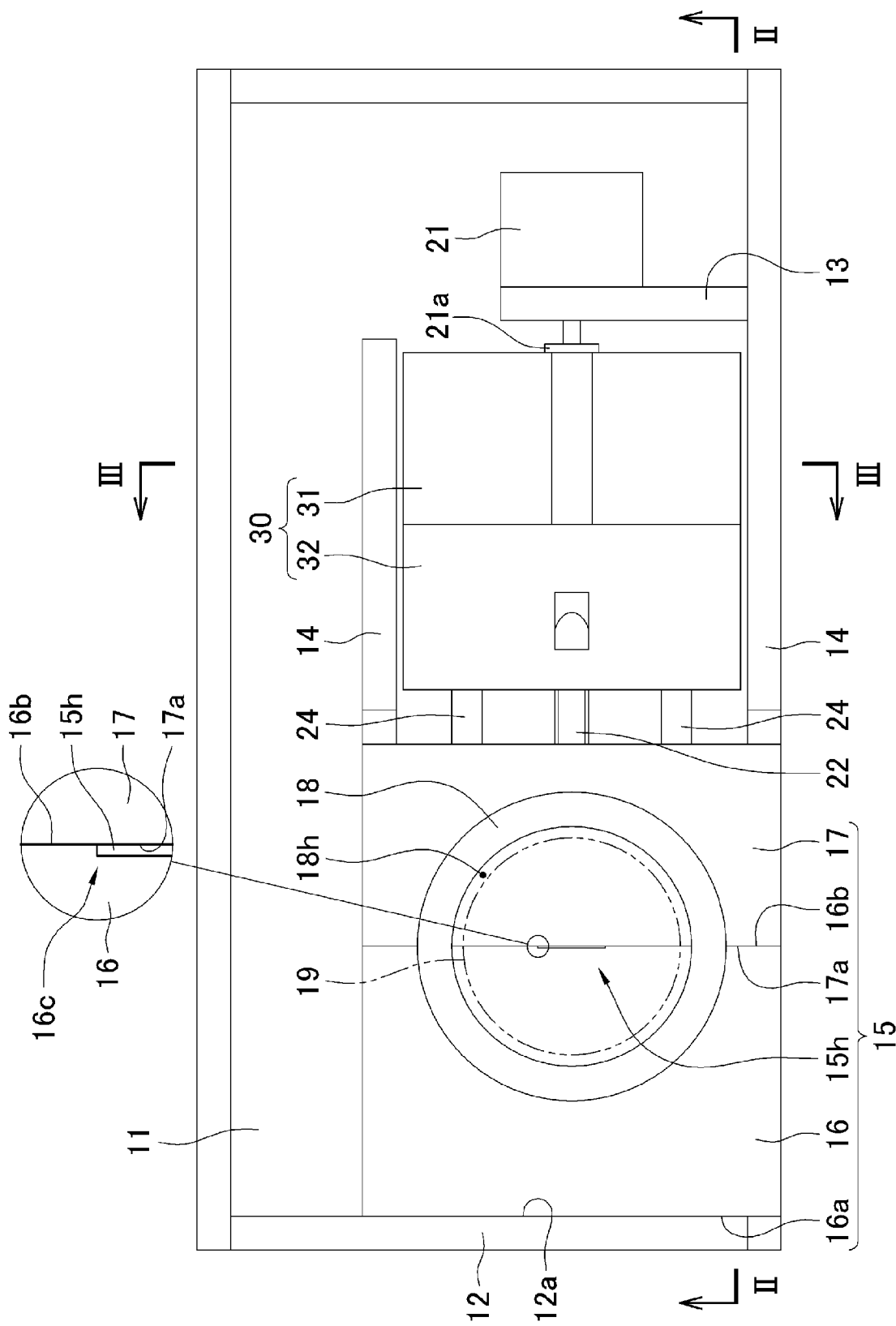
FIG. 1 is a schematic plan view illustrating a radiation intensity measuring apparatus 1 for an encapsulated sealed radioactive source for brachytherapy in a first embodiment.

In FIG. 1, reference numeral 11 indicates a base member of a base of the radiation intensity measuring apparatus 1. A top surface of the base member 11 is formed into a flat surface, on which a plurality of walls stand.

Specifically, a reference wall 12 stands on one end of the base member 11. The reference wall 12 has a reference inner surface 12a perpendicular to the top surface of the base member 11 and formed into a flat surface.

On the other hand, a driving means holding wall 13 stands at a position opposite to the reference inner surface 12a of the reference wall 12. The driving means holding wall 13 has an inner surface 13a parallel to the reference inner surface 12a.

A left-and-right pair of side walls 14, 14 stands between the reference wall 12 and the driving means holding wall 13. Each of the left-and-right pair of side walls 14, 14 has each of a pair of holding surfaces 14a, 14a in the vicinity of the reference wall 12 and parallel to the top surface of the base member 11, and the pair of holding surfaces 14a, 14a are located on the same plane (see FIG. 3).

Figure 2:
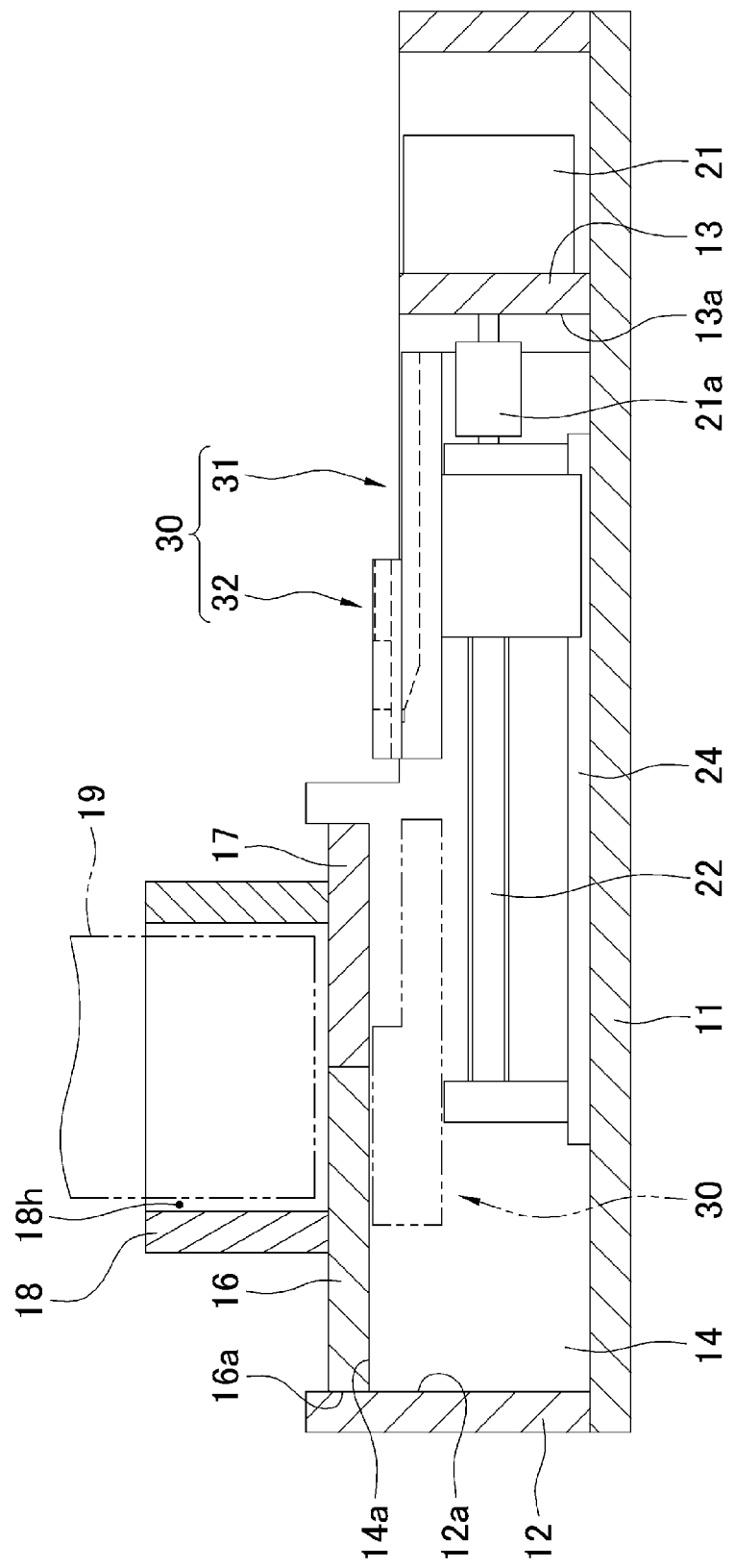
FIG. 2 is across sectional view taken along a II-II line of FIG. 1.

As illustrated in FIGS. 1 and 2, a slit plate 15 is provided on the pair of holding surfaces 14a, 14a of the left-and-right pair of side walls 14, 14. The slit plate 15 is a plate-like member having an under surface thereof formed into a flat surface, and a slit 15h of a through hole extending through vertically is formed almost in the center thereof.

The slit 15h is formed so that an axial direction thereof is parallel to the reference inner surface 12a of the reference wall 12, in other words, is perpendicular to a normal direction of the reference inner surface 12a of the reference wall 12. Further, the slit 15h is formed so as to have a width thereof being narrower than a diameter of the source S, and the reason will be described later.

The slit plate 15 may be formed to an extent that radiations from the source S do not pass through a part other than the slit 15h or do not affect the measurement of radiation intensity of the source S even if the radiations pass through. A material and a thickness thereof are not particularly limited.

A length of the slit 15h in the axial direction is not particularly limited, either. However, a length of 2 cm is preferable, considering a size with which scattered radiations are removed and radiations directly from the source S is obtained to the greatest extent possible.

As illustrated in FIG. 1, a cylindrical radiation-blocking member 18 with a hollow structure is provided on a top surface of the slit plate 15. The radiation-blocking member 18 is formed with a material such as brass, copper and tungsten, and is provided so as to locate the slit 15h in a hollow part inside thereof. The hollow part of the radiation-blocking member 18 is a measuring apparatus housing portion 18h, and is a part having a measuring apparatus 19 for measuring intensity of radiations emitted from the source S provided inside thereof.

As illustrated in FIG. 1, a motor 21 such as a stepping motor is mounted on the above driving means holding wall 13. The motor 21 is provided so that a main shaft thereof is perpendicular to the inner surface 13a, in other words, is parallel to the normal direction of the reference inner surface 12a of the reference wall 12. The main shaft of the motor 21 is coupled to a base end of a screw shaft 22 such as a ball screw shaft via a coupling 21a. The screw shaft 22 is also provided so that a central axis thereof is parallel to the normal direction of the reference inner surface 12a of the reference wall 12. In other words, the screw shaft 22 is provided so that the central axis is perpendicular to the slit 15h. A tip of the screw shaft 22 extends below the slit plate 15, that is, extends to space surrounded by the base member 11, the reference wall 12, the left-and-right pair of side walls 14, 14 and the slit plate 15.

As illustrated in FIG. 3, the screw shaft 22 is screwed with a nut member 23 to which holding means 30 provided above the screw shaft 22 is coupled. The holding means 30 can hold the cartridge C in a predetermined posture. Specifically, the holding means 30 has a function of holding the cartridge C so that an axial direction of the sources S loaded in the cartridge C is parallel to the axial direction of the slit 15h, and details thereof will be described later.

A pair of rails 24,24 parallel to the screw shaft 22 is provided on the top surface of the base member 11. A sliding member 25 such as a bearing truck is movably mounted on each of the rails 24,24 along an axial direction of the rail 24. The pair of sliding members 25,25 is coupled to the holding means 30.

According to the above configuration, rotation of the screw shaft 22 allows the holding means 30 together with the nut member 23 to move along the screw shaft 22 when the motor 21 is operated. In other words, the holding means 30 can be moved along the normal direction of the reference inner surface 12a of the reference wall 12. Moreover, since the holding means 30 moves in a state of being guided by the pair of rails 24,24 via the pair of sliding members 25,25, the holding means 30 can stably move.

The holding means 30 is provided so that a distance from the top surface of the base member 11 to a top end of the holding means 30 is shorter than a distance from the top surface of the base member 11 to the under surface of the slit plate 15 provided on the pair of holding surfaces 14a,14a of the left-and-right pair of side walls 14,14. The tip of the screw shaft 22 extends below the slit plate 15, thereby allowing the holding means 30 to move below the slit plate 15.

(Radiation Intensity Measurement by Radiation Intensity Measuring Apparatus 1 in First Embodiment)

With the above configuration, the radiation intensity measuring apparatus 1 in the first embodiment can measure radiation intensity of each of the sources S loaded in the cartridge C according to a method described below.

The measuring apparatus 19 is first provided in the measuring apparatus housing portion 18h of the radiation-blocking member 18 provided on a top surface of the slit plate 15. When the cartridge C with sources S having their radiation intensity to be measured is inserted into the holding means 30, preparation for the measurement is completed.

After the preparation for the measurement is completed, the motor 21 is operated, causing the holding means 30 to move below the slit plate 15. At this time, when the holding means 30 is moved so that the sources S held by the holding means 30 pass through a position of the slit 15h, the measuring apparatus 19 can measure intensity of radiations passing through the slit 15h.

Here, the holding means 30 holds the cartridge C so that the axial direction of the plurality of sources S loaded in the cartridge C is parallel to the axial direction of the slit 15h. The plurality of sources S therefore sequentially pass through the position of the slit 15h with the axial direction parallel to the axial direction of the slit 15h when the holding means 30 moves along the screw shaft 22. Since the width of the slit 15h is formed to be narrower than the diameter of the sources S, radiation intensity detected by the measuring apparatus 19 changes according to the movement of the plurality of sources S.

Specifically, since the width of the slit 15h is narrower than the diameter of the source S, only a part of radiations emitted from the source S pass through the slit 15h. Consequently, measuring apparatus 19 detects only the radiations passing through the slit 15h. The radiations emitted from the source S are radially emitted from a central axis of the source S, and therefore, radiation intensity detected by the measuring apparatus 19 reaches the maximum when the central axis of the slit 15h corresponds to the central axis of the source S. Conversely, the radiation intensity is more and more reduced as a deviation between the both central axes becomes larger. Accordingly, if the axial direction of the plurality of the sources S is maintained parallel to the axial direction of the slit 15h during the movement, the radiation intensity detected by the measuring apparatus 19 shows variations according to the movement of the plurality of sources S. That is, the radiation intensity reaches a peak at the timing when the central axis of each source S corresponds to the central axis of the slit 15h, whereas the radiation intensity becomes low between the central axes of the sources S adjacent to each other.

Accordingly, radioactivity of each of the sources S can be calculated based on the variations of the thus measured radiation intensity, namely the number of peaks of the radiation intensity, a peak value thereof, and timing of the peak.

The radiation intensity measuring apparatus 1 in the first embodiment causes the holding means 30 to hold the cartridge C loaded with the plurality of sources S and all of the sources S to move so as to pass through the position of the slit 15h. This allows radiation intensity of each of the sources S to be measured at one measurement with the plurality of sources S (namely, all of the sources S) loaded in the cartridge C. Radioactivity of the plurality of sources S loaded in the cartridge C can therefore be measured for a short time.

When only a part of the sources S out of the plurality of sources S loaded in the cartridge C is intended to be measured, not all of the sources S necessarily pass through the position of the slit 15h. The holding means 30 may be moved so that the sources S intended to be measured pass through the position of the slit 15h.

Moreover, since the variations of the radiation intensity are measured by moving the plurality of sources S loaded in the cartridge C, a peak value of a variation curve of the radiation intensity, or the presence or absence of the peak value can be grasped even if loading intervals for the sources S are slightly deviated from each other.

Radiation intensity of each of the sources S can therefore be measured correctly even if positions of the sources S loaded in the cartridge C are slightly deviated from each other.

A velocity of the movement of the holding means 30 is not particularly limited, and the velocity is acceptable as long as the variations of the radiation intensity appear to an extent that radioactivity of each of the sources S can be calculated.

In the case of grasping an absolute value of the radiation intensity of each source S, a variation curve of radiation intensity with respect to a cartridge C loaded with reference sources S having radiation intensity as a standard may be measured before measurement of a target cartridge C. Then, the absolute value of radiation intensity of each source S loaded in the target cartridge C can be grasped based on a measured value (peak value) of the target cartridge C with a peak value of the reference source as a standard.

Additionally, if the absolute value of the radiation intensity of each source S is not necessary, intercomparison of the peak values of respective sources S in the variation curve of the radiation intensity enables to grasp quality of each source S.

Although the case where the radiation intensity measuring apparatus 1 includes the radiation-blocking member has been described in the above example, the radiation-blocking member 18 is not necessarily provided.

However, the radiation-blocking member 18 can prevent scattered radiations of the target sources S or outside radiations from entering into a region where the measuring apparatus 19 detects radiations passing through the slit 15h. The radiations passing through the slit 15h can therefore be measured accurately even if there is an agent, equipment and the like emitting radiations around the radiation intensity measuring apparatus 1 such as in a medical site. This enables to accurately grasp the quality of each of the sources S.

The base member 11, the reference wall 12, the left-and-right pair of side walls 14,14 and the slit plate 15 correspond to an housing portion of radiation intensity measuring means according to claims. The base member 11, the reference wall 12 and the left-and-right pair of side walls 14,14 correspond to a body portion of the housing portion. Further, space surrounded by the base member 11, the reference wall 12, the left-and-right pair of side walls 14,14 and the slit plate 15 corresponds to housing space 10h.

The motor 21, the screw shaft 22, the nut member 23, the pair of rails 24,24 and the pair of sliding members 25,25 correspond to moving means according to claims, while the pair of rails 24,24 and the pair of sliding members 25,25 correspond to a guide portion according to claims. Hereinafter, the motor 21, the screw shaft 22, the nut member 23, the pair of rails 24,24, and the pair of sliding members 25,25 are all included in and referred to as moving means 20.

Note that the moving means and the guide portion are not limited to the above configuration. For example, a cylinder, an arm and the like can be used for the moving means, while a wire and the like can be used for the guide portion. However, stability of the movement of the holding means 30 can be enhanced when the holding means 30 is moved along the above screw shaft 22 and the pair of rails 24,24, that is, three linear members.

(Description of Holding Means 30)

The holding means 30 will now be described in detail.

As described above, the holding means 30 is for holding the cartridge C in a predetermined posture. The holding means 30 of the radiation intensity measuring apparatus 1 in the first embodiment has a structure allowing the cartridge C to be held in the predetermined posture even if the cartridge C is enclosed in the bag B.

Figure 4:
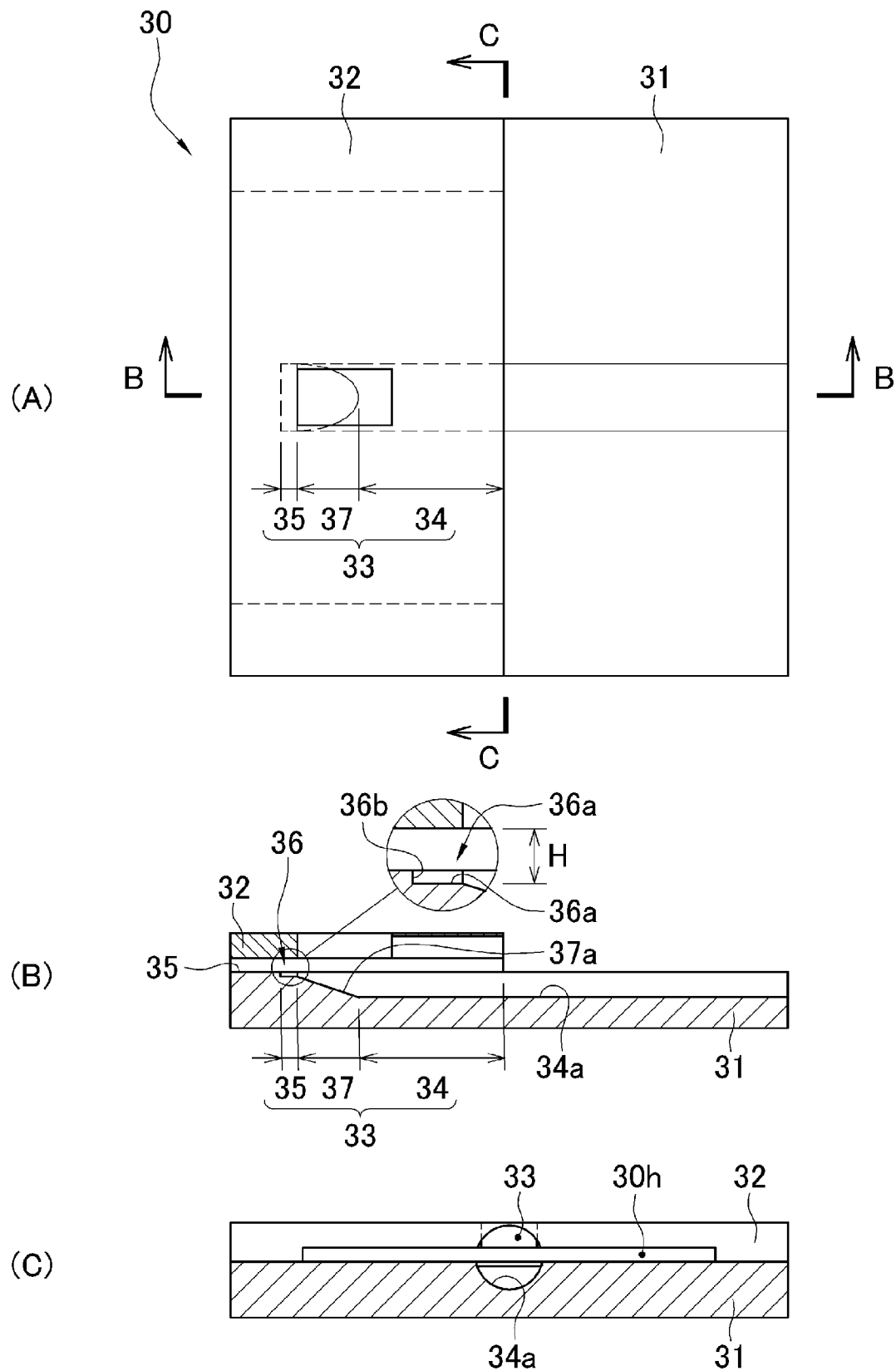
FIG. 4 illustrates schematic views of holding means 30 alone; and (A) is a plan view thereof, (B) is a cross sectional view taken along a B-B line of (A), and (C) is a cross sectional view taken along a C-C line of (A).
Figure 5:
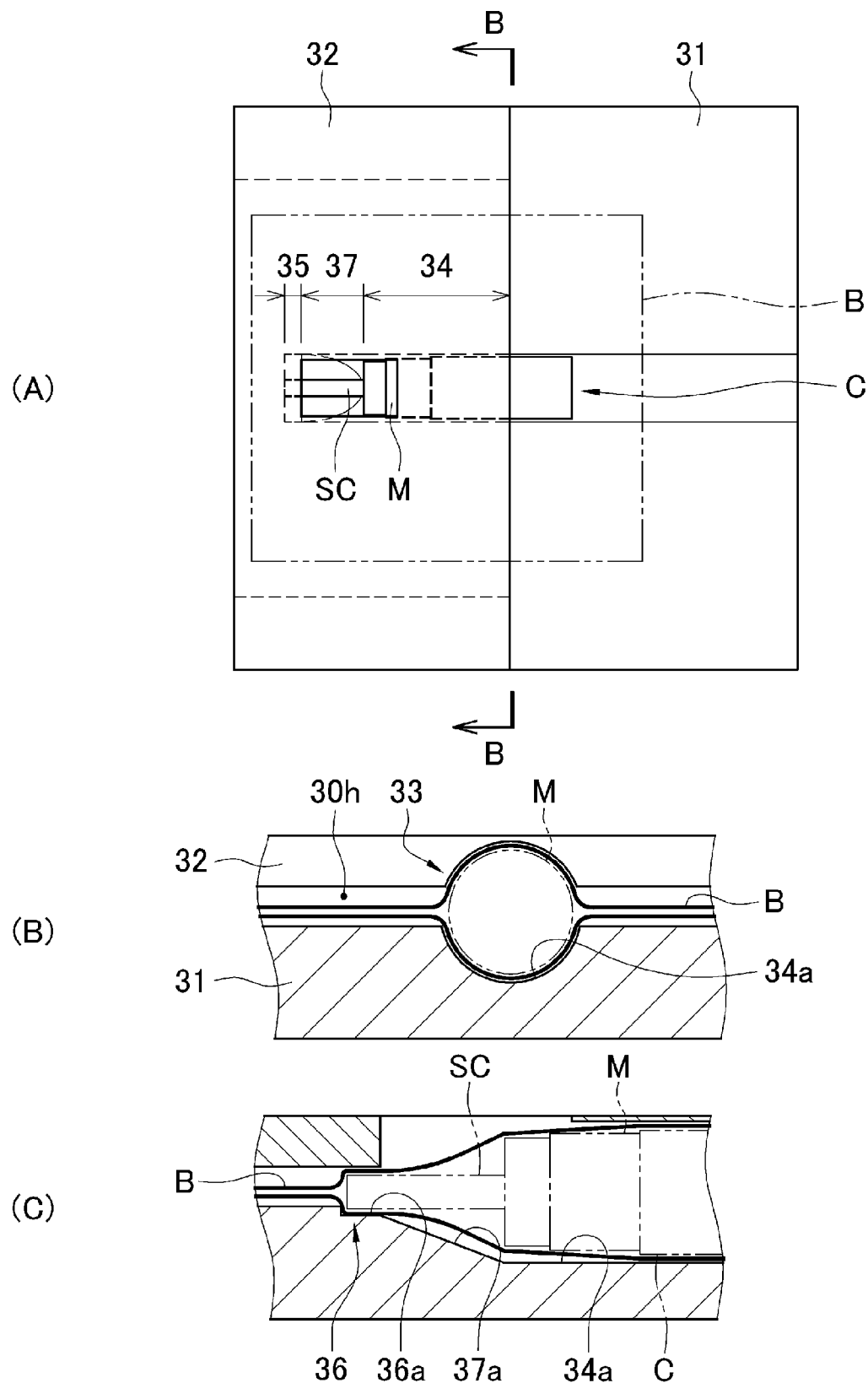
FIG. 5 illustrates schematic views when a cartridge C enclosed in a bag B is inserted into the holding means 30; and (A) is a plan view thereof, (B) is a cross sectional view taken along a B-B line of (A), and (C) is a schematic cross sectional view in the vicinity of a tip holding region 35.

In FIGS. 4 and 5, reference numeral 31 indicates a plate-like holding base. The nut member 23 and the pair of sliding members 25,25 are coupled to an under surface of the holding base 31. By being supported these members, the holding base 31 is provided so that a top surface thereof is parallel to the top surface of the base member 11. A width of the holding base 31 is wider than a width of the bag B housing the cartridge C.

As illustrated in FIGS. 4 and 5, a plate-like upper cover 32 is provided above the holding base 31. An under surface of the upper cover 32 is parallel to the top surface of the holding base 31, and a clearance 30h is formed between the under surface of the upper cover 32 and the top surface of the holding base 31 to extend through in a direction along which the holding means 30 moves.

In the upper cover 32 other than a part where a holding hole 33 described later is formed, a height of the clearance 30h is narrower than a thickness of the seed cartridge SC in the cartridge C and a width of the clearance 30h is wider than the width of the bag B housing the cartridge C.

The clearance 30h has the holding hole 33 of space for holding the cartridge C. The holding hole 33 extends toward the slit plate 15 from an opening (an opening at a right end in FIG. 4 or 5, hereinafter referred to as an insertion opening) located on the farther side from the slit plate 15. An axial direction of the holding hole 33 is parallel to a central axis of the screw shaft 22. That is, the holding hole 33 is formed so that the axial direction is perpendicular to the slit 15h.

Moreover, the holding hole 33 is formed so that a plane including an axial direction thereof and perpendicular to the top surface of the base member 11 divides the slit 15h into two equal parts. That is, the holding hole 33 is formed at a position where the holding hole 33 passes below the slit 15h when the moving means 20 causes the holding means 30 to move below the slit plate 15 in the housing space 10h.

As illustrated in FIGS. 4 and 5, the holding hole 33 has a magazine holding region 34 having the magazine M to be provided and a tip holding region 35 having the tip portion of the seed cartridge SC to be provided.

The magazine holding region 34 is a part formed into a substantially cylindrical shape. The magazine holding region 34 is formed by recessing both surfaces of the clearance (namely, the top surface of the holding base 31 and the under surface of the upper cover 32) and then by forming space to an extent that the magazine M can be housed between the both concave surfaces. The concave surface of the magazine holding region is formed so that a radius of curvature thereof is substantially the same as a radius of the magazine M of the cartridge C, for example.

The tip holding region 35 communicating with the magazine holding region 34 is formed on a side of the slit plate 15, which is closer to the slit plate 15 than the magazine holding region 34. The tip holding region 35 has a fixed groove 36 obtained by recessing the top surface of the holding base 31 downward.

A cross section of the fixed groove 36 is formed into a rectangular shape and a bottom surface 36a of the fixed groove 36 is formed into a flat surface parallel to the top surface of the holding base 31. In other words, the bottom surface 36a of the fixed groove 36 is formed into a flat surface parallel to the under surface of the upper cover 32.

An end surface 36b of the fixed groove 36 (that is, a surface on the side of the slit plate 15) is formed so as to be perpendicular to the axial direction of the holding hole 33. That is, the end surface 36b of the fixed groove 36 is formed so as to be parallel to the axial direction of the slit 15h.

The fixed groove 36 of the tip holding region 35 is formed so that a distance H from the bottom surface 36a to the under surface of the upper cover 32 is slightly smaller than a thickness D1 obtained by adding a thickness of the seed cartridge SC and a thickness of the bag B (a thickness obtained by adding a thickness of the pasteboard and a thickness of the cover sheet).

Since the distance H is slightly smaller than the thickness D1, the tip of the seed cartridge SC can be pressed into the tip holding region 35 with the cartridge C tightly enclosed in the bag B, as well as the seed cartridge SC can be fixed in the tip holding region 35. This is because a material of the bag B is slightly compressed as the distance H is slightly smaller than the thickness D1.

Since the bottom surface 36a of the fixed groove 36 is parallel to the under surface of the upper cover 32, pressing the tip of the seed cartridge SC into the tip holding region 35 allows the axial direction of the plurality of sources S loaded in the seed cartridge SC to become parallel to the under surface of the upper cover 32. In other words, the axial direction of the plurality of sources S loaded in the seed cartridge SC can become parallel to the under surface of the slit plate 15 (that is, the top surface of the base member 11).

When the seed cartridge SC is pressed until the tip surface thereof reaches the end surface 36b of the fixed groove 36, the tip surface of the seed cartridge SC can become parallel to the axial direction of the slit 15h. This is because the end surface 36b of the fixed groove 36 is formed so as to become parallel to the axial direction of the slit 15h. In other words, the axial direction of the plurality of sources S loaded in the seed cartridge SC can become parallel to the axial direction of the slit 15h.

According to the above configuration, the cartridge C can be fixed to the holding means 30 as follows.

A side opposite to the seed cartridge SC of the cartridge C in the bag B is first held, and then the cartridge C is inserted into the holding hole 33 of the holding means 30 from the insertion opening with the seed cartridge SC coming first. At this time, a part of the bag B not being located in the holding hole 33 is located in the clearance 30h.

When the cartridge C is pressed into the holding hole 33 in such a state, the magazine M is provided in the magazine holding region 34.

When the cartridge C is further pressed into the holding hole 33, the tip portion of the seed cartridge SC is pressed into and fixed in the tip holding region 35.

Then, the cartridge C tightly enclosed in the bag B can be fixed to the holding means 30 in a predetermined posture, that is, in a state of the axial direction of the plurality of sources S loaded in the seed cartridge SC being parallel to the axial direction of the slit 15h.

When the cartridge C is fixed to the holding means 30, the cartridge C needs only to be inserted and pressed into the holding hole 33. This allows the cartridge C tightly enclosed in the bag B to be easily fixed to the holding means 30 in a correct position/posture for a short time even if a worker wears protective gloves for prevention of radiation exposure.

In the case of the seed cartridge SC having a thickness of 3.1 mm and the bag B having a thickness of 0.23 mm (0.18 mm pasteboard and 0.05 mm synthetic resin sheet), for example, the distance H is assumed to be 3.1 mm. As a result, the cartridge C can be fixed to the holding means 30 so as to be in the correct position/posture by inserting and pressing the cartridge C into the holding hole 33 of the holding means 30 even if the worker wears protective gloves for prevention of radiation exposure.

In the case of fixing the cartridge C included in the bag B to the holding means 30, how to handle the part of the bag B not being provided in the holding hole 33 becomes a problem. However, the above holding means 30 has the clearance 30h with its height narrower than the thickness of the tip portion of the seed cartridge SC between the top surface of the holding base 31 and the under surface of the upper cover 32. Moreover, the clearance 30h extends through the holding means 30 along a moving direction of the holding means 30 and a width thereof is wider than that of the bag B. Therefore, the part of bag B not being provided in the holding hole 33 can be provided in the clearance 30h, preventing the part from disturbing the fixation and positioning of the cartridge C.

Here, the case where the clearance 30h extends through the holding means 30 along the moving direction has been described in the above example. However, the clearance 30h does not necessarily extend through the holding means 30 as long as space capable of housing the bag B provided ahead of the seed cartridge SC without being bent can be formed ahead of the fixed groove 36.

In the case of fixing the cartridge C included in the bag B to the holding means 30, a length of the holding base 31 (length in a horizontal direction in FIG. 4) is preferably longer than a length of the upper cover 32 (length in the horizontal direction in FIG. 4). In this case, a table-like portion (table region) can be formed in front of the insertion opening of the holding hole 33. When the cartridge C is inserted into the holding hole 33 with the part of the bag B not being provided in the holding hole 33 being in contact with the table region, the part can easily slide into the clearance 30h. This enables to further facilitate an operation of fixing the cartridge C included in the bag B to the holding means 30.

The above holding means 30 can be used not only for holding the cartridge C in the bag B, but also for holding a cartridge C taken out of the bag B. In such a case, the bag B cannot be used for fixing the tip of the seed cartridge SC. Accordingly, when a cushioning material having compressibility is attached to the surface of the seed cartridge SC, the cartridge C can be fixed to the holding means 30 by pressing the tip of the seed cartridge SC into the tip holding region 35. A sterilized zipper bag made of polyethylene having compressibility, for example, may be used as a cushioning material. With such a zipper bag, the seed cartridge SC can be fixed in the tip holding region 35 similarly to the case of the cartridge C in the bag B.

Further, in the case where the distance H is slightly larger than the thickness of the seed cartridge SC (for example, on the order of 200 μm), the cushioning material need not to be provided. The seed cartridge SC of the cartridge C cannot be tightly fixed in the tip holding region 35 in such a case. However, deviation of the position of the cartridge SC can be prevented by moving the cartridge C at the time of moving the holding means 30.

(Coupling Region 37)

Although the magazine holding region 34 formed in a substantially cylindrical shape may be directly coupled to the tip holding region 35 in the holding hole 33, a coupling region 37 may be provided therebetween as illustrated in FIG. 4.

As illustrated in FIGS. 4 and 5, the coupling region 37 is provided between the magazine holding region 34 and the tip holding region 35. The coupling region 37 has a curved surface communicating with a concave surface 34a of the magazine holding region 34 and an inclined plane 37a formed so as to cut the curved surface. The inclined plane 37a communicates with the bottom surface 36a of the fixed groove 36 and is formed as if the bottom surface 36a is bent downward.

Because of this, when the cartridge C is inserted and pressed into the holding hole 33, if the surface of the seed cartridge SC is inclined with respect to the bottom surface 36a of the fixed groove 36, the tip portion of the seed cartridge SC comes into contact with the inclined plane 37a of the coupling region 37.

The above described shape of the inclined plane 37a of the coupling region 37 causes the cartridge C to rotate so that a bottom edge of the tip portion of the seed cartridge SC comes into line contact with the inclined plane 37a of the coupling region 37 as the cartridge C is pressed.

Accordingly, the surface of the tip portion of the seed cartridge SC can be parallel to the bottom surface 36a of the fixed groove 36 by the time the tip portion of the seed cartridge SC reaches an entrance of the tip holding region 35.

That is, the above coupling region 37 can adjust the posture of the seed cartridge SC to be the same every time simply by pressing the cartridge C so that the axial direction of the sources S is parallel to the axial direction of the slit 15h.

(Slit Plate 15)

Although the above slit plate 15 may be produced by forming the slit 15h in one plate-like member, the slit plate 15 may be formed by joining two plate-like members 16 and 17 so that end surfaces thereof come into surface contact with each other, as illustrated in FIG. 1.

As illustrated in FIG. 1, the plate-like member 16 is provided on the pair of holding surfaces 14a,14a of the left-and-right pair of side walls 14,14 so that one end surface of the plate-like member 16 comes into surface contact with the reference inner surface 12a of the reference wall 12. The plate-like member 16 is formed so that the end surface being in surface contact with the reference inner surface 12a of the reference wall 12 (reference end surface 16a) is parallel to an end surface opposite to the end surface (opposite end surface 16b) and both of the end surfaces are flat and perpendicular to both surfaces of the plate-like member 16. That is, the plate-like member 16 is formed so that the opposite end surface 16b is parallel to the reference inner surface 12a when the reference end surface 16a comes into surface contact with the reference inner surface 12a of the reference wall 12.

On the other hand, the plate-like member 17 is provided on the pair of holding surfaces 14a,14a of the left-and-right pair of side walls 14,14 so that one end surface of the plate-like member 17 comes into surface contact with the opposite end surface 16b of the plate-like member 16. The plate-like member 17 is formed so that the end surface being in surface contact with the opposite end surface 16b of the plate-like member 16 (opposite end surface 17a) is flat and perpendicular to both surfaces of the plate-like members 16 and 17.

The opposite end surface 16b of the plate-like member 16 includes a concave portion 16c obtained by recessing the end surface. The concave portion 16c is formed so as to extend through both surfaces of the plate-like member 16.

Accordingly, when the opposite end surfaces 16b and 17a of the two plate-like members 16 and 17 are joined to each other and thus obtained plate-like members are provided on the pair of holding surfaces 14a, 14a so that the reference end surface 16a of the plate-like member 16 comes into surface contact with the reference inner surface 12a of the reference wall 12, the slit 15h extending through the slit plate 15 can be formed.

In the case of forming the slit plate 15 in such a manner, a very narrow slit 15h can be easily and correctly formed because a width of the slit 15h can be adjusted simply by adjusting a depth of the concave portion 16c formed in the opposite end surface 16b of the plate-like member 16.

Additionally, the axial direction of the slit 15h has to be maintained correctly parallel to the reference inner surface 12a of the reference wall 12. In the case of forming the slit plate 15 in the above described manner, if the both end surfaces 16a and 16b of the plate-like member 16 are formed to be parallel to each other and are maintained parallel to the bottom surface of the concave portion 16c, the axial direction of the slit 15h can be correctly maintained parallel to the reference inner surface 12a of the reference wall 12. Then, the slit 15h can be very simply and accurately formed, compared with the case where the slit 15h is formed in one plate as a through hole. For example, in the case where the slit plate 15 is formed by joining the opposite end surfaces 16b and 17a of the two plate-like members 16 and 17 to each other, the slit plate 15 can be accurately formed even if the width of the slit 15h is 0.1 to 0.01 mm.

In order to ensure the surface contact between the opposite end surfaces 16b and 17a of the two plate-like members 16 and 17, the two plate-like members 16 and 17 are preferably fixed to each other with a bolt or the like.

Additionally, regarding a plate-like member having a recess formed in the opposite end surface (the plate-like member 16 in the above example) out of the two plate-like members 16 and 17, the recess should always be provided in a predetermined position when the plate-like member is mounted on the pair of holding surfaces 14a, 14a of the left-and-right pair of side walls 14,14. A positioning mechanism for positioning a relative position between the pair of holding surfaces 14a,14a of the left-and-right pair of side walls 14, 14 and the plate-like member 16 therefore needs to be provided thereto. Various known positioning mechanisms can be employed as the positioning mechanism and, for example, a method in which a fixed position mark or the like is provided to align each of the plate-like members 16 and 17 based on the fixed position mark, or the like can be employed.

Although the case where the recess is formed in the opposite end surface 16b of the plate-like member 16 has been described in the above example, a recess may be formed in the opposite surface 17a of the plate-like member 17 to form the slit 15h without forming the recess in the opposite surface 16b of the plate-like member 16. The slit 15h may also be formed by forming a recess in each of the opposite surfaces 16b and 17a of the plate-like members 16 and 17.

(Regarding Housing Portion)

The above housing portion of the radiation intensity measuring means may be formed by assembling the separately processed base member 11, reference wall 12, left-and-right pair of side walls 14,14, and slit plate 15 or by integrally forming all of these components. Alternatively, a body portion including the base member 11, the reference wall 12 and the left-and-right pair of side walls 14,14 may be integrally formed and only the slit plate 15 can be attachable thereto and detachable therefrom.

However, in order to improve easiness in processing and processing accuracy, it is preferable that each of the base member 11, the reference wall 12, the left-and-right pair of side walls 14,14 and the slit plate 15 is separately formed with a plate-like member, followed by assembling, as described above.

(Radiation Intensity Measuring Apparatus in Second Embodiment)

A radiation intensity measuring apparatus 100 in a second embodiment will be described.

The radiation intensity measuring apparatus 100 in the second embodiment is characterized in that a period of time in which a worker handles the bag B loaded with the cartridge C can be reduced at the time of measuring radiation intensity of the source S, in other words, a possibility (time period) of the worker being exposed to radiation can be reduced.

(Description of Case 110)

Figure 6:
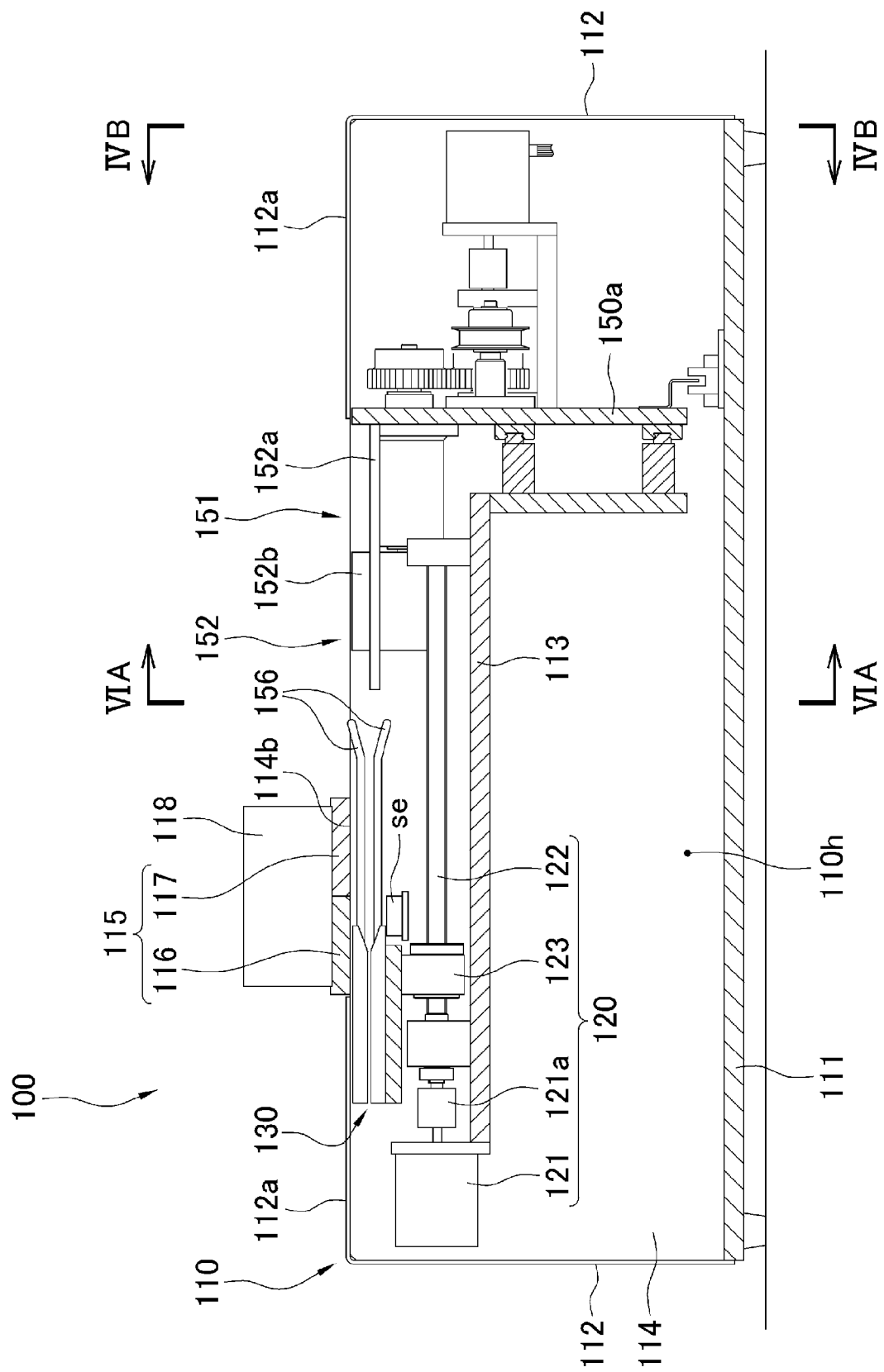
FIG. 6 is a schematic longitudinal cross sectional view illustrating a radiation intensity measuring apparatus 100 for an encapsulated sealed radioactive source for brachytherapy in a second embodiment.
Figure 7:
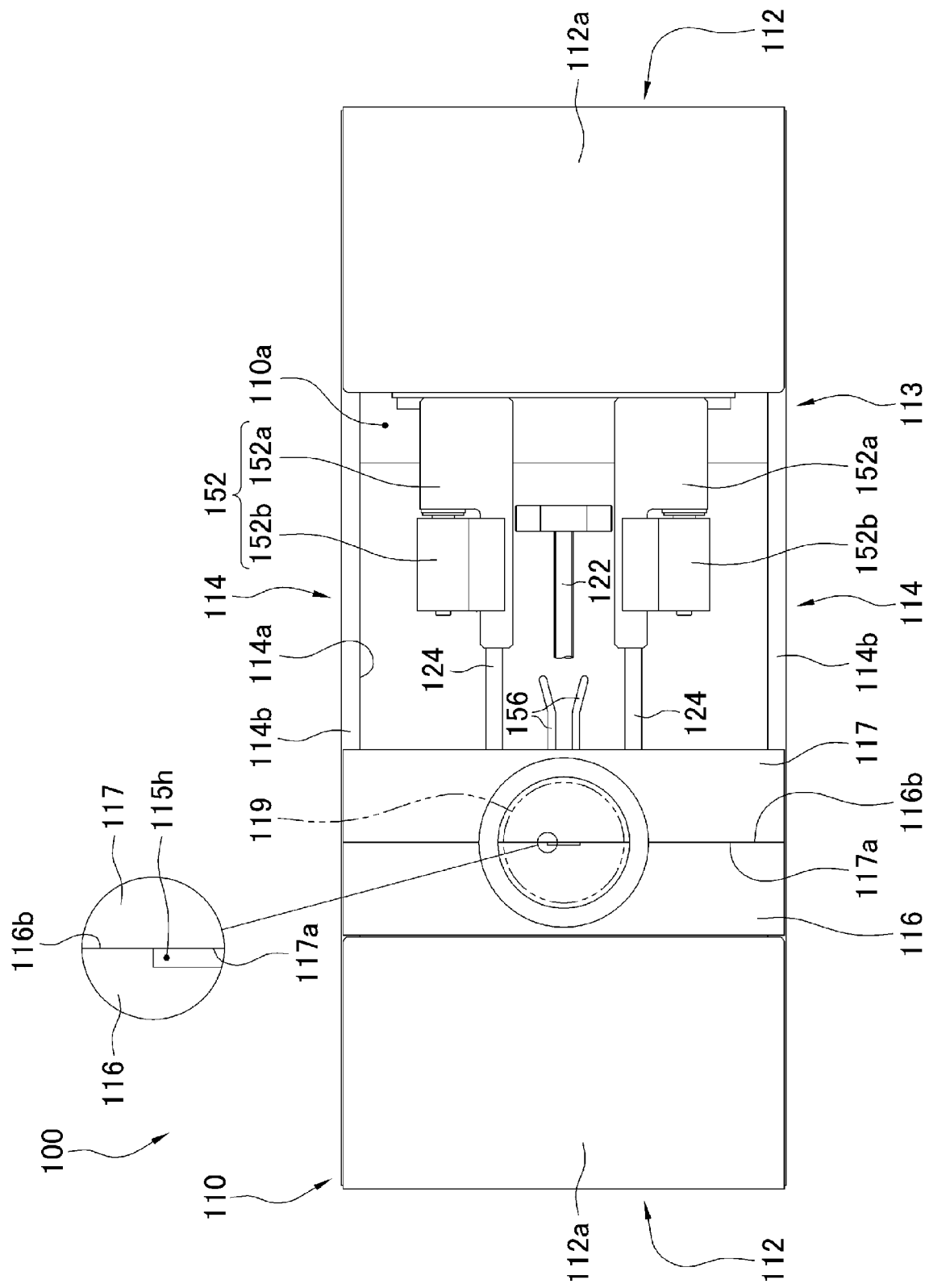
FIG. 7 is a schematic plan view illustrating the radiation intensity measuring apparatus 100 for an encapsulated sealed radioactive source for brachytherapy in the second embodiment.

In FIGS. 6 and 7, reference numeral 110 indicates a case of the radiation intensity measuring apparatus 100. The case 110 has a base member 111 of a base thereof. A top surface of the base member 111 is formed into a flat surface surrounded by a plurality of walls.

Specifically, a left-and-right pair of side walls 114,114 is provided on the sides of the base member 111. When a bottom edge of each left-and-right pair of side walls 114,114 is couples to a side edge of the base member 111, an inner surface of the side wall 114 formed into a flat surface becomes perpendicular to the top surface of the base member 111 (hereinafter, the inner surface is referred to as a reference inner surface 114a).

A pair of wall members 112,112 is also provided at front and rear edges (right and left edges in FIG. 6) of the base member 111. Each of side edges of the pair of wall members 112,112 is coupled to each of front edges and rear edges of the left-and-right pair of side walls 114,114, while each of bottom edges of the wall members 112,112 is coupled to each of front edges and rear edges of the base member 111.

That is, the case 110 has hollow space 110h with the base member 111 as a bottom and surrounded by the left-and-right pair of side walls 114,114 and the pair of wall members 112,112.

Further, each of the pair of wall members 112, 112 has a lid portion 112a bent toward the other wall member 112 at an upper part thereof. Each of the lid portions 112a is formed in size to an extent that an aperture 110a communicating between the space 110h and an outside is formed between both of the lid portions 112a. Right and left edges of each lid portion 112a are coupled to the left-and-right pair of side walls 114,114, respectively, at top edges of the side walls 114,114.

The aperture 110a corresponds to a supply opening for supplying a bag B housing a cartridge C (hereinafter, simply referred to as a bag B) to supplying means 150 described later, and the details will be described later.

(Description of Radiation Intensity Measuring Means)

A pair of holding surfaces 114b, 114b parallel to the top surface of the base member 111 (in other words, perpendicular to the reference inner surface 114a) and located on the same plane is formed at top edges of the left-and-right pair of side walls 114,114 in a part between the lid portions 112a.

A slit plate 115 is provided on the pair of holding surfaces 114b,114b. The slit plate 115 is a plate-like member having its under surface formed into a flat surface, and a slit 115h of a through hole extending through vertically is formed almost in the center thereof.

The slit 115h is formed so that an axial direction thereof is perpendicular to the reference inner surface 114a. Further, the slit 115h is formed so as to have a width thereof being narrower than a diameter of the source S, and the reason will be described later.

A material and a thickness of the slit plate 115 are not particularly limited. However, the slit plate 115 may be formed to an extent that radiations from the source S do not pass through a part other than the slit 115h or do not affect the measurement of radiation intensity of the source S even if the radiations pass through the slit 115h.

As illustrated in FIG. 6, a cylindrical radiation-blocking member 118 with a hollow structure is provided on a top surface of the slit plate 115. The radiation-blocking member 118 is formed with a material such as brass, copper and tungsten, and is provided so as to locate the slit 115h in a hollow part inside thereof. The hollow part of the radiation-blocking member 118 is a measuring apparatus housing portion 118h, and is a part having a measuring apparatus 119 for measuring radiation intensity emitted from the source S provided inside thereof.

The base member 111, the one of the wall member 112 (the wall member 112 on the left side in FIG. 6), the left-and-right pair of side walls 114,114 and the slit plate 115 correspond to a housing portion of radiation intensity measuring means according to claims. Space surrounded by these components corresponds to housing space of the housing portion of the radiation intensity measuring means according to claims.

The housing portion of the radiation intensity measuring means may be formed by assembling the separately processed base member 111, wall member 112, left-and-right pair of side walls 114,114, and slit plate 115 or by integrally forming all of these components. Alternatively, the base member 111, the wall member 112 and the left-and-right pair of side walls 114,114 may be integrally formed and only the slit plate 115 can be attachable thereto and detachable therefrom.

However, in order to improve easiness in processing and processing accuracy, it is preferable that each of the base member 111, the wall member 112, the side wall 114 and the slit plate 115 is separately formed with a plate-like member, followed by assembling, as described above.

(Description of Holding Means 130)

As illustrated in FIGS. 6 and 7, a reference plate 113 is provided between the left-and-right pair of side walls 114, 114. The reference plate 113 is provided so that a top surface thereof is parallel to the top surface of the base member 111.

As illustrated in FIGS. 6 and 7, holding means 130 is provided above the reference plate 113 in the space 110h of the case 110. The holding means 130 is formed in size to an extent that the holding means 130 can be housed in space between a screw shaft 122 of moving means 120 described later and the slit plate 115 (that is, the housing space of the housing portion).

The holding means 130 can hold the cartridge C in a predetermined posture. Specifically, the holding means 130 has a function of holding the cartridge C so that an axial direction of the sources S loaded in the cartridge C is parallel to the axial direction of the slit 115h. In other words, the holding means 130 has a function of holding the cartridge C so that a central axis of the magazine M is parallel to a perpendicular plane with respect to the axis of the slit 115h.

Details of the holding means 130 will be described later.

(Description of Supplying Means 150)

As illustrated in FIGS. 6 and 7, the supplying means 150 is provided above the reference plate 113 in the space 110h of the case 110. The supplying means 150 has a bag holding mechanism 151 provided at a position of the aperture 110a and having the bag B supplied thereto. The supplying means 150 has a function of positioning the cartridge C in the bag B held by the bag holding mechanism 151 and supplying the cartridge C to the holding means 130. Specifically, the supplying means 150 has a function of positioning the cartridge C so that the central axis of the magazine M of the cartridge C is parallel to a top surface of the reference plate 113 and parallel to the perpendicular plane with respect to the axis of the slit 115h, and supplying the cartridge C to the holding means 130. Details thereof will be described later.

(Description of Moving Means 120)

As illustrated in FIG. 6, the screw shaft 122 of the moving means 120 (for example, ball screw shaft) is provided above the top surface of the reference plate 113. One end (left end in FIG. 6) of the screw shaft 122 is located below the slit plate 115 and the other end (right end in FIG. 6) is located in the vicinity of the bag holding mechanism 151 of the supplying means 150. Moreover, the screw shaft 122 is provided so that a central axis thereof is parallel to the top surface of the reference plate 113 and parallel to the perpendicular plane with respect to the axis of the slit 115h.

The screw shaft 122 is screwed with a nut member 123 to which the holding means 130 provided above the screw shaft 122 is coupled.

Additionally, a main shaft of a motor 121 such as a stepping motor is coupled to one end of the screw shaft 122 via a coupling 121a.

The above configuration allows the holding means 130 together with the nut member 123 to move along an axial direction of the screw shaft 122 when the motor 121 is operated to rotate the screw shaft 122. In other words, the holding means 130 can be moved in parallel with the perpendicular plane with respect to the axis of the slit 115h and with the top surface of the reference plate 113 (parallel with the top surface of the base member 111) by the moving means 120.

The holding means 130 is formed in size to an extent that the holding means 130 can be housed in space between the screw shaft 122 and the slit plate 115. One end of the screw shaft 122 is provided below the slit plate 115 and the other end is provided in the vicinity of the bag holding mechanism 151 of the supplying means 150.

Therefore, operating the moving means 120 allows the holding means 130 to move between a position below the slit plate 115 and a position in the vicinity of the bag holding mechanism 151.

The holding means 130 holds the cartridge C so that the central axis of the magazine M is parallel to the top surface of the reference plate 113 and parallel to the perpendicular plane with respect to the axis of the slit 115h. The central axis of the magazine M therefore becomes parallel to the axial direction of the screw shaft 122 in the cartridge C held by the holding means 130.

Then, the central axis of the cartridge C held by the holding means 130 is always maintained parallel to the axial direction of the screw shaft 122 even if the moving means 120 moves the holding means 130. In other words, the cartridge C held by the holding means 130 is maintained so that the central axis of the magazine M is always parallel to the top surface of the reference plate 113 and parallel to the perpendicular plane with respect to the axis of the slit 115h.

(Configuration for Supporting Movement of Holding Means 130)

A pair of rails 124,124 parallel to the screw shaft 122 is provided on the top surface of the reference plate 113, as illustrated in FIG. 6. The movement of the holding means 130 may be guided by sliding members (for example, a bearing truck) movably provided along an axial direction of the rails 124,124. That is, a guide portion for guiding the movement of the holding means 130 may be provided. If the guide portion is provided, the holding means 130 can be moved in a more stable state.

Additionally, the moving means is not limited to the above structure, for example, a cylinder, an arm and the like can be used for the moving means, while a wire and the like can be used for the guide portion. However, stability of the movement of the holding means 130 can be enhanced when the holding means 130 is moved along the screw shaft 122 and the pair of rails 124,124, that is, three linear members, as described above.

(Radiation Intensity Measurement by Radiation Intensity Measuring Apparatus 100 in Second Embodiment)

With the above configuration, the radiation intensity measuring apparatus 100 in the second embodiment can measure radiation intensity of each of the sources S loaded in the cartridge C according to a method described below.

The measuring apparatus 119 is first provided in the measuring apparatus housing portion 118h of the radiation-blocking member 118 provided on a top surface of the slit plate 115. When the cartridge C with sources S having their radiation intensity to be measured is inserted into the holding means 130, preparation for the measurement is completed.

After the preparation for the measurement is completed, the bag B housing the cartridge C is supplied to the bag holding mechanism 151 of the supplying means 150. When the holding means 130 is moved in the vicinity of the bag holding mechanism 151 by operation the motor 121, the positioned cartridge C housed in the bag B is supplied to the holding means 130.

When the positioned cartridge C is supplied from the bag holding mechanism 151 of the supplying means 150 to the holding means 130, the moving means 120 causes the holding means 130 to move below the slit plate 115.

At this time, when the holding means 130 is moved so that the sources S held by the holding means 130 pass through a position of the slit 115h, the measuring apparatus 119 can measure intensity of radiations passing through the slit 115h.

The holding means 130 holds the cartridge C so that the axial direction of the plurality of sources S loaded in the cartridge C is parallel to the axial direction of the slit 115h. The plurality of the sources S therefore sequentially pass through the position of the slit 115h with their axial direction parallel to the axial direction of the slit 115h when the holding means 130 moves along the screw shaft 122. Since a width of the slit 115h is formed to be narrower than the diameter of the sources S, radiation intensity detected by the measuring apparatus 119 changes according to the movement of the plurality of sources S.

Specifically, since the width of the slit 115h is narrower than the diameter of the source S, only a part of radiations emitted from the source S pass through the slit 115h. Consequently, the measuring apparatus 119 detects only the radiations passing through the slit 115h. The radiations emitted from the source S are radially emitted from the central axis of the source S, and therefore, radiation intensity detected by the measuring apparatus 119 reaches the maximum when the central axis of the slit 115h corresponds to the central axis of the source S. Conversely, the radiation intensity is more and more reduced as a deviation between the both central axes becomes larger. Accordingly, if the axial direction of the plurality of the sources S is maintained parallel to the axial direction of the slit 115h during the movement, the radiation intensity detected by the measuring apparatus 119 shows variations according to the movement of the plurality of sources S. That is, the radiation intensity reaches a peak at the timing when the central axis of each source S corresponds to the central axis of the slit 115h, whereas the radiation intensity becomes low between the central axes of the sources S adjacent to each other.

Accordingly, radioactivity of each of the sources S can be calculated based on the variations of the thus measured radiation intensity, namely the number of peaks of the radiation intensity, a peak value thereof, and timing of the peak.

With the above configuration, the radiation intensity measuring apparatus 100 in the second embodiment allows the holding means 130 to hold the positioned cartridge C when the bag B housing the cartridge C loaded with the plurality of sources S is supplied to the bag holding mechanism 151 of the supplying means 150. Then, the holding means 130 with the cartridge C is moved so that all of the sources S pass through the position of the slit 115h. This enables to measure radiation intensity of each of the sources S at one measurement with the plurality of sources S (namely, all of the sources S) loaded in the cartridge C and the cartridge C enclosed in the bag B. Radioactivity of the plurality of sources S loaded in the cartridge C can therefore be measured automatically to some extent for a short time.

Moreover, when the bag B including the cartridge C is supplied to the bag holding mechanism 151 of the supplying means 150, a worker can measure radiation intensity of the sources without touching the bag B or the like during a subsequent operation. That is, a period of time in which the worker handles the cartridge C can be reduced, and therefore, a possibility (time period) of the worker being exposed to radiation can be further reduced.

When only a part of the sources S out of the plurality of sources S loaded in the cartridge C is intended to be measured, not all of the sources S necessarily pass through the position of the slit 115h. The holding means 130 may be moved so that the sources S intended to be measured pass through the position of the slit 115h.

Moreover, since the variations of the radiation intensity are measured by moving the plurality of sources S loaded in the cartridge C, a peak value of a variation curve of the radiation intensity, or the presence or absence of the peak value can be grasped even if loading intervals for the sources S are slightly deviated from each other.

Radiation intensity of each of the sources S can therefore be measured correctly even if positions of the sources S loaded in the cartridge C are slightly deviated from each other.

While a velocity of the movement of the holding means 130 is not particularly limited, and the velocity is acceptable as long as the variations of the radiation intensity appear to an extent that radioactivity of each of the sources S can be calculated.

In the case of grasping an absolute value of the radiation intensity of each source S, a variation curve of radiation intensity with respect to a cartridge C loaded with reference sources S having radiation intensity as a standard may be measured before measurement of a target cartridge C. Then, the absolute value of radiation intensity of each source S loaded in the target cartridge C can be grasped based on a measured value (peak value) of the target cartridge C with a peak value of the reference source as a standard.

Additionally, if the absolute value of radiation intensity of each source S is not necessary, intercomparison of the peak values of respective sources S in the variation curve of the radiation intensity enables to grasp quality of each source S.

Although the case where the radiation intensity measuring apparatus 100 includes the radiation-blocking member 118 has been described in the above example, the radiation-blocking member 118 is not necessarily provided.

However, the radiation-blocking member 118 can prevent scattered radiations of the target sources S or outside radiations from entering into a region where the measuring apparatus 119 detects radiations passing through the slit 115h. The radiations passing through the slit 115h can therefore be measured accurately even if there is an agent, equipment and the like emitting radiations around the radiation intensity measuring apparatus 100 such as in a medical site. This enables to accurately grasp the quality of each of the sources S.

(Detailed Description of Holding Means 130 and Supplying Means 150)

As described above, the radiation intensity measuring apparatus 100 in the second embodiment allows the holding means 130 to hold the positioned cartridge C when the bag B housing the cartridge C is supplied to the bag holding mechanism 151 of the supplying means 150. Accordingly, a period of time in which the worker handles the bag B including the cartridge C can be reduced, and therefore, a possibility (time period) of the worker being exposed to radiation can be further reduced.

Hereinafter, configurations of the holding means 130 and the supplying means 150 important for obtaining the above effects will be described in detail.

(Detailed Description of Holding Means 130)

The holding means 130 will now be described in detail.

As described above, the holding means 130 is for holding the cartridge C in the predetermined posture and can hold the cartridge C even enclosed in the bag B in the predetermined posture. Specifically, the holding means 130 can hold the cartridge C enclosed in the bag B so that a perpendicular plane with respect to the axis of the slit 115h (hereinafter, simply referred to as a perpendicular plane) is perpendicular to the axial direction of the sources loaded in the seed cartridge SC.

Hereinafter, a reference axis refers to an axis coaxial with the central axis of the magazine M at the time of the cartridge C being held by the holding means 130, more specifically, an axis parallel to the top surface of the reference plate 113 and parallel to the perpendicular plane with respect to the axis of the slit 115h.

Figure 8:
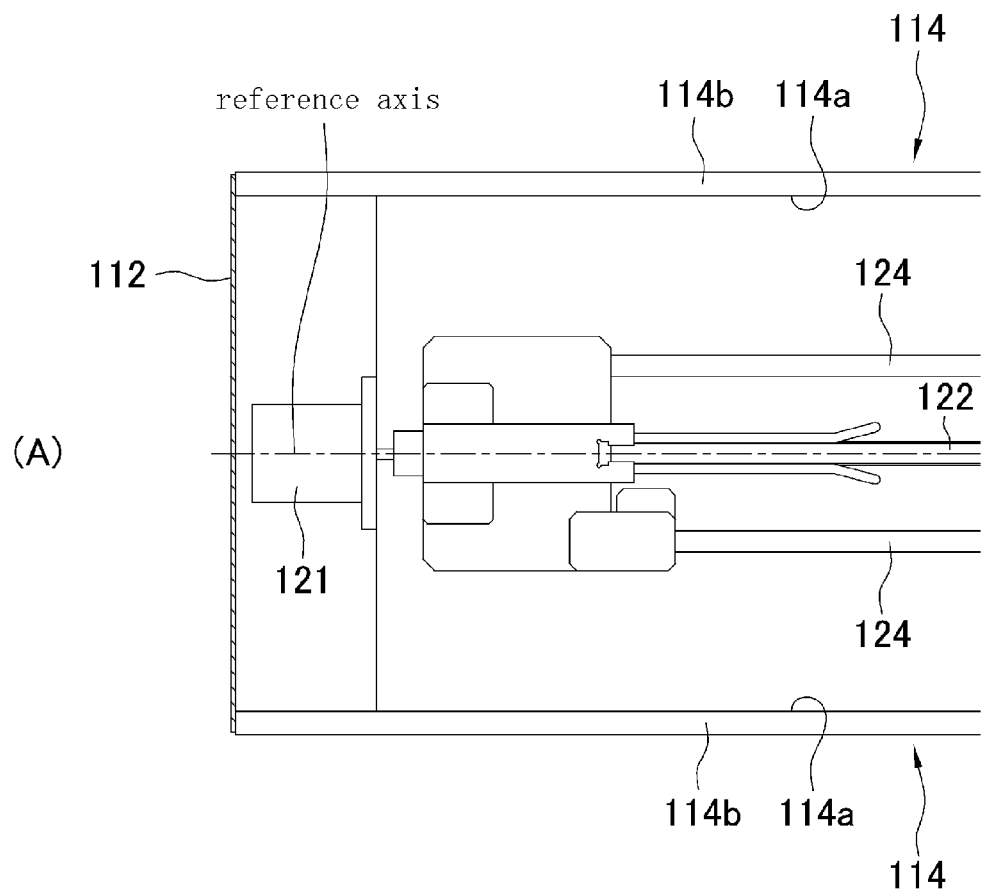
FIG. 8 illustrates schematic enlarged views in the vicinity of holding means 130, and (A) is a plan view thereof and (B) is a side view thereof.
Figure 8:
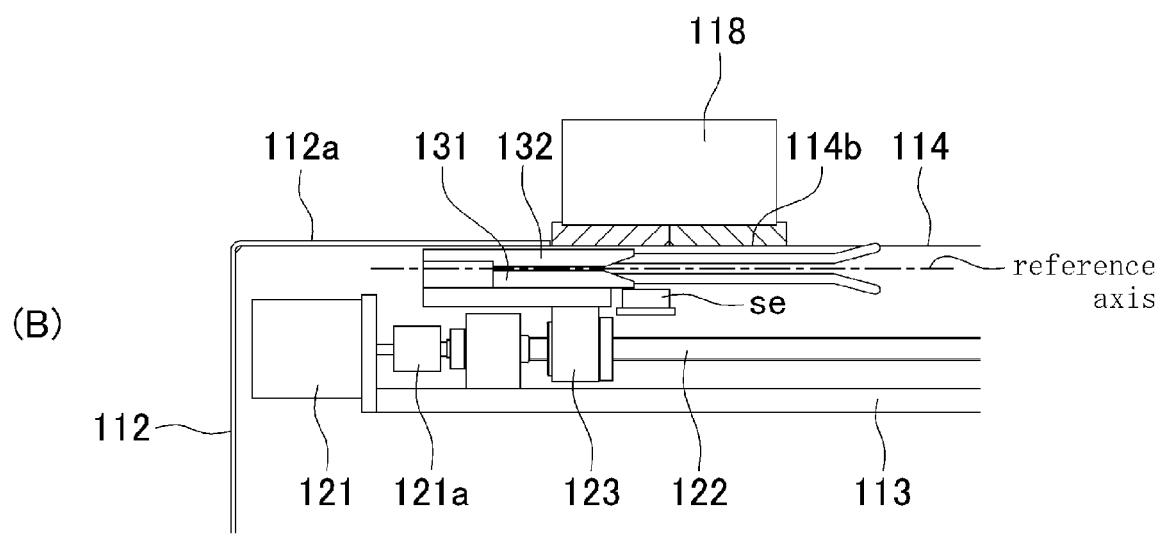
Figure 10:
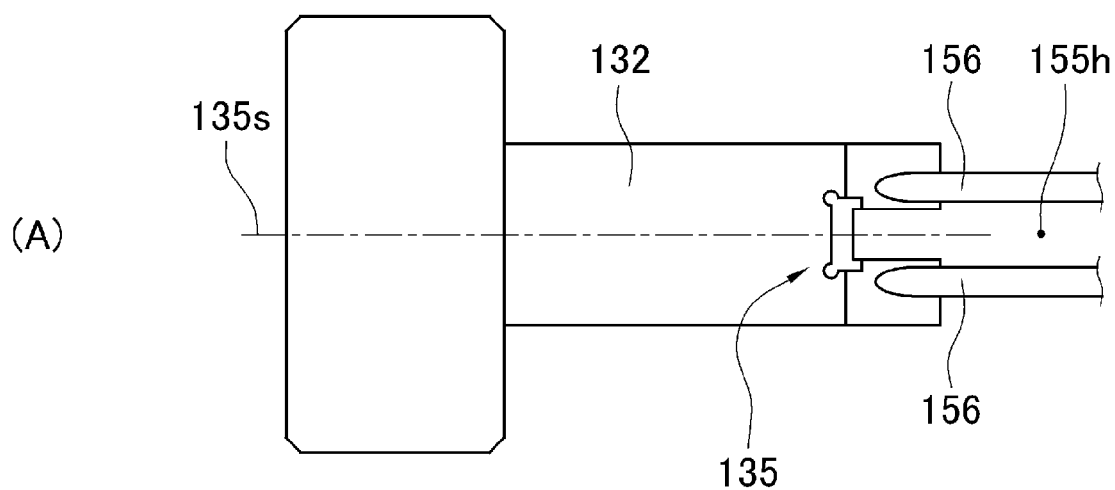
FIG. 10 illustrates schematic views of the holding means 130 alone.
Figure 10:
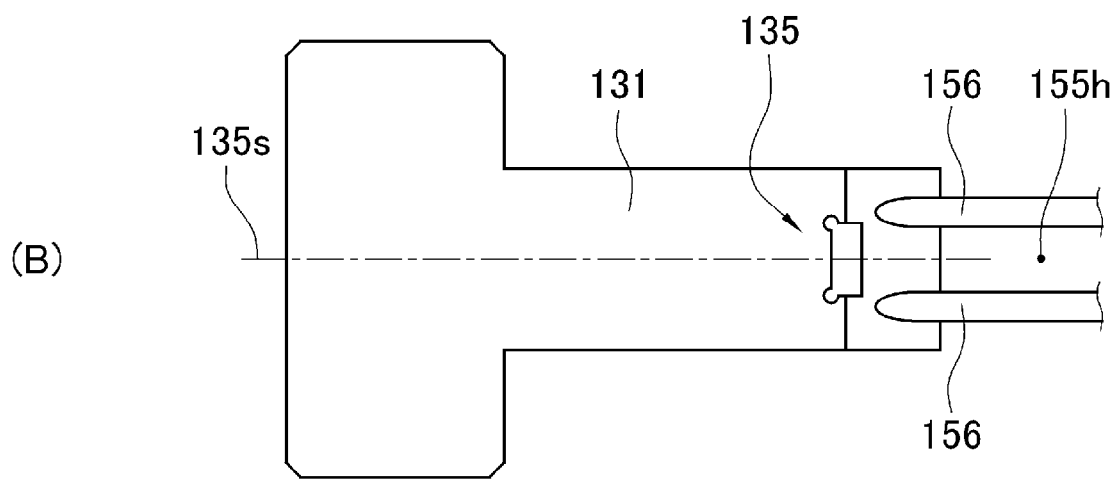

As illustrated in FIGS. 8 and 10, the holding means 130 has a lower holding member 131 and an upper holding member 132 for holding the seed cartridge SC.

A top surface of the lower holding member 131 is formed into a flat surface, and the above nut member 123 and pair of sliding members 124,124 are coupled thereto via a plate-like member. The lower holding member 131 is provided so that the top surface thereof is parallel to the top surface of the reference plate 113.

The upper holding member 132 having an under surface thereof formed into a flat surface is provided above the lower holding member 131. The under surface of the upper holding member 132 is parallel to the top surface of the lower holding member 131. A clearance 130h extending through in a direction along which the holding means 130 moves is further provided between the under surface of the upper holding member 132 and the top surface of the lower holding member 131. Specifically, the upper holding member 132 is provided so that a height of the clearance 130h is smaller than the thickness of the cartridge SC in the cartridge C and is larger than a thickness of the bag B for housing the cartridge C (a thickness obtained by adding a thickness of the pasteboard and a thickness of the cover sheet) (hereinafter, simply referred to as the thickness of the bag B).

(Description of Tip Holding Region 135)

A tip holding region 135 of space for holding the tip of the seed cartridge SC in the cartridge C is formed between the lower holding member 131 and the upper holding member 132. The tip holding region 135 extends from an end on the side of the supplying means 150 (right end in FIG. 9 or 10, and hereinafter referred to as an insertion end) to an end opposite to the supplying means 150 (hereinafter, referred to as an opposite insertion end).

The tip holding region 135 is provided so that the an axial direction thereof is parallel to the reference axis and a plane 135s including a central axis thereof and perpendicular to the top surface of the reference plate 113 divides the slit 115h into two equal parts.

The tip holding region 135 is formed with a pair of recesses provided in the top surface of the lower holding member 131 and the under surface of the upper holding member 132.

The recess formed in the top surface of the lower holding member 131 (hereinafter, referred to as a fixed groove 136) is formed so that a cross section thereof has a rectangular shape and a bottom surface 136a thereof is a flat surface parallel to the top surface of the lower holding member 131.

An end surface 136b of the fixed groove 136 (that is, a surface on the side of the opposite insertion end) is formed so as to be perpendicular to an axial direction of the tip holding region 135. That is, the end surface 136b of the fixed groove 136 is formed so as to be parallel to the axial direction of the slit 115h and perpendicular to the top surface of the reference plate 113.

Similarly, the recess formed in the under surface of the upper holding member 132 (hereinafter, referred to as a fixed groove 137) is formed so that a cross section thereof has a rectangular shape and a bottom surface 137a thereof is a flat surface parallel to the top surface of the lower holding member 131. In other words, the bottom surface 137a of the fixed groove 137 is formed into a flat surface parallel to the bottom surface 136a of the fixed groove 136.

An end surface 137b of the fixed groove 137 (that is, a surface on the side of the opposite insertion end) is formed so as to be perpendicular to the axial direction of the tip holding region 135. Moreover, the end surface 137b of the fixed groove 137 is formed so as to be located on the same plane as the end surface 136b of the fixed groove 136.

The tip holding region 135 is formed so that a distance H from the bottom surface 136a of the fixed groove 136 to the bottom surface 137a of the fixed groove 137 is slightly smaller than the thickness obtained by adding the thickness of the seed cartridge SC and the thickness of the bag B. In the case of the seed cartridge SC having a thickness of 3.1 mm and the bag B having a thickness of 0.23 mm (0.18 mm pasteboard and 0.05 mm synthetic resin sheet), for example, the distance H is assumed to be 3.1 mm.

Since the distance H is slightly smaller than the thickness D1, the tip of the seed cartridge SC can be housed in the tip holding region 135 with the cartridge C tightly enclosed in the bag B, as well as the seed cartridge SC can be fixed in the tip holding region 135. This is because the bag B is made of a material slightly compressible and the distance H is slightly smaller than the thickness D1, and therefore, the seed cartridge SC is provided in the tip holding region 135 with the material of the bag B slightly compressed.

Since the bottom surface 136a of the fixed groove 136 is parallel to the bottom surface 137a of the fixed groove 137, housing the tip of the seed cartridge SC in the tip holding region 135 allows the axial direction of the plurality of sources S loaded in the seed cartridge SC to become parallel to the under surface of the upper holding member 132. In other words, the axial direction of the plurality of sources S loaded in the seed cartridge SC can become parallel to the under surface of the slit plate 115 (that is, the top surface of the reference plate 113).

Then, the seed cartridge SC is provided so that a tip surface thereof reaches an end surface of the tip holding region 135, namely the end surface 136b of the fixed groove 136 and the end surface 137b of the fixed groove 137. The tip surface of the seed cartridge SC can become parallel to the axial direction of the slit 115h because the end surface 136b of the fixed groove 136 and the end surface 137b of the fixed groove 137 are formed so as to be parallel to the axial direction of the slit 115h. In other words, the axial direction of the plurality of sources S loaded in the seed cartridge SC can become parallel to the axial direction of the slit 115h.

Figure 11:
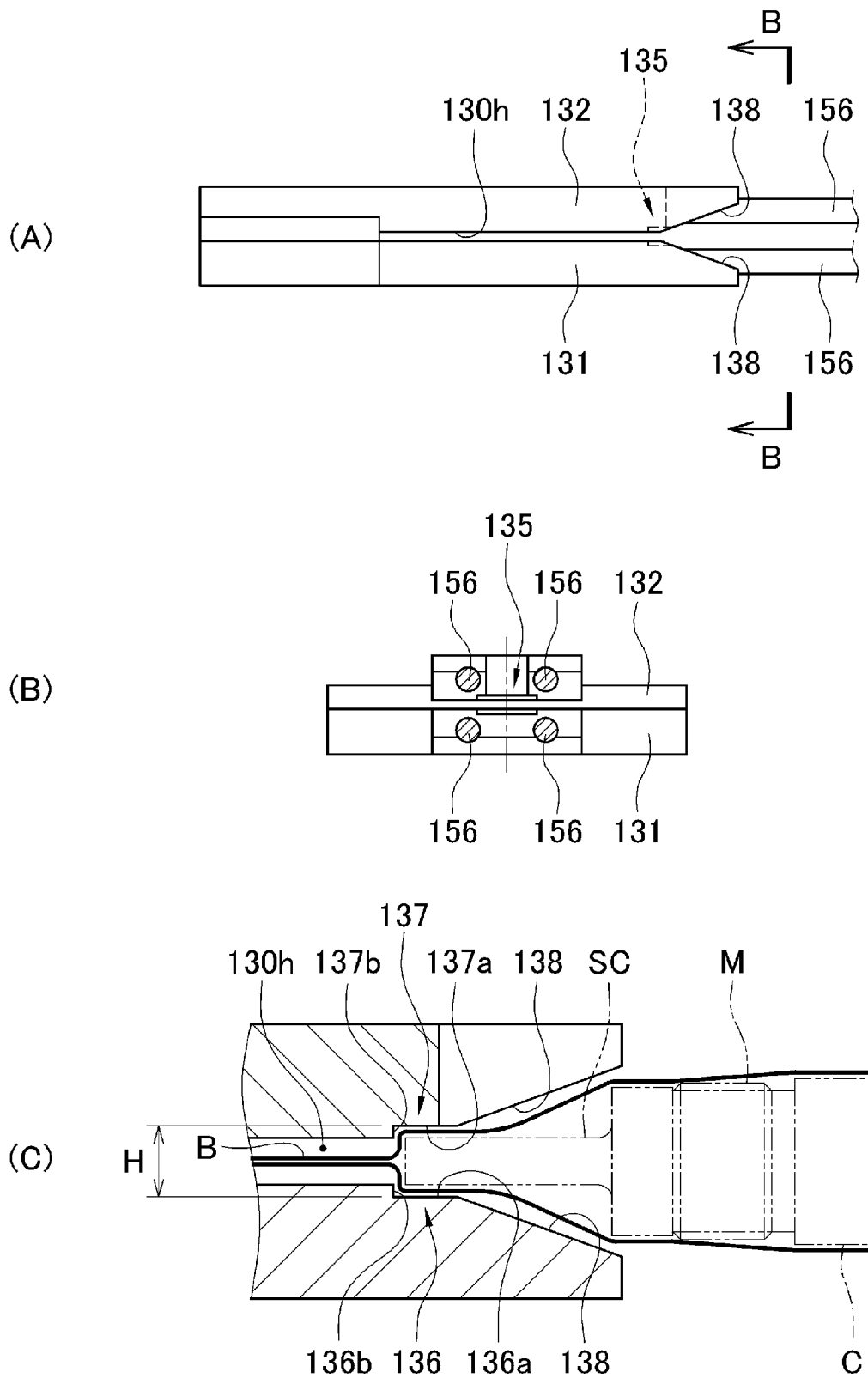
FIG. 11 illustrates schematic views of the holding means 130 alone; and (A) is a side view thereof, (B) is a cross sectional view taken along a B-B line of (A), and (C) is a schematic view of a tip holding region.

As illustrated in FIG. 11, if the clearance 130h is formed so that its clearance becomes wider from the tip holding region 135 toward the insertion end, the tip of the seed cartridge SC can be easily housed in the tip holding region 135, preferably.

Moreover, if the clearance 130h extends through in the direction along which the holding means 130 moves, the bag B provided ahead of the seed cartridge SC can be housed without being bent. Therefore, the bag B is advantageously prevented from disturbing the housing of the tip of the seed cartridge SC in the tip holding region 135. However, the clearance 130*h* does not necessarily extend through the holding means 130 as long as space capable of housing the bag B provided ahead of the seed cartridge SC without being bent can be formed ahead of the fixed groove 136.

(Detailed Description of Supplying Means 150)

The supplying means 150 will now be described in detail.

Figure 9:
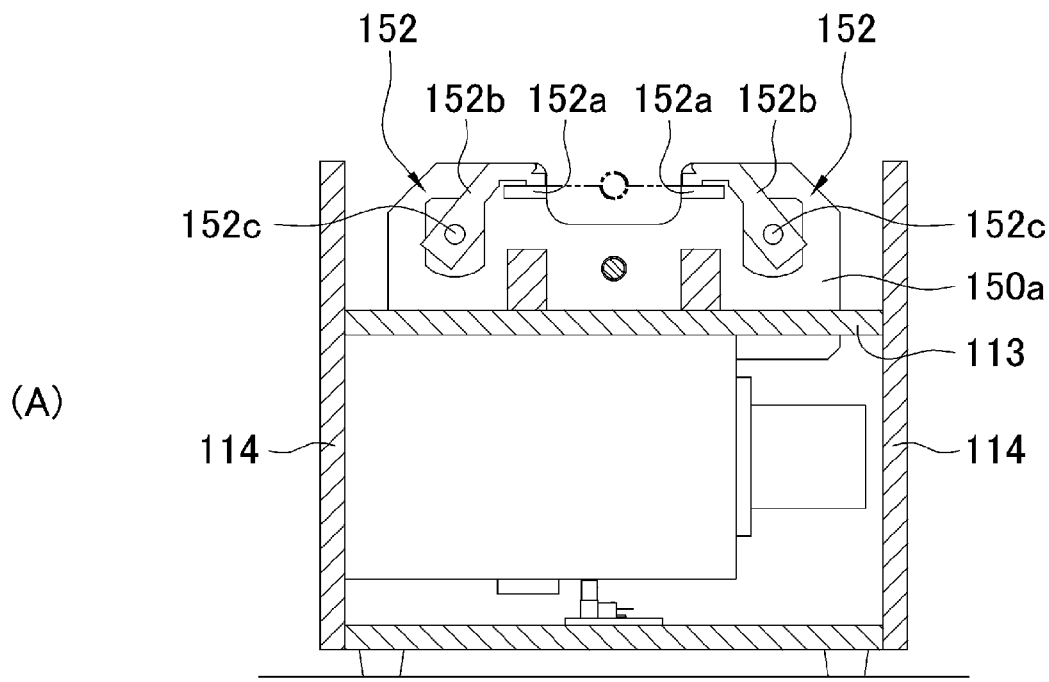
FIG. 9(A) is a cross sectional view taken along an IVA-IVA line of FIG. 6, and FIG. 9(B) a cross sectional view taken along an IVB-IVB line of FIG. 6.
Figure 9:
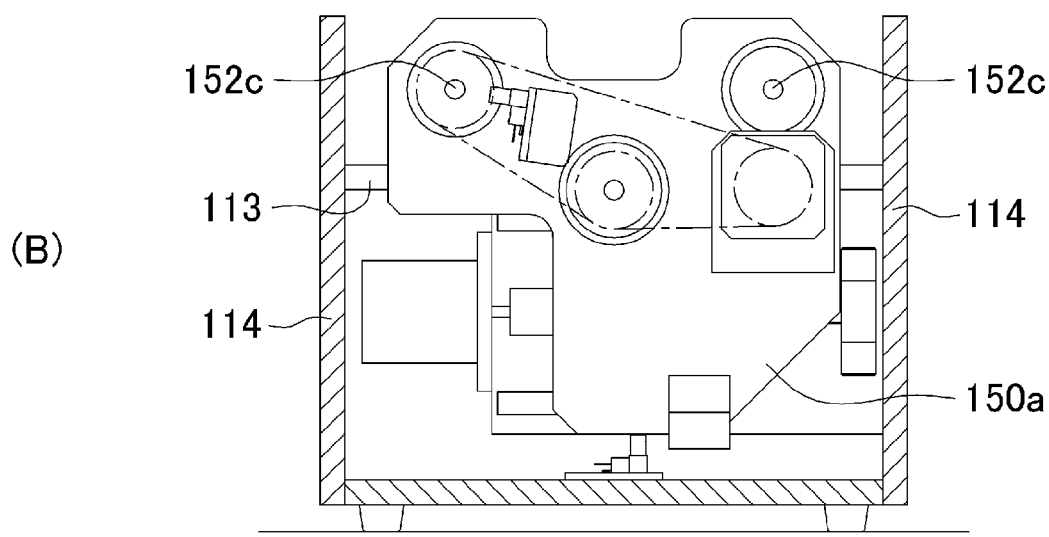

As illustrated in FIGS. 6 and 9, a moving wall 150*a* movable along a direction perpendicular to the perpendicular plane is provided in the hollow space 110*h* of the case 110. As a mechanism for moving the moving wall 150*a*, for example, such a mechanism may be employed that the moving wall 150*a* is slidably mounted to a rail provided so as to be perpendicular to the perpendicular plane and the moving wall 150*a* is moved by a ball screw mechanism that can rotate a screw shaft by a motor or the like. However, a specific configuration of the mechanism for moving the moving wall 150*a* is not particularly limited as long as the moving wall 150*a* can be moved along the direction perpendicular to the perpendicular plane.

(Detailed Description of Bag Holding Mechanism 151)

A pair of bag holding portions 152,152 in the bag holding mechanism 151 to which the bag B is supplied via the aperture 110*a* of the case 110 is provided on the moving wall 150*a*. The pair of bag holding portions 152,152 is provided with the perpendicular plane sandwiching therebetween so as to clip and hold both ends of the bag B in the width direction. Specifically, the pair of bag holding portions 152,152 is provided so that a distance therebetween in the direction perpendicular to the perpendicular plane is slightly smaller than the width of the bag B and the distance is adjusted to an extent that the both ends of the bag B can be held by the pair of bag holding portions 152,152 (preferably, the bag B is held in a stretched manner to some extent).

As illustrated in FIG. 9, each of the pair of bag holding portions 152,152 has a holder 152*a* fixed to the moving wall 150*a*. The holder 152*a* is a member having its top surface formed into a flat surface and the top surfaces of the holders 152*a* in the pair of bag holding portions 152, 152 are provided on the same plane.

Moreover, the top surface of each holder 152*a* is provided on a plane perpendicular to the perpendicular plane and including the reference axis (hereinafter, referred to as a central plane).

As illustrated in FIG. 9, a rocker shaft 152*c* is provided beside each holder 152*a*. Each of the rocker shafts 152*c* has its central axis provided parallel to the reference axis and is ratatably held by the moving wall 150*a*. Additionally, rotating means for rotating the rocker shaft 152*c* with a driving source such as a motor is coupled to a base end of each rocker shaft 152*c*.

On the other hand, a base end of each of presser members 152*b* is mounted at a tip of each rocker shaft 152*c*. A clip portion is formed at a tip of the presser member 152*b*. The clip portion moves close to and away from a top surface of the holder 152*a* when the rocker shaft 152*c* is rotated. The clip portion has a clip surface coming into surface contact with the top surface of the holder 152*a* upon approaching the top surface of the holder 152*a*.

According to the above structure, both ends of the bag B are placed on the top surfaces of holders 152*a* so that the cartridge C is located between the pair of bag holding portions 152,152, with the clip portions of the presser members 152*b* in the pair of bag holding portions 152,152 keeping away from the top surfaces of the holders 152*a*. When, in such a state, the rocker shafts 152*c* are rotated causing the clip portions of the presser members 152*b* to approach the top surfaces of the holders 152*a*, the both ends of the bag B can be clipped and held by the pair of bag holding portions 152,152 with the cartridge C provided between the pair of bag holding portions 152,152.

(Detailed Description of Positioning Mechanism 155)

As illustrated in FIGS. 6 and 8, four shaft-like members 156 of positioning mechanism 155 are provided at the insertion ends of the lower holding member 131 and the upper holding member 132 of the holding means 130. Each base end of the four shaft-like members 156 is fixed to the insertion end of the lower holding member 131 or the upper holding member 132.

Moreover, the four shaft-like members 156 are provided so that axial directions thereof are parallel to the reference axis.

The four shaft-like members 156 are provided so that the central plane is located between two shaft-like members 156 fixed to the lower holding member 131 and two shaft-like members 156 fixed to the upper holding member 132.

A distance between the shaft-like members 156 adjacent to each other among the four shaft-like members 156 is adjusted to be shorter than the diameter of the magazine M of the cartridge C. Further, a distance between the shaft-like members 156 located on a diagonal line is slightly longer than the diameter of the magazine M of the cartridge C when the four shaft-like members 156 are viewed from a direction of the reference axis.

The four shaft-like members 156 are provided so that distances from the reference axis to each of the four shaft-like members 156 become equal to each other. Then, space for housing the cartridge C and having its central axis coaxial with the reference axis (hereinafter, referred to as magazine housing space 155*h*) is formed at a part surrounded by the four shaft-like members 156.

According to the above configuration, the cartridge C can be held in the magazine housing space 155*h* when the magazine housing space 155*h* formed with the four shaft-like members 156 of the positioning mechanism 155 houses the magazine M of the cartridge C. Specifically, the cartridge C is held so as not to move in a direction perpendicular to the central axis of the magazine housing space 155*h*.

Since the central axis of the magazine housing space 155*h* is coaxial with the reference axis, the central axis of the magazine M of the cartridge C can be positioned to be substantially coaxial with the reference axis when the magazine housing space 155*h* houses the magazine M of the cartridge C.

The four shaft-like members 156 of the positioning mechanism 155 are formed in a shape that each of the tip portions bends outward from the magazine housing space 155*h*. That is, the four shaft-like members 156 are formed so that a distance between inner surfaces of the shaft-like members 156 located on the diagonal line in the magazine housing space 155*h* becomes longer as getting close to tips thereof. The reason why such a shape is employed will be described later.

(Supply Operation of Cartridge C)

According to the above configuration, the cartridge C can be supplied to the holding means 130 with the cartridge C positioned by the supplying means 150 as follows.

The bag B tightly enclosing the cartridge C therein is first provided between the pair of bag holding portions 152, 152 in the bag holding mechanism 151. Since a distance between the pair of bag holding portions 152,152 is adjusted to the above described distance at this time, the both ends of the bag B can be placed on the top surfaces of the holders 152*a* in the pair of bag holding portions 152,152.

When, in such a state, the rocker shafts 152*c* are rotated causing the presser members 152*b* to rock so that the clip portions of the presser members 152b approach the top surfaces of the holders 152a, the both ends of the bag B are each clipped between the top surface of the holder 152a and the clip surface of the clip portion. Since the bag B is held by the bag holding mechanism 151 (preferably, held in a stretched manner to some extent), the bag B is provided so that a height thereof is adjusted substantially the same as that of the central plane.

When the bag holding mechanism 151 holds the bag B, the motor 121 of the moving means 120 is operated, causing the holding means 130 to move toward the bag holding mechanism 151 along the screw shaft 122.

Since the four shaft-like members 156 are provided so that the central plane is located between the two shaft-like members 156 fixed to the lower holding member 131 (hereinafter, referred to as lower shaft-like members 156) and the two shaft-like members 156 fixed to the upper holding members 132 (hereinafter, referred to as upper shaft-like members 156), the bag B is housed between the lower shaft-like members 156 and the upper shaft-like members 156 of the positioning mechanism 155 when the holding means 130 approaches the bag holding mechanism 151.

(In the Case Where Central Axis of Magazine M Substantially Corresponds to Central Axis of Magazine Housing Space 155h)

Assuming that the cartridge C held by the bag holding mechanism 151 is provided so that the central axis of the magazine M of the cartridge C is substantially parallel to the central axis of the magazine housing space 155h, and is located in the vicinity of the central axis of the magazine housing space 155h. When the holding means 130 approaches the bag holding mechanism 151 in such a case, the cartridge C is housed in the magazine housing space 155h in a state of being positioned. That is, the cartridge C is housed in a state of the central axis of the magazine M and the central axis of the magazine housing space 155h corresponding to each other.

After the cartridge C is housed in the magazine housing space 155h, the holding means 130 approaches the bag holding mechanism 151. The tip of the seed cartridge SC of the cartridge C then enters into the tip holding region 135.

When the tip surface of the seed cartridge SC reaches a position of the end surface of the tip holding region 135, the movement of the holding means 130 by the moving means 120 is terminated. Then, the cartridge C is held by the holding means 130 in the state of being positioned so that the axial direction of the sources S loaded in the seed cartridge SC is parallel to the slit 115h (that is, perpendicular to the perpendicular plane with respect to the axial direction of the slit 115h).

Simultaneously, the rocker shafts 152c rotate, causing the presser members 152b to be rocked so that the clip portions of the presser members 152b are apart from the top surfaces of the holders 152a. This causes the bag B to be released from the pair of bag holding portions 152,152.

When the bag B is released from the pair of bag holding portions 152, 152, the holding means 130 holding the cartridge C is moved below the slit plate 115 by the moving means 120. Then, the sources S held by the holding means 130 pass through the position of the slit 115h with the axial direction of the sources S maintained parallel to the axial direction of the slit 115h. The measuring apparatus 119 can therefore measure radiation intensity of the sources S passing through the slit 115h.

Although the above moving means 120 corresponds to a cartridge supplying mechanism of supplying means according to claims, the cartridge supplying mechanism is not limited to the above configuration.

For example, if a mechanism for causing the bag holding mechanism 151 instead of the holding means 130 to approach the holding means 130 is employed, the mechanism corresponds to the cartridge supplying mechanism.

Additionally, an apparatus for pressing the cartridge C provided in the magazine housing space 155h toward the holding means 130 such as a cylinder mechanism may be employed as the cartridge supplying mechanism.

However, if the moving means 120 also functions as the cartridge supplying mechanism, the configuration of the apparatus can be advantageously simplified.

A method for detecting whether the tip surface of the seed cartridge SC reaches the end surface of the tip holding region 135, that is, the cartridge C is supplied in the state of being positioned to the holding means 130 is not particularly limited. For example, in the case of the cartridge C having a metal part, a sensor for detecting the metal part is provided on the holding means 130 and then determination whether the above state is obtained may be made based on a signal from the sensor.

Specifically, as illustrated in FIG. 6, a metal detector SE is provided below the magazine housing space 155h. The metal detector SE is provided so as to react to the metal part of the cartridge C when the tip surface of the seed cartridge SC reaches the end surface of the tip holding region 135. This allows the metal detector to detect whether the cartridge C is supplied in the state of being positioned to the holding means 130.

In the case of employing the method, it is apparent that, based on the signal from the metal detector, the termination of the movement of the holding means 130 by the moving means 120 and the release of the bag B from the bag holding mechanism 151 are performed simultaneously with the detection of the metal part of the cartridge C by the metal detector.

(In the Case Where Central Axis of Magazine M is Deviated from Central Axis of Magazine Housing Space 155h)

Assuming that the cartridge C is provided so that the central axis of the magazine M of the cartridge C held by the bag holding mechanism 151 is slightly inclined with respect to the central axis of the magazine housing space 155h (for example, on the order of 42.75 degrees (in the case of 65 mm length and 8 mm width of the cartridge and 50 mm distance between the pair of the bag holding portions 152,152)), or is located at a position slightly deviated from the central axis of the magazine housing space 155h (for example, a position deviated on the order of 40 mm (in the case of 10 mm outside diameter of the cartridge and 50 mm distance between the pair of the bag holding portions 152,152)). Even in such a case, the cartridge C can be moved in the bag B so that the axial direction of the magazine M corresponds to the central axis of the magazine housing space 155h if the tip of the cartridge C with the bag B held by the bag holding mechanism 151 is located in a region surrounded by the tips of the four shaft-like members 156. This is because the four shaft-like members 156 have a shape of being bent outward.

Specifically, when the holding means 130 approaches the bag holding mechanism 151, an outer surface of the magazine M of the cartridge C comes into contact with an inner surface of the tip of any of the four shaft-like members 156 via the bag B. The inner surface of the tip of the shaft-like member 156 is inclined toward the central axis of the magazine housing space 155h. Accordingly, as the holding means 130 further approaches the bag holding mechanism 151, the magazine M of the cartridge C moves along the inner surface of the tip according to the approach and moves until the axial direction of the magazine M corresponds to the central axis of the magazine housing space 155*h*. When the holding means 130 furthermore approaches the bag holding mechanism 151, the magazine M of the cartridge C enters into a part in the magazine housing space 155*h* parallel to the central axis of the magazine housing space 155*h* in the four shaft-like members 156. The cartridge C can therefore be positioned so that the axial direction of the magazine M corresponds to the central axis of the magazine housing space 155*h*.

(In the Case of Moving Moving Wall 150*a*)

If the moving wall 150*a* is moved back and forth parallel to the central plane, while the holding means 130 approaches the bag holding mechanism 151, the cartridge C can be particularly easily positioned.

Specifically, a position of the cartridge C is changed along a direction perpendicular to the central axis of the magazine housing space 155*h*, while the holding means 130 approaches the bag holding mechanism 151. The cartridge C is then pressed by the shaft-like members 156 toward a direction of the central axis of the magazine housing space 155*h*. Thus, the cartridge C can be certainly moved for a short time with the central axis of the magazine M corresponding to the central axis of the magazine housing space 155*h*.

(In the Case of Rotating Cartridge C)

In order to insert the tip of the seed cartridge SC into the tip holding region 135, a surface of the seed cartridge SC needs to be parallel to the bottom surface 136*a* of the fixed groove 136 and the bottom surface 137*a* of the fixed groove 137 of the tip holding region 135 (hereinafter, the above state is referred to as a predetermined posture of the seed cartridge SC).

It is assumed that the surface of the seed cartridge SC is inclined with respect to the bottom surface 136*a* of the fixed groove 136 and the like with the bag B being held by the bag holding mechanism 151. If the inclination is small and an inclined plane 138 is formed so that the clearance 130*h* becomes wider from the tip holding region 135 to the insertion end (in other words, the clearance 130*h* becomes narrower as getting close to the tip holding region 135), the seed cartridge SC can be in the predetermined posture.

The reason will be described below.

When the distance between the seed cartridge SC and the tip holding region 135 becomes shorter with the inclined plane being in contact with the tip of the seed cartridge SC, the tip of the seed cartridge SC moves along the inclined plane toward the tip holding region 135.

As described above, the inclined plane is formed so that the clearance 130*h* becomes narrower as getting close the tip holding region 135. Moreover, the movement of the cartridge C housed in the magazine housing space 155*h* is restrained in the direction perpendicular to the axial direction of the magazine M, as described above.

Accordingly, the cartridge C rotates so that a vertical height becomes small, as the distance between the seed cartridge SC and the tip holding region 135 becomes shorter. Then, an edge of the tip portion of the seed cartridge SC in the cartridge C comes into line contact with the inclined plane by the time the tip of the seed cartridge SC reaches the tip holding region 135.

That is, with formation of the above inclined plane, the seed cartridge SC rotates so as to be in the predetermined posture, as the distance between the seed cartridge SC and the tip holding region 135 becomes shorter.

Accordingly, in the case where the seed cartridge SC is inclined compared with the predetermined posture with the bag B held by the bag holding mechanism 151, if the inclination is small, the tip of the seed cartridge SC can be inserted into the tip holding region 135.

On the other hand, it is assumed that the surface of the seed cartridge SC is significantly inclined with respect to the bottom surface 136*a* of the fixed groove 136 and the like with the bag B being held by the bag holding mechanism 151. The seed cartridge SC may not be in the predetermined posture in such a case even if the tip of the seed cartridge SC comes into contact with the inclined plane.

However, the movement of the cartridge C housed in the magazine housing space 155*h* is restrained in the direction perpendicular to the axial direction of the magazine M. Therefore, if the moving wall 150*a* is moved back and forth parallel to the central plane with the cartridge C housed in the magazine housing space 155*h*, the cartridge C can be rotated in the bag B.

Then, the tip of the seed cartridge SC can be inserted into the tip holding region 135 if the cartridge C can be rotated until the seed cartridge SC is adjusted to be in the predetermined posture.

Additionally, even if the cartridge C cannot be rotated until the seed cartridge SC is adjusted to be in the predetermined posture, it is acceptable that the cartridge C may be rotated to some extent. When the tip of the seed cartridge SC approaches the tip holding region 135, the tip of the seed cartridge SC can be inserted into the tip holding region 135. This is because the seed cartridge SC can be in the predetermined posture, as described above.

The cartridge C can be rotated in the bag B by moving the moving wall 150*a* back and forth parallel to the central plane with the cartridge C housed in the magazine housing space 155*h*. The reason will be described below.

Figure 12:
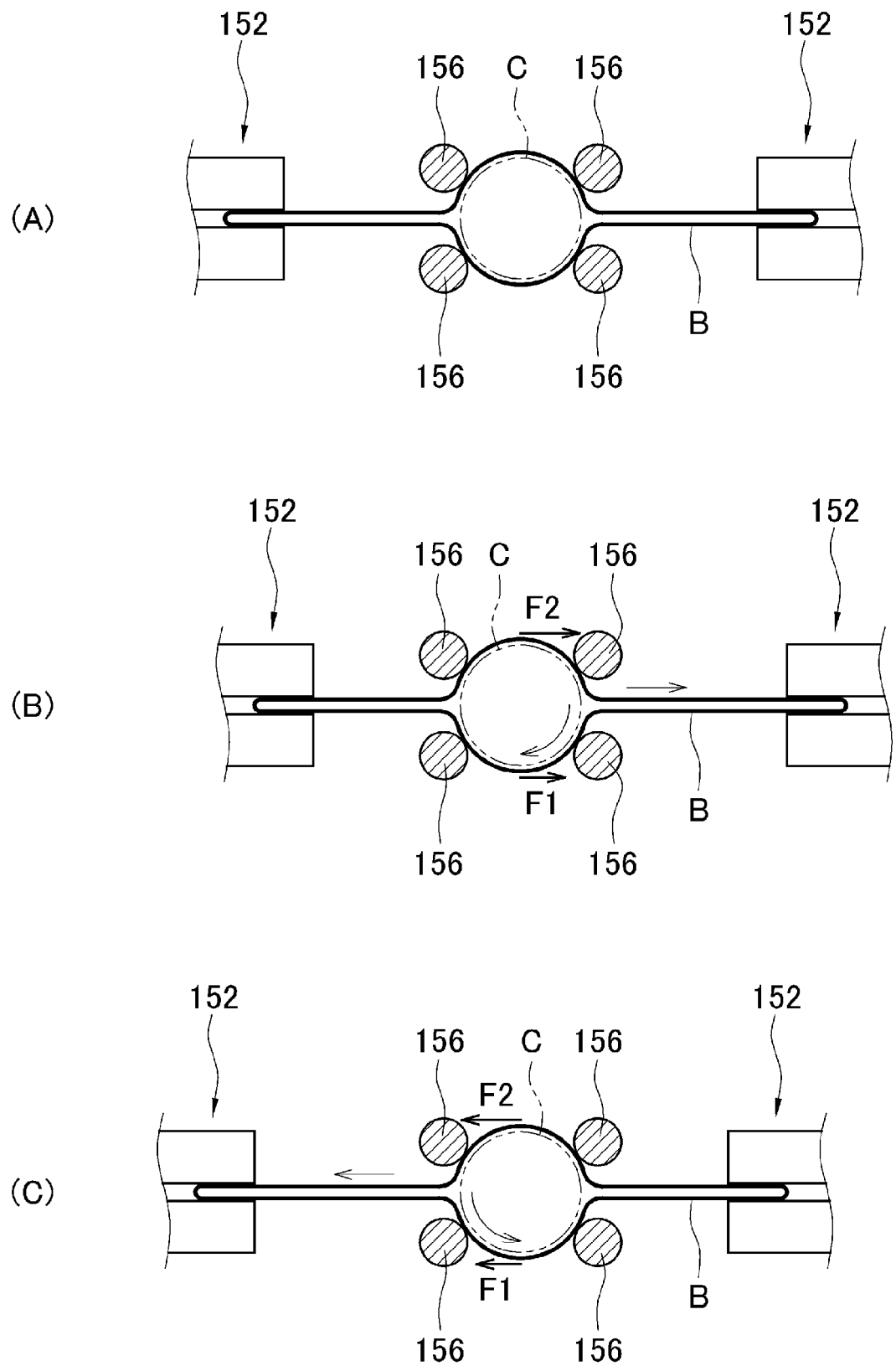

As illustrated in FIG. 12, as the moving wall 150*a* moves, the pair of bag holding portions 152,152 mounted to the moving wall 150*a* also moves. Therefore, the bag B held by the pair of bag holding portions 152,152 also moves in the direction perpendicular to the central axis of the magazine housing space 155*h*.

However, when the cartridge C is housed in the magazine housing space 155*h*, the bag B is to move while an inner surface thereof slides on the surface of the cartridge C. This is because the cartridge C cannot move in the direction perpendicular to the central axis of the magazine housing space 155*h*. Friction is then generated between the inner surface of the bag B and the surface of the cartridge C according to the movement of the bag B.

Here, the bag B is formed by sandwiching the cartridge C between sheets made of different materials (a sheet made of paper (pasteboard) and a sheet made of synthetic resin (cover sheet)) and sticking peripheries thereof together. Since a friction resistance of an inner surface of the pasteboard is different from a friction resistance of an inner surface of the cover sheet in magnitude, a force F1 caused by friction force generated between the inner surface of the pasteboard and the surface of the cartridge C is different from a force F2 caused by friction force generated between the inner surface of the cover sheet and the surface of the cartridge C in magnitude.

Then, a force causing the cartridge C to rotate along the surface thereof is generated with respect to the cartridge C resulting from a difference between the force F1 and the force F2. Therefore, when the moving wall 150*a* is moved causing the bag B to move, the cartridge C can be rotated.

With the above configuration, the posture of the cartridge C can be adjusted to the predetermined posture allowing the holding means 130 to hold the cartridge C without a worker adjusting the posture of the cartridge C even if the cartridge C in the bag B is rotated from the predetermined posture with the cartridge C held by the bag holding mechanism 151.

This enables to reduce a possibility of the worker being exposed to radiation because a period of time for which the worker is in contact with the cartridge C in the bag B can be shortened at the time of radiation intensity measurement of the sources.

The above described moving wall 150a and mechanism for moving the moving wall 150a correspond to a position changing portion according to claims.

Note that the inclined plane may be provided on a part into which the seed cartridge SC is inserted even in the case where the clearance 130h between the lower holding member 131 and the upper holding member 132 in the holding means 130 is formed so as not to be wider as getting close to the insertion end from the tip holding region 135. Then, the cartridge C can preferably be rotated so that the seed cartridge SC is in the predetermined posture, when the holding means 130 approaches the bag holding mechanism 151.

(Another Example of Bag Holding Mechanism 151)

A supporting plate located below the top surfaces of the holders 152a may be provided between the holders 152a. Such a supporting plate allows the pair of bag holding portions 152, 152 to hold the both ends of the bag B when the pair of bag holding portions 152, 152 is operated with the bag B placed on the supporting plate. A worker therefore need not to hold the bag B until the pair of bag holding portions 152, 152 holds the both ends of the bag B. This enables to reduce a possibility of the worker being exposed to radiation because a period of time for which the worker is in contact with the bag B can be shortened.

Additionally, the top surfaces of the holders 152a in the pair of bag holding portions 152,152 are not necessarily located on the same plane as the central plane, and may be provided in the vicinity of the central plane (for example, a position deviated from the central plane on the order of a several millimeters) or may be slightly inclined to the central plane. That is, the pair of bag holding portions 152,152 may hold the bag B (preferably, hold the bag B in a stretched manner to some extent) so that parts located on the both sides of the cartridge C in the bag B can be smoothly inserted into the clearance 130h between the lower holding member 131 and the upper holding member 132 in the holding means 130, when the holding means 130 approaches the bag holding mechanism 151.

Further, the structure of each bag holding portion 152 is not particularly limited. A structure may be employed as long as the pair of bag holding portions 152,152 may hold the bag B (preferably, hold the bag B in a stretched manner to some extent) so that the parts located on the both sides of the cartridge C in the bag B can be smoothly inserted into the clearance 130h between the lower holding member 131 and the upper holding member 132 in the holding means 130.

Furthermore, a structure of the rotating means for rotating the rocker shafts 152c is not particularly limited. Rotating means causing each of the rocker shafts 152c to rotate individually, or rotating means causing the both of the rocker shafts 152c to rotate simultaneously may be provided. As illustrated in FIG. 9(B), for example, one rotating means allows the both rocker shafts 152c to synchronize with each other and rotate when a belt mechanism or the like couples between the rocker shafts 152c. Such a structure enables to reduce the number of rotating means in the apparatus, thereby being able to make the apparatus compact. Additionally, the pair of bag holding portions 152,152 can more certainly hold the bag B because the both rocker shafts 152c can be more certainly synchronize with each other and operate.

(Another Example of Positioning Mechanism)

Although the four shaft-like members 156 correspond to a positioning portion of positioning mechanism according to claims in the above example, the tip portion may not be bent outward and the whole part may be formed with a straight bar-like member in each of the four shaft-like members 156. However, as described above, the tip portion preferably has a shape being bent outward in order to certainly supply the cartridge C to the holding means 130.

The configuration of the positioning means is not limited to the above (four shaft-like members 156). A configuration may be employed as long as the central axis of the magazine M of the cartridge C in the bag B held by the bag holding mechanism 151 can be positioned to be coaxial with the reference axis.

For example, a pair of shaft-like members 156,156 may be provided on the upper holding member 132 in the holding means 130, while a plate-like supporting member may be provided on the lower holding member 131. Even in such a case, if the supporting member is provided so that the central plane is placed between the pair of shaft-like members 156, 156 and the supporting member and a distance between the pair of shaft-like members 156,156 and the top surface of the supporting member is narrower than the diameter of the magazine M in the cartridge C, the cartridge C can be positioned preventing the cartridge C from moving in the direction perpendicular to the magazine housing space 155h.

Even in such a case, if the tip portions of the pair of shaft-like members 156,156 are bent upward so as to be apart from each other as getting close to the tips, the cartridge C can be advantageously easily provided in the magazine housing space 155h.

Additionally, forming a groove obtained by recessing a top surface of the supporting member is more preferred in that the cartridge C can be stably provided. Specifically, an inner surface of the groove is preferably formed into a cylindrical surface in which a radius of the inner surface is slightly longer than a radius of the magazine M with the central axis of the magazine housing space 155h as a central axis. The cartridge C can be then positioned certainly when the magazine M of the cartridge C is housed in the groove of the supporting member.

A plate-like supporting member may also be provided on each of the upper holding member 132 and the lower holding member 131 in the holding means 130 instead of the four shaft-like members 156. In such a case, grooves or the like are formed in surfaces facing each other of the both supporting members, and then the magazine housing space 155h may be formed between the grooves. Specifically, the groove may be formed into a cylindrical surface in which an inner surface of the groove is coaxial with the reference axis.

In particular, when a part in the vicinity of an insertion end in the inner surface of the groove is formed so as to become wider as getting close to the insertion end, the cartridge C can be advantageously easily housed in the magazine housing space 155h.

(Another Example of Positioning Portion)

The positioning portion of the positioning mechanism such as the four shaft-like members 156 may not be necessarily fixed to the holding means 130, and may be move independently of the movement of the holding means 130.

In such a case, the positioning portion may be moved in a direction perpendicular to the direction of the central axis of the magazine housing space 155h without moving the bag holding mechanism 151, or both of the bag holding mechanism 151 and the positioning portion may be moved at the time of positioning the cartridge C.

(Another Example of Slit Plate 115)

Although the above slit plate 115 may be produced by forming the slit 115h in one plate-like member, the slit plate 115 may be formed by joining two plate-like members 116 and 117 so that end surfaces thereof come into surface contact with each other, as illustrated in FIG. 6.

As illustrated in FIG. 6, the plate-like member 116 is provided on the pair of holding surfaces 114b,114b of the left-and-right pair of side walls 114,114. The plate-like member 116 is formed so that an opposite end surface 116b is perpendicular to the reference inner surface 114a of the side wall 114, when the plate-like member 116 is positioned by a incised mark or the like.

On the other hand, the plate-like member 117 is provided on the pair of holding surfaces 114b,114b of the left-and-right pair of side walls 114,114 so that one end surface of the plate-like member 117 comes into surface contact with the opposite end surface 116b of the plate-like member 116. The plate-like member 117 is formed so that the end surface being in surface contact with the opposite end surface 116b of the plate-like member 116 (opposite end surface 117a) is flat and perpendicular to both surfaces of the plate-like members 116 and 117.

The opposite end surface 116b of the plate-like member 116 includes a concave portion 116c obtained by recessing the end surface. The concave portion 116c is formed so as to extend through both surfaces of the plate-like member 116.

Accordingly, when the opposite end surfaces 116b and 117a of the two plate-like members 116 and 117 are joined to each other and the plate-like member 116 is positioned and provided on the pair of holding surfaces 114b, 114b, the slit 115h extending through the slit plate 115 can be formed.

In the case of forming the slit plate 115 in such a manner, a very narrow slit 115h can be easily and correctly formed because a width of the slit 115h can be adjusted simply by adjusting a depth of the concave portion 116c formed in the opposite end surface 116b of the plate-like member 116.

Additionally, an axial direction of the slit 115h has to be maintained correctly perpendicular to the reference inner surface 114a of the side wall 114. In the case of forming the slit plate 115 in the above described manner, if the opposite end surface 116b of the plate-like member 116 is maintained parallel to a bottom surface of the concave portion 116c, the axial direction of the slit 115h can be maintained correctly perpendicular to the reference inner surface 114a of the side wall 114. Then, the slit 115h can be very simply and accurately formed, compared with the case where the slit 115h is formed in one plate as a through hole. For example, in the case where the slit plate 115 is formed by joining the opposite end surfaces 116b and 117a of the two plate-like members 116 and 117 to each other, the slit plate 115 can be accurately formed even if the width of the slit 115h is 0.1 to 0.01 mm.

In order to ensure the surface contact between the opposite end surfaces 116b and 117a of the two plate-like members 116 and 117, the two plate-like members 116 and 117 are preferably fixed to each other with a bolt or the like.

Note that various known positioning mechanisms can be employed as a method for correctly positioning the plate-like member 116. As described above, a method for aligning each of the plate-like members 116 and 117 based on an incised mark, or a method for positioning using a locating pin or performing a process for forming a step or the like can be employed.

Although the case where the recess is formed in the opposite end surface 116b of the plate-like member 116 has been described in the above example, a recess may be formed in the opposite end surface 117a of the plate-like member 117 to form the slit 115h without forming the recess in the opposite end surface 116b of the plate-like member 116. The slit 115h may also be formed by forming a recess in each of the opposite end surfaces 116b and 117a of the plate-like members 116 and 117.

Additionally, with a configuration of the slit plate 115 described below, a length of the slit 115h can be changed. This allows the length of the slit 115h to be adjusted according to the sources to be subjected to the radiation intensity measurement, allowing one slit plate 115 to measure, for example, a plurality of sources having different lengths. Therefore, another slit plate 115 need not to be prepared according to sources to be measured, thereby advantageously reducing components of the apparatus and performing slit adjustment easily at the time of changing the sources.

Hereinafter, a configuration of the slit plate 115 allowing the length of the slit 115h to be changed will be described.

Figure 13:
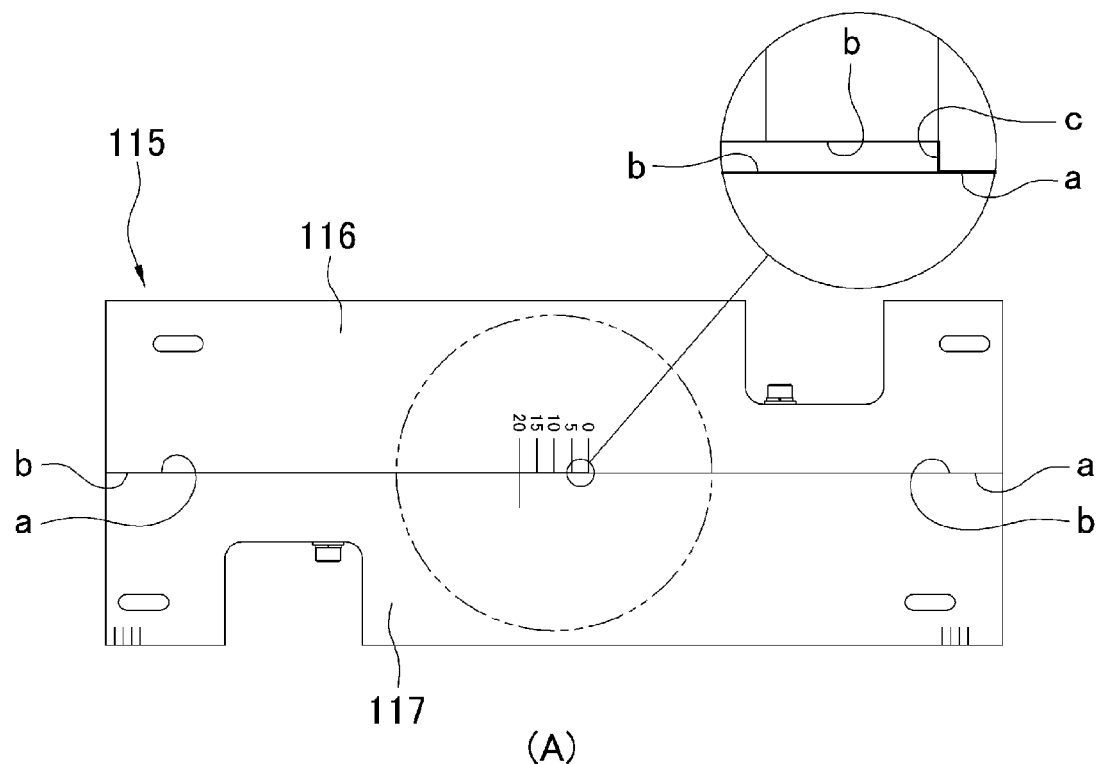
FIG. 13 illustrates schematic views of a slit plate 115 capable of adjusting a length of a slit 115h, and (A) is an explanatory view when the length of the slit 115h is adjusted to 20 mm and (B) is an explanatory view when the length of the slit 115h is adjusted to 10 mm.
Figure 13:
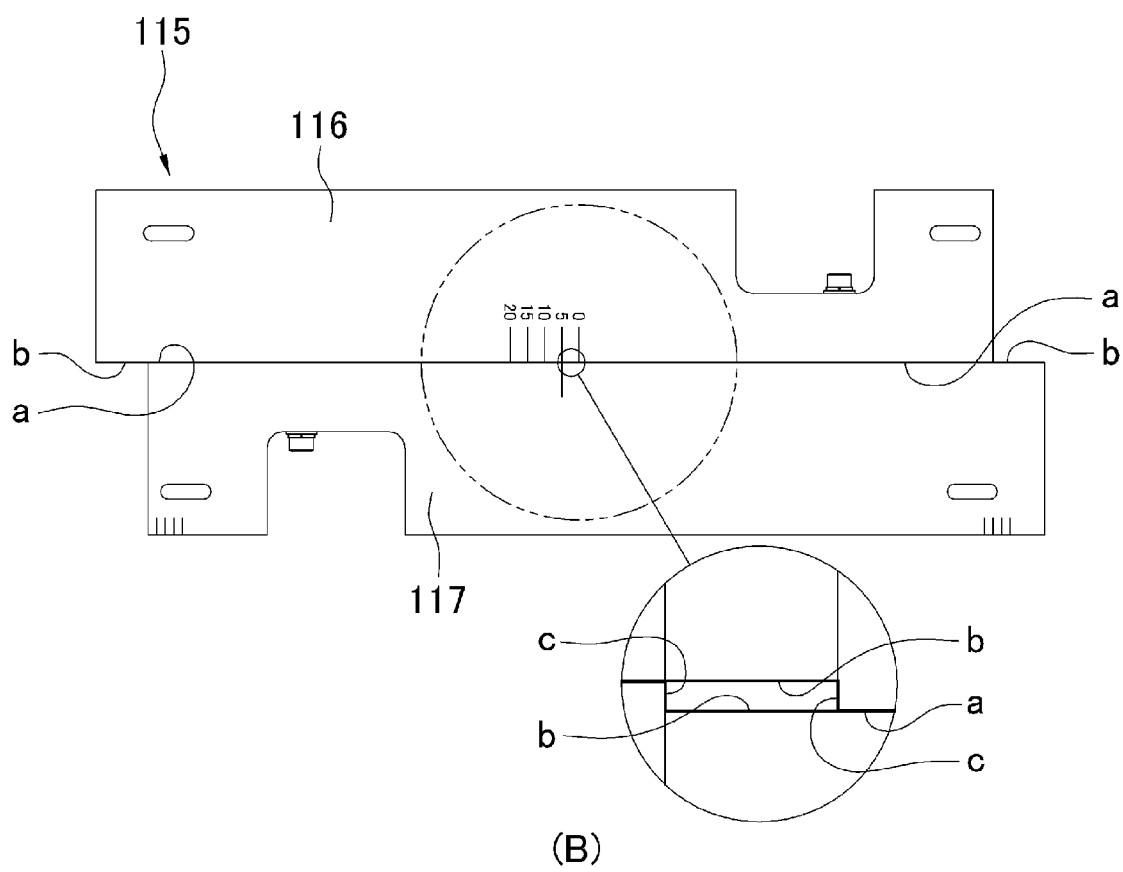
Figure 14:
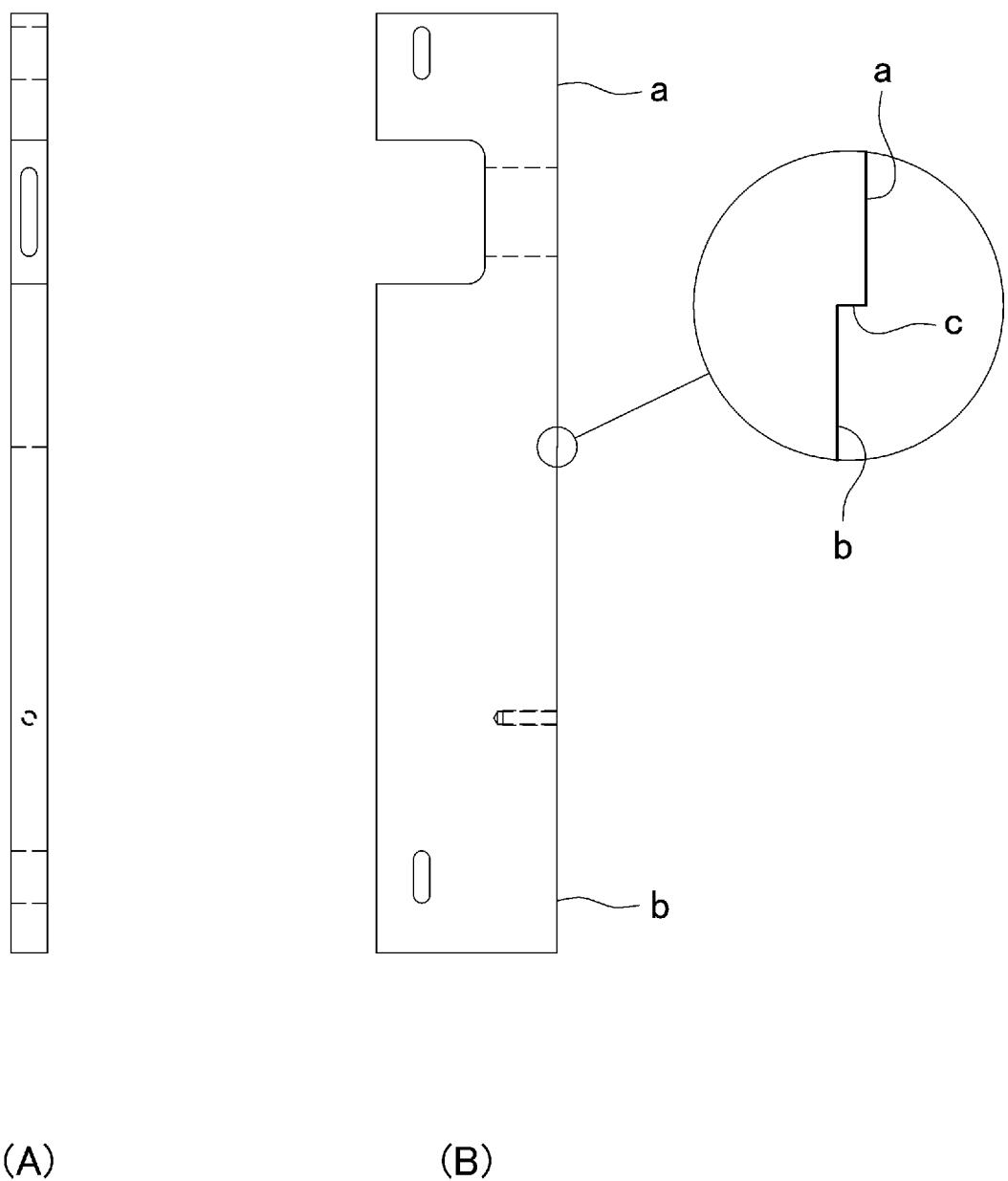
FIG. 14 illustrates explanatory views of plate-like members alone forming the slit plate 115 in FIG. 13.

As illustrated in FIGS. 13 and 14, the pair of plate-like members 116 and 117 in the slit plate 115 is formed into the same shape, and has the opposite end surface 116b and 117a formed into an end surface with a step, respectively.

Specifically, each of the opposite end surfaces 116b and 117a of the pair of plate-like members 116 and 117 has a reference surface a and a slide surface b provided to be parallel to the reference surface a and to be recessed (as an offset) by a width of the slit with respect to the reference surface a. A coupling surface c for coupling the slide surface b and the reference surface a is also formed therebetween.

In the opposite end surfaces 116b and 117a of the pair of plate-like members 116 and 117, each of the reference surfaces a, the slide surfaces b and the coupling surfaces c is formed so as to be perpendicular to both surfaces of the plate-like members 116 and 117.

According to the above configuration, when the slit plate 115 is formed so that the opposite end surfaces 116b and 117a of the pair of plate-like members 116 and 117 come into surface contact with each other, the slit 115h is formed between the pair of plate-like members 116 and 117.

That is, the slit plate 115 is formed by coupling the pair of plate-like members 116 and 117 so that the reference surface a on the opposite end surface in one of the plate-like members comes into surface contact with the slide surface b on the opposite end surface in the other plate-like member.

When the coupling surfaces c on the opposite end surfaces 116b and 117a of the pair of plate-like members 116 and 117 are apart from each other, the slit 115h can be formed between the slide surfaces b of the pair of plate-like members 116 and 117.

Since the reference surface a and the slide surface b are formed to be parallel to each other in each of the opposite end surfaces 116b and 117a of the plate-like members 116 and 117, a relative position of both of the pair of plate-like members 116 and 117 can be changed along the axial direction of the slit 115h with the reference surface a on the opposite end surface in one of the plate-like members being in surface contact with the slide surface b on the opposite end surface in the other plate-like member.

Accordingly, a length of the slit 115h can be changed because the coupling surfaces c can be apart from each other with a distance between the slide surfaces b of the pair of plate-like members 116 and 117 kept constant (that is, a width of the slit 115h is kept constant).

Thus, the slit plate 115 is formed with the pair of plate-like members 116 and 117 having the above shape, allowing one slit plate 115 to measure a plurality of sources having different lengths. Therefore, another slit plate 115 need not to be prepared according to sources to be measured, thereby advantageously reducing components of the apparatus and performing slit adjustment easily at the time of changing the sources.

A scale (for example, in 5 mm intervals) may be provided in the vicinity of the slide surface b along the slide surface b. The length of the slit 115h can therefore be grasped simply by checking the scale, thereby causing the length of the slit 115h to be easily adjusted.

The pair of plate-like members 116 and 117 corresponds to a pair of slit forming plates according to claims.

(Radiation Intensity Measuring Apparatus in Third Embodiment)

Figure 19:
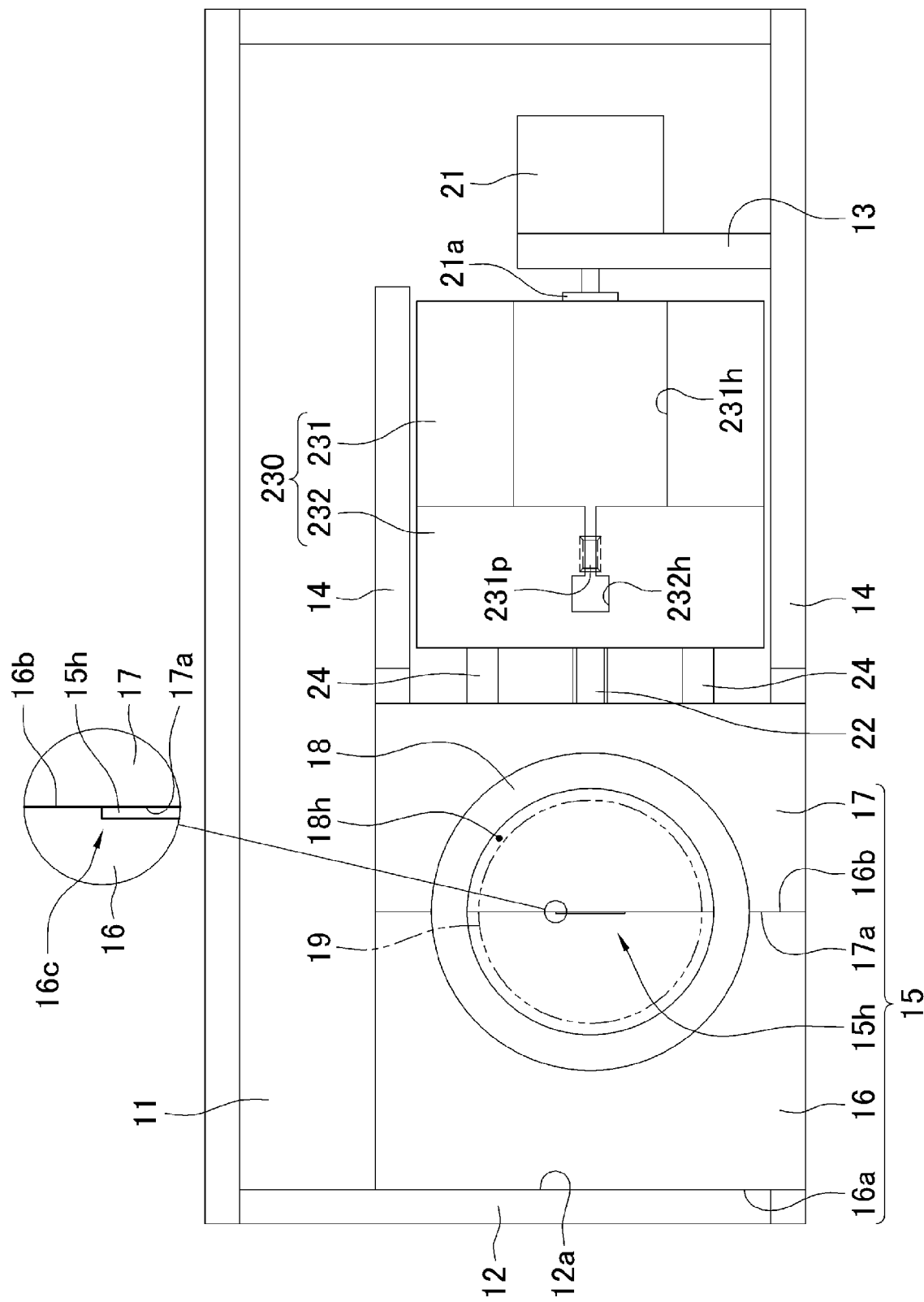
FIG. 19 is a schematic plan view illustrating a radiation intensity measuring apparatus 300 for an encapsulated sealed radioactive source for brachytherapy including the holding means 230 in a third embodiment.

As illustrated in FIG. 19, a radiation intensity measuring apparatus 300 for a encapsulated sealed radioactive source for brachytherapy in a third embodiment is the radiation intensity measuring apparatus 1 in the first embodiment having a difference in holding means for holding the cartridge C.

The radiation intensity measuring apparatus 300 in the third embodiment is substantially similar to the radiation intensity measuring apparatus in the first embodiment except the holding means. Hereinafter, only holding means 230 will therefore be described in detail.

In the radiation intensity measuring apparatus 300 in the third embodiment in FIG. 19, elements substantially the same as those of the radiation intensity measuring apparatus 1 in the first embodiment are represented by the same reference numerals as those of the radiation intensity measuring apparatus 1 in the first embodiment.

First, the radiation intensity measuring apparatus 300 in the third embodiment is for holding a cartridge C housed in a plastic case PK different from the radiation intensity measuring apparatus 1 in the first embodiment.

Then, the plastic case PK will be described before describing the holding means in the radiation intensity measuring apparatus 300 in the third embodiment.

Figure 16:
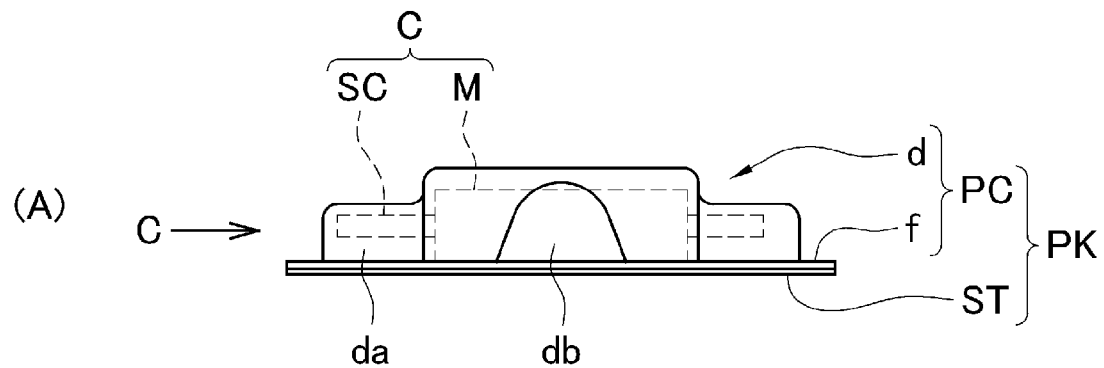
FIG. 16 illustrates schematic views of a plastic case PK housing the cartridge C; and (A) is a side view thereof, (B) is a plan view thereof, and (C) is a view on arrow C of (A).
Figure 16:
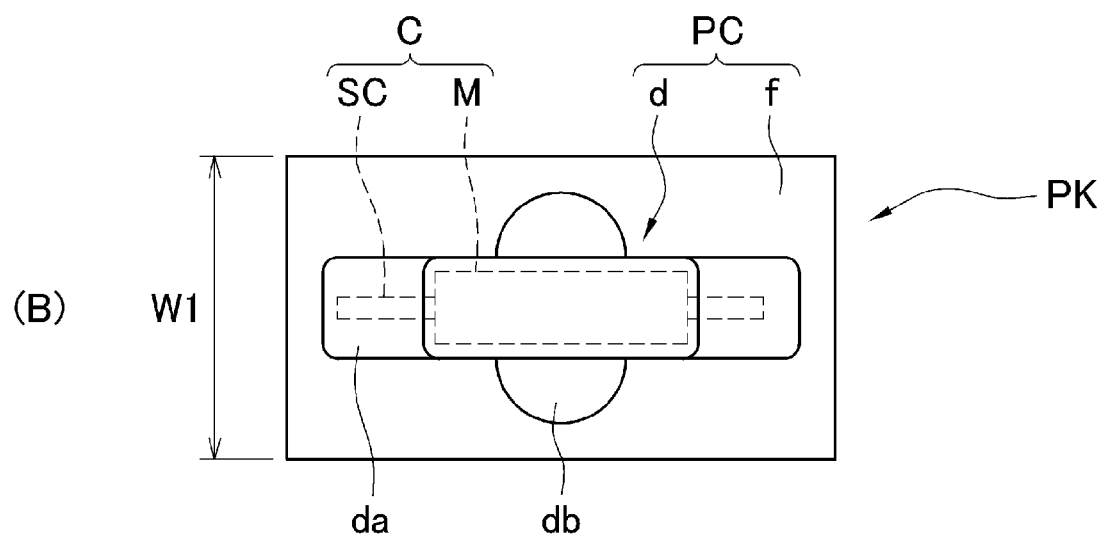
Figure 16:
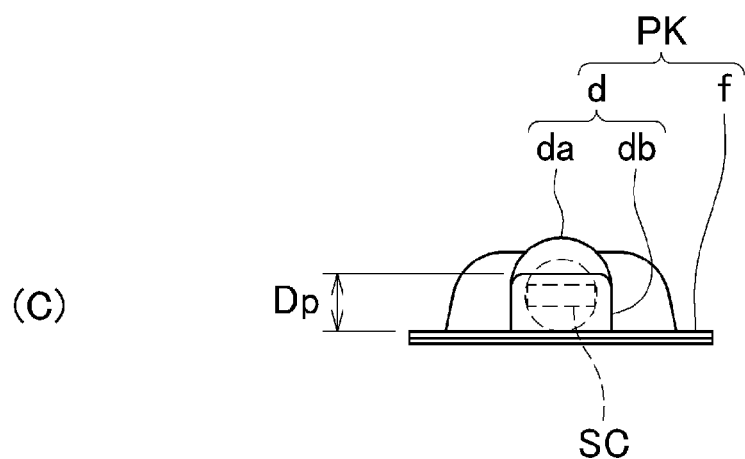

As illustrated in FIG. 16, the plastic case PK includes a housing case PC made of plastic and having a concave portion (hereinafter, referred to as a concave portion d) and a cover sheet ST for covering an aperture of the concave portion of the housing case PC.

As illustrated in FIG. 16, the housing case PC is a member made of a material having strength to some extent such as plastic. The housing case PC has the concave portion d having the cartridge C housed therein and a flange portion f provided around the aperture of the concave portion d.

The concave portion d is formed so that an axial direction of the cartridge C substantially corresponds to an axial direction of the concave portion d and movement of the cartridge C can be limited thereinside when housing the cartridge C.

Specifically, a magazine housing portion db capable of housing a magazine M of the cartridge C is provided in the central portion of the concave portion d. The magazine housing portion db is formed so that a depth and a width thereof are slightly larger than a diameter of the magazine M and a length thereof is slightly longer than that of the magazine M in an axial direction of the magazine M.

Moreover, the magazine housing portion db is formed into a shape allowing the magazine M to be held so that the axial direction of the magazine M housed thereinside substantially corresponds to an axial direction of the magazine housing portion db.

A seed cartridge housing portion da of space communicating with the magazine housing portion db is provided at an end of the magazine housing portion db in the axial direction. The seed cartridge housing portion da is formed so as to house a seed cartridge SC when the magazine M of the cartridge C is housed in the magazine housing portion db.

The seed cartridge housing portion da is formed so that an axial direction of the seed cartridge housing portion da becomes substantially perpendicular to an axial direction of a plurality of sources S in the seed cartridge SC, when the seed cartridge SC is housed in the seed cartridge housing portion da.

Additionally, in the seed cartridge housing portion da, a bottom surface of a concave portion thereof (a top surface in FIG. 16) is formed into a flat surface and a depth Dp thereof is formed to an extent that a radius of the magazine M and a thickness of the seed cartridge SC are added together.

A width of the seed cartridge housing portion da is slightly wider than that of the seed cartridge SC, more specifically, is wider than that of the seed cartridge SC by about a several millimeters.

The concave portion d also has a recess having a substantially similar shape to the seed cartridge housing portion da on an opposite side of the seed cartridge housing portion da with respect to the magazine housing portion db.

The flange portion f is provided around the aperture of the concave portion d so that surfaces thereof (a top surface and an under surface in FIG. 16) are parallel to the bottom surface of the seed cartridge housing portion da.

Since the concave portion d is formed into the above shape, the axial direction of the cartridge C substantially corresponds to the axial direction of the concave portion d when the cartridge C is housed in the concave portion d of the housing case PC. Moreover, the cartridge C is provided so that a surface of the seed cartridge SC is substantially parallel to the bottom surface of the seed cartridge housing portion da.

When the cover sheet ST is provided so as to cover the aperture of the concave portion d in such a state and the cover sheet ST and the flange portion f airtightly adhere to each other, the cartridge C can be tightly enclosed in the plastic case PK.

Further, when the cartridge C is housed in the concave portion d, movement of the cartridge C is limited in an axial direction thereof. This is because, when the cartridge C is about to move in the axial direction, an end surface of the magazine M in the axial direction comes into contact with a wall surface to which the magazine housing portion db, the seed cartridge housing portion da and the like are coupled. This prevents the cartridge C from being able to move.

Rotation about the axis of the cartridge C is also limited when the cover sheet ST is stuck on the flange portion f of the housing case PC. This is because the surface of the seed cartridge SC is in surface contact with the bottom surface of the seed cartridge housing portion da or only a little clearance lies therebetween.

Accordingly, the cartridge C housed in the plastic case PK is held so that the axial direction of the cartridge C substantially corresponds to the axial direction of the concave portion d as well as the surface of the seed cartridge SC is parallel to a surface of the flange portion f, in other words, the surface of the seed cartridge SC is substantially parallel to the bottom surface (under surface in FIG. 16) of the plastic case PK.

(Description of Holding Means 230)

The holding means 230 for holding the cartridge C housed in the above plastic case PK will now be described.

Figure 17:
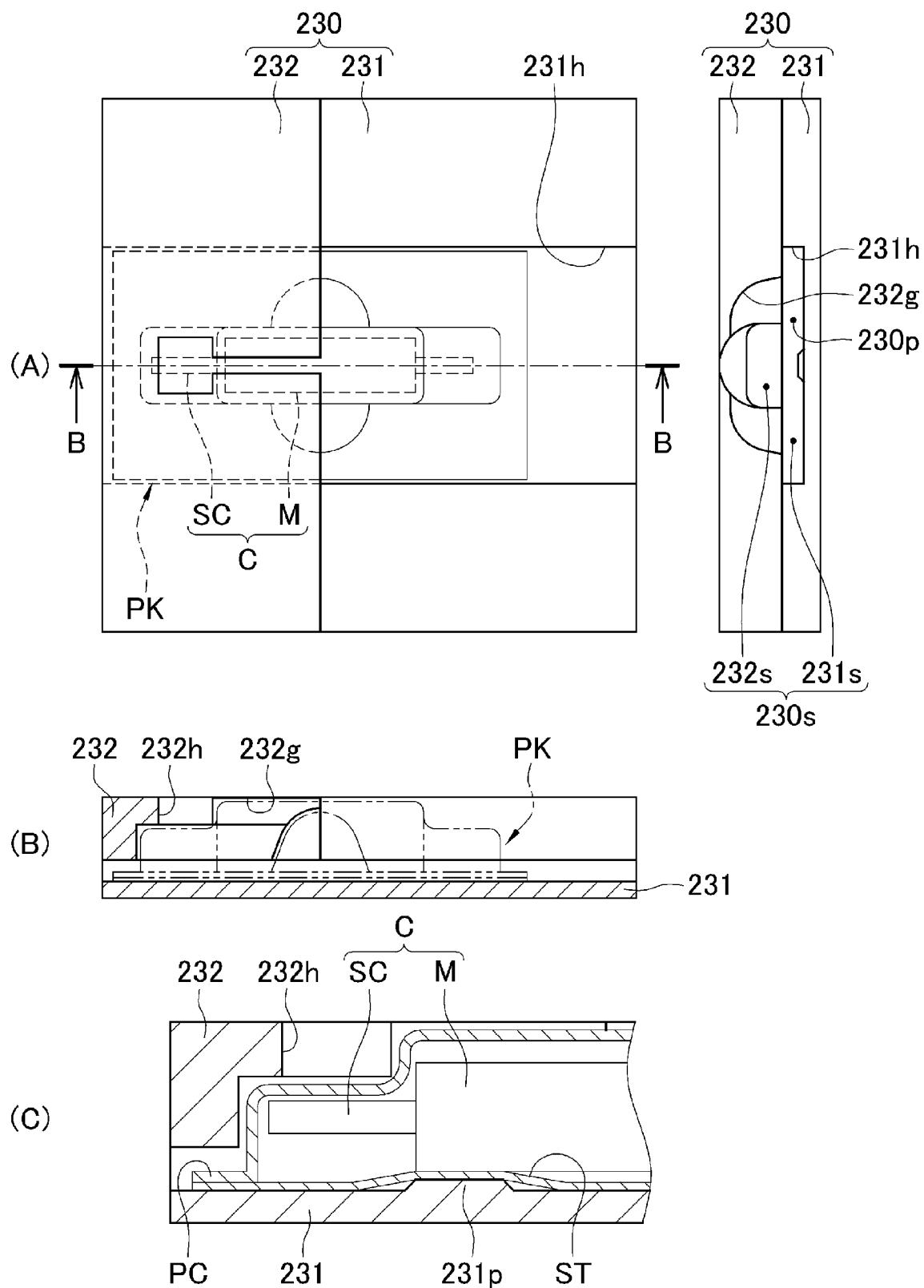
FIG. 17 illustrates schematic views of holding means 230 alone; and (A) is a plan view thereof, (B) is a cross sectional view taken along a B-B line of (A), and (C) is an enlarged cross sectional view of a principal part.
Figure 18:
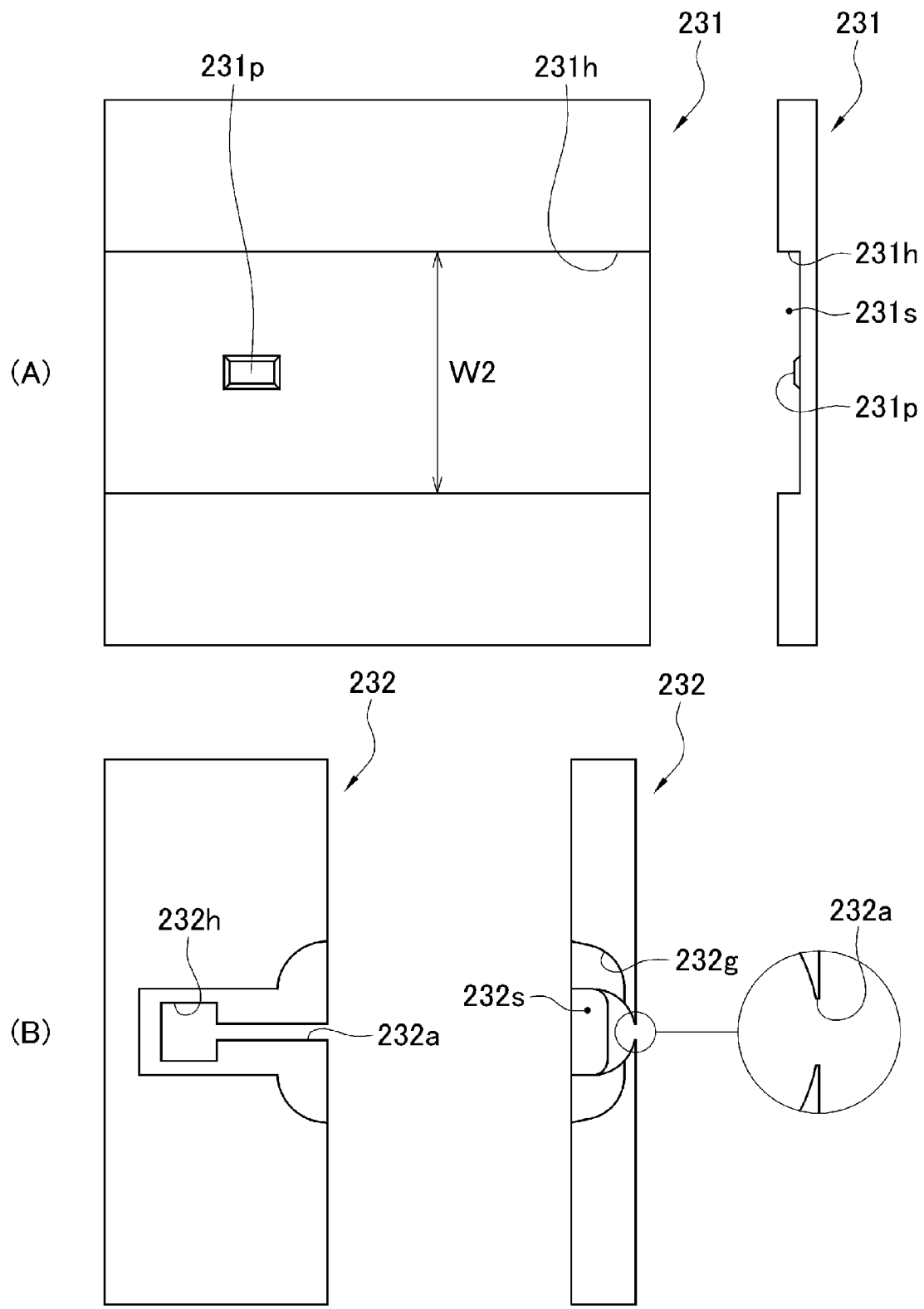
FIG. 18(A) is a schematic view of a holding base 231 alone in the holding means 230.
FIG. 18(B) is a schematic view of an upper cover 232 alone in the holding means 230

In FIGS. 17 and 18, reference numeral 231 indicates a plate-like holding base. The holding base 231 is a plate-like member having its top surface formed into a flat surface. The above nut member 23 and the above pair of sliding members 25,25 are coupled to an under surface of the holding base 231 and support the holding base 231. The holding base 231 is thus provided so that a top surface thereof becomes parallel to the top surface of the above base member 11.

A groove portion 231h obtained by recessing the top surface of the holding base 231 is formed in the top surface thereof. The groove portion 231h is for forming housing space 230s housing the plastic case PK with space 231s inside the groove portion 231h and space 232s in housing recess 232g of an upper cover 232 described later. The groove portion 231h is formed so that an axial direction thereof is parallel to an axial direction of the screw shaft 22 (see FIG. 19). That is, the groove portion 231h is formed so that the axial direction thereof is perpendicular to an axial direction of the slit 15h. The groove portion 231h is also formed so that an inner bottom surface thereof is formed into a flat surface parallel to the top surface of the holding base 231. A width W2 of the groove portion 231h is substantially the same as a width W1 of the plastic case PK (see FIG. 16(B)).

As illustrated in FIGS. 17 and 18, the plate-like upper cover 232 is provided above the holding base 231. The upper cover 232 is a plate-like member having its under surface formed into a flat surface.

The under surface of the upper cover 232 has the groove-shaped housing recess 232g obtained by recessing the under surface. The housing recess 232g is for forming the housing space 230s housing the plastic case PK with the space 232s inside the housing recess 232g and the space 231h inside the groove 231s, as described above. The groove-shaped housing recess 232g is formed so as to extend from an aperture on a farther side from the slit plate 15 (a right end in FIG. 17) toward the slit plate 15. Moreover, the housing recess 232g is formed so that an axial direction thereof is parallel to the axial direction of the screw shaft 22 (see FIG. 19), similarly to the groove portion 231h. That is, the housing recess 232g is also formed so that an axial direction thereof is perpendicular to the slit 15h.

The housing recess 232g is also formed so that a shape of an inner surface thereof is substantially the same as that of the top surface of the recess portion d of the housing case PC in the plastic case PK. Specifically, a tip portion of the housing recess 232g (a part on the left side in FIG. 17) has a recess having an inner surface with a shape substantially the same as that of the seed cartridge housing portion da, while a base end part thereof (a part on the right side in FIG. 17) has a recess having an inner surface with a shape substantially the same as that of the magazine housing portion db (see FIG. 17(B)).

"A shape substantially the same" here refers to a shape that the top surface of the plastic case PK comes into contact with the inner surface of the housing recess 232g, and further, force for slightly compressing the plastic case PK is applied when the plastic PK is pressed into the housing space 230s. Specifically, the housing recess 232g is formed so that a thickness of the seed cartridge housing portion da in the plastic case PK is slightly smaller than a distance from an inner surface of the tip portion in the housing recess 232g to the inner bottom surface of the groove portion 231h.

The housing recess 232g is formed so that a plane including an axial direction thereof and perpendicular to the top surface of the base member 11 divides the slit 15h into two equal parts. That is, the housing recess 232g is formed at a position where the housing recess 232g passes below the slit 15h when the moving means 20 causes the holding means 230 to move below the slit plate 15 in the housing space 10h.

In the upper cover 232, a through hole 232h extending through between the housing recess 232g and the outside is formed in the tip portion of the housing recess 232g, that is, the part forming into the same shape as the top surface of the seed cartridge housing portion da.

According to the above configuration, the plastic case PK can be fixed to the holding means 230 as follows.

The plastic case PK is first placed so that the bottom surface thereof comes into surface contact with the inner bottom surface of the groove portion 231h. The seed cartridge housing portion da is provided so as to be located on a side of the housing recess 232g at this time.

When the plastic case PK in such a state is moved toward the housing recess 232g with the bottom surface sliding along the inner bottom surface of the groove portion 231h, the plastic case PK can be inserted into the housing space 230s formed between the housing recess 232g and the groove portion 231h from a side of the seed cartridge housing portion da.

As the plastic case PK is inserted into the housing space 230s, the tip portion of the plastic case PK (that is, a position of the seed cartridge housing portion da in the plastic case PK) is soon provided between the inner surface of the tip portion in the housing recess 232g and the inner bottom surface of the groove portion 231h. This therefore enables to fix the plastic case PK to the holding means 230.

Then, the cartridge C in the plastic case PK can be provided in a predetermined posture, that is, so that the axial direction thereof is parallel to the axial direction of the screw shaft 22 (see FIG. 19). In other words, the cartridge C can be provided so that the axial direction of the plurality of sources S loaded in the seed cartridge SC is parallel to the axial direction of the slit 15h.

As described above, the radiation intensity measuring apparatus 300 in the third embodiment allows the cartridge C loaded with the plurality of sources S to be mounted on the holding means 230 with the cartridge C housed in the plastic case PK.

The housing recess 232g is formed so that the plane including the axial direction thereof and perpendicular to the top surface of the base member 11 divides the slit 15h into two equal parts. The through hole 232h extending through between the housing recess 232g and the outside is formed in the upper cover 232.

Accordingly, the movement of the holding means 230 allows the plurality of sources S to pass below the slit 15h, and therefore, intensity of radiations of each source S passing through the through hole 232h and the slit 15h can be measured.

(Description of Projection 231p)

A projection 231p may also be formed on the inner bottom surface of the groove portion 231h. Specifically, the projection 231p may be formed in a part of an inner surface of the groove portion 231h at a boundary part between the tip portion and the base end portion of the housing recess 232g or a part of an inner surface of the tip in the base end portion of the housing recess 232g, as well as in the middle of a width direction of the groove portion 231h (a vertical direction in FIG. 17(A)).

Although the cover sheet ST is mounted on the plastic case PK, the cover sheet ST can be slightly changed in shape at a part covering the aperture of the recess portion d. Accordingly, providing the projection 231p at the above position causes the cover sheet ST to be pressed upward by the projection 231p when the plastic case PK is pressed into the housing space 230s. In other words, the cover sheet ST is pressed by the projection 231p so as to be recessed in the recess portion d, resulting in being changed in shape.

When the cover sheet ST is recessed inside, the magazine M of the cartridge C is pressed upward, thereby the top surface of the seed cartridge SC being pressed against the inner bottom surface of the seed cartridge housing portion da. In other words, the top surface of the seed cartridge SC is pressed against an inner surface of the upper cover 232.

(Another Shape of Projection 231p)

Figure 20:
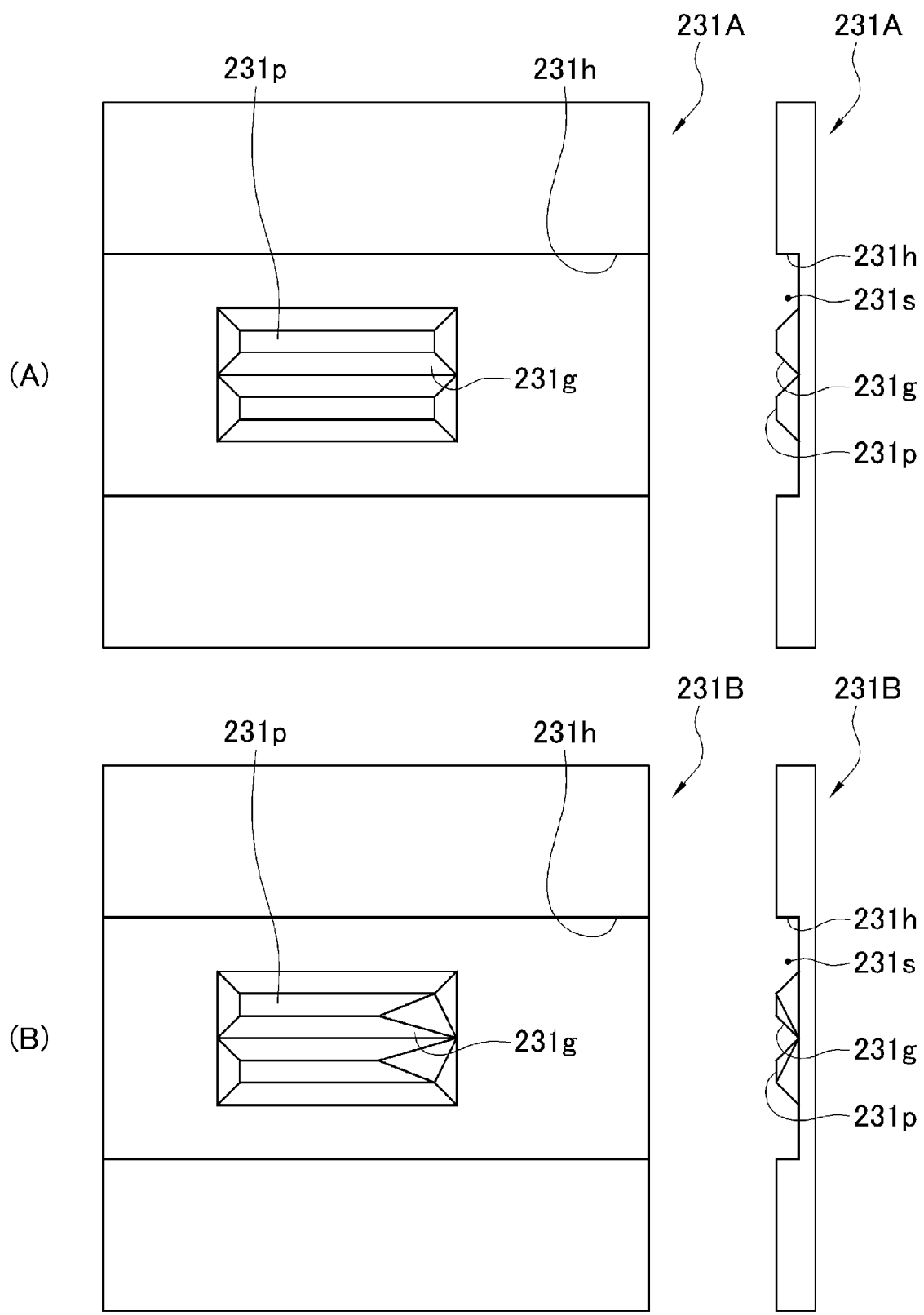
FIG. 20(A) is a schematic view of another holding base 231A alone in the holding means 230.
FIG. 20(B) is a schematic view of another holding base 231B alone in the holding means 230.

The shape of the projection 231p formed on the holding base 231 is not limited to the above, and shapes illustrated in FIGS. 20 and 21 may be employed.

Each of projections 231p formed on holding bases 231A to D in FIGS. 20 and 21 has a longer length in an axial direction thereof, compared with the projection 231p on the holding base 231. Specifically, each of the projections 231p formed on the holding bases 231A to D is formed so that the length in the axial direction is as long as the length of the magazine M of the cartridge C.

Each of the projections 231p formed on the holding bases 231A to D is formed so that a tip thereof (left end in FIG. 20 or 21) is located at a position where the tip portion of the magazine M is provided when the plastic case PK is pressed into the housing space 230s.

Moreover, the projection 231p is formed so that a top surface thereof (or a top end) is parallel to the inner bottom surface of the groove portion 231h. In other words, the projection 231p is formed so that the top surface thereof is parallel to the top surface of the holding base 231.

If the projection 231p is formed into the above shape, the cartridge C in the plastic case PK is provided in a state of being placed on the top surface of the projection 231p via the cover sheet ST when the plastic case PK is pressed into the housing space 230s. Since the top surface of the projection 231p is formed so as to be parallel to the inner bottom surface of the groove portion 231h, the cartridge C can be provided so that the axial direction is parallel to the inner bottom surface of the groove portion 231h.

Moreover, the cartridge C can be pressed up toward the housing case PC by a height of the projection 231p, thereby allowing the top surface of the seed cartridge SC to be pressed against the inner bottom surface of the seed cartridge housing portion da.

Accordingly, the cartridge C can be fixed to the holding means 230 so that the axial direction of the plurality of sources S loaded in the seed cartridge SC is parallel to the axial direction of the slit 15h.

Preferably, a groove portion 231g obtained by recessing the top surface of the projection 231p and extending along the axial direction of the groove portion 231h is formed in the top surface of the projection 231p. With such a groove portion 231g, the axial direction of the magazine M of the cartridge C can be maintained parallel to a direction of the movement of the holding means 230 by the groove portion 231g when the plastic case PK is pressed into the housing space 230s. Therefore, the cartridge C can be certainly fixed by the holding means 230 so that the axial direction of the plurality of sources S loaded in the seed cartridge SC is parallel to the axial direction of the slit 15h.

Additionally, an inclined plane inclined upward from the inner bottom surface of the groove portion 231h toward the top surface of the projection 231p may be formed at the base end of the projection 231p (right end in FIG. 20 or 21), similarly to the projections 231p formed on the holding bases 231B and D. With such an inclined surface of the projection 231p, advantageously, the cartridge C can be smoothly moved to the top surface of the projection 231p when the plastic case PK is pressed into the housing space 230s.

INDUSTRIAL APPLICABILITY

The radiation intensity measuring apparatus for an encapsulated sealed radioactive source for brachytherapy according to the present invention is suitable for measuring radiation intensity of an encapsulated sealed radioactive source used for brachytherapy for prostate cancer.

REFERENCE SIGNS LIST 1 radiation intensity measuring apparatus
10h housing space
15 slit plate
15h slit
16 plate-like member
17 plate-like member
18 radiation-blocking member
18h measuring apparatus housing portion
19 measuring apparatus
20 moving means
30 holding means
30h clearance
33 holding hole
34 magazine holding region
35 tip holding region
36 fixed groove
36a bottom surface
36b end surface
37 coupling region
37a inclined plane
100 radiation intensity measuring apparatus
110h housing space
115 slit plate
115h slit
116 plate-like member
117 plate-like member
118 radiation-blocking member
118h measuring apparatus housing portion
119 measuring apparatus
120 moving means
130 holding means
130h clearance
135 tip holding region
150 supplying means
151 bag holding mechanism
152 bag holding portion
156 shaft-like member
155h magazine housing space
C cartridge
SC seed cartridge
M magazine
B bag

The invention claimed is:

1. A radiation intensity measuring apparatus for an encapsulated sealed radioactive source for brachytherapy adapted to measure radiation intensity of sources loaded in a cartridge, comprising:
　　radiation intensity measuring means for measuring radiations emitted from the sources;
　　holding means for holding the cartridge; and
　　moving means for moving the holding means to the radiation intensity measuring means, wherein
　　the radiation intensity measuring means comprises:
　　　　a housing space in which the cartridge held by the holding means is brought; and
　　　　a housing portion provided with a slit communicating between the housing space and an outside,
　　the slit provided on the housing portion is formed so that a width thereof is narrower than a diameter of the sources,
　　the holding means comprises:

a holding mechanism for holding the cartridge so that an axial direction of the sources loaded in the cartridge is parallel to an axial direction of the slit, and the moving means comprises:
a guide portion for guiding a movement of the holding means so that the holding means moves along a direction perpendicular to the axial direction of the slit; and
a moving portion for moving the holding means so that the sources loaded in the cartridge pass through a position of the slit in the housing space of the housing portion.

2. The radiation intensity measuring apparatus for an encapsulated sealed radioactive source for brachytherapy according to claim 1, wherein the cartridge comprises:
a substantially cylindrical magazine; and
a seed cartridge provided on a tip of the magazine and having a plate shape with a thickness thinner than a diameter of the magazine, the seed cartridge can be loaded with the sources thereinside so that a surface of the seed cartridge is parallel to the axial direction of the sources, the holding means holds the cartridge tightly enclosed in a bag, the holding mechanism comprises:
a clearance extending along a moving direction of the holding means and having a height narrower than the thickness of the seed cartridge, the clearance is provided with a tip holding region of space communicating with one aperture of the clearance, a fixed groove obtained by recessing a surface having the clearance formed is formed in the tip holding region, and the fixed groove is formed so that a tip surface thereof is parallel to the axial direction of the slit and a distance from a bottom surface of the fixed groove to the other surface having the clearance formed is smaller than a thickness obtained by adding a thickness of the bag including the cartridge and the thickness of the seed cartridge to an extent that a tip portion of the seed cartridge can be inserted into the tip holding region.

3. The radiation intensity measuring apparatus for an encapsulated sealed radioactive source for brachytherapy according to claim 2, wherein a coupling region of space coupling between an end of the one aperture and the tip holding region is formed at the clearance, and an inclined plane coupling between the bottom surface of the fixed groove and the end of the one aperture is formed in the coupling region.

4. The radiation intensity measuring apparatus for an encapsulated sealed radioactive source for brachytherapy according to claim 2, wherein a width of the clearance is formed so as to be wider than a width of the bag, and the clearance comprises:
a magazine holding region provided between one aperture of the clearance and the tip holding region, the magazine holding region being space communicating with the tip holding region formed by recessing both surfaces of the clearance and substantially cylindrical space for housing the magazine.

5. The radiation intensity measuring apparatus for an encapsulated sealed radioactive source for brachytherapy according to claim 4, wherein a coupling region of space coupling between the tip holding region and the magazine holding region is formed at the clearance, and an inclined plane coupling between the bottom surface of the fixed groove and a concave surface of the magazine holding region is formed in the coupling region.

6. The radiation intensity measuring apparatus for an encapsulated sealed radioactive source for brachytherapy according to claim 1, further comprising supplying means for supplying the cartridge enclosed in a bag to the holding means, wherein the sources are loaded in the cartridge so that the axial direction is perpendicular to an axial direction of the magazine in the cartridge, the supplying means comprises:
a bag holding mechanism for holding the bag including the cartridge;
a positioning mechanism provided between the bag holding mechanism and the holding mechanism, the positioning mechanism moving relatively close to and apart from the bag holding mechanism in a direction of a reference axis coaxial with a central axis of the magazine in the cartridge held by the holding means; and
a cartridge supplying mechanism for supplying the cartridge positioned by a positioning portion of the positioning mechanism to the holding means, and the positioning mechanism comprises:
the positioning portion for positioning the cartridge so that the positioning portion approaches the cartridge enclosed in the bag held by the bag holding mechanism and the central axis of the magazine of the cartridge becomes coaxial with the reference axis.

7. The radiation intensity measuring apparatus for an encapsulated sealed radioactive source for brachytherapy according to claim 6, wherein the bag holding mechanism comprises:
a pair of bag holding portions provided at positions sandwiching an perpendicular plane with respect to the axial direction of the slit, the pair of bag holding portions are provided so as to hold the bag in the vicinity of a central plane including the reference axis and perpendicular to the perpendicular plane, the positioning portion of the positioning mechanism comprises:
a pair of positioning members provided so as to sandwich the central plane, magazine housing space is formed between the pair of positioning members, the magazine housing space housing the magazine of the cartridge so as to be positioned when the positioning mechanism approaches the bag holding mechanism, the magazine housing space is formed so that a central axis thereof is coaxial with the reference axis, and opposite surfaces of the magazine housing space in the pair of positioning members are formed in a shape allowing a posture of the cartridge to change so that the central axis of the magazine in the cartridge becomes coaxial with the reference axis when the magazine of the cartridge is housed in the magazine housing space.

8. The radiation intensity measuring apparatus for an encapsulated sealed radioactive source for brachytherapy according to claim 7, wherein one of the pair of positioning members comprises:
a pair of shaft-like members whose axial direction is parallel to the reference axis, the other positioning member comprises:
a supporting member provided so as to sandwich the central plane with the pair of shaft-like members and form the magazine housing space between the supporting member and the pair of shaft-like members,
the positioning mechanism comprises:
a shaft-like member moving portion causing the pair of shaft-like members to move close to and apart from the bag holding mechanism along a direction of the reference axis,
the pair of shaft-like members are provided so that a distance between the pair of the shaft-like members and/or a distance between the pair of the shaft-like members and the supporting member is shorter than a diameter of the magazine in the cartridge, and
a distance from the reference axis becomes longer as getting close to a tip of a tip portion of each shaft-like member.

9. The radiation intensity measuring apparatus for an encapsulated sealed radioactive source for brachytherapy according to claim 8, wherein
the supporting member comprises:
a pair of shaft-like portions parallel to the pair of shaft-like members and provided so as to form the magazine housing space between the pair of shaft-like members and the pair of shaft-like portions, and
the pair of shaft-like portions are provided so that a distance between the pair of shaft-like portions is shorter than the diameter of the magazine in the cartridge and a distance between one of the shaft-like members and one of the shaft-like portions located on a diagonal line in the magazine housing space is slightly longer than the diameter of the magazine in the cartridge.

10. The radiation intensity measuring apparatus for an encapsulated sealed radioactive source for brachytherapy according to claim 6, wherein
the positioning mechanism comprises:
a position changing portion for changing a relative position between the positioning portion and the bag holding mechanism along a direction perpendicular to the perpendicular plane and parallel to the central plane.

11. The radiation intensity measuring apparatus for an encapsulated sealed radioactive source for brachytherapy according to claim 10, wherein
the position changing portion causes the bag holding mechanism to move back and forth.

12. The radiation intensity measuring apparatus for an encapsulated sealed radioactive source for brachytherapy according to claim 6, wherein
the positioning portion is provided on the holding means.

13. The radiation intensity measuring apparatus for an encapsulated sealed radioactive source for brachytherapy according to claim 1, wherein
the housing portion of the radiation intensity measuring means comprises:
a slit plate provided with a slit communicating between the housing space and an outside and having a pair of slit forming plates,
one end surface of each of the slit forming plates is provided with a reference surface, a slide surface parallel to the reference surface and offset with respect to the reference surface by a width of the slit, and a coupling surface for coupling the slide surface and the reference surface, and
the slit plate is formed by coupling the reference surface of one the pair of slit forming plates to the slide surface of the other slit forming plate so as to come into surface contact with each other.

14. The radiation intensity measuring apparatus for an encapsulated sealed radioactive source for brachytherapy according to claim 1, wherein
the housing portion of the radiation intensity measuring means comprises:
a slit plate having the slit formed; and
a body portion having the slit plate fixed thereto,
the slit plate is formed by joining two plate-like members with end surfaces thereof coming into surface contact with each other, and
a concave portion is provided on the end surface coming into surface contact with the other plate-like member of the plate-like members, the concave portion forming the slit obtained by recessing the end surface.

15. The radiation intensity measuring apparatus for an encapsulated sealed radioactive source for brachytherapy according to claim 1, wherein
the radiation intensity measuring means comprises:
a radiation-blocking member provided so as to surround a periphery of the slit, and
the radiation-blocking member comprises:
a measuring apparatus housing portion having the measuring apparatus provided therein.

16. An apparatus for measuring radiation intensity of at least one source loaded in a cartridge, comprising:
a radiation intensity measuring device for measuring radiation emitted from the source;
a holding device for holding the cartridge; and
a moving mechanism for moving the holding device to the radiation intensity measuring device, wherein
the radiation intensity measuring device comprises:
a housing space in which the cartridge held by the holding device is brought; and
a housing portion provided with a slit communicating between the housing space and an outside,
the slit provided on the housing portion is formed so that a width thereof is narrower than a diameter of the sources,
the holding device comprises:
a holding mechanism for holding the cartridge so that an axial direction of the sources loaded in the cartridge is parallel to an axial direction of the slit, and
the moving mechanism comprises:
a guide portion for guiding a movement of the holding device so that the holding device moves along a direction perpendicular to the axial direction of the slit; and
a moving portion for moving the holding device so that the sources loaded in the cartridge pass through a position of the slit in the housing space of the housing portion.

17. The apparatus of claim 16, wherein
the cartridge comprises:
a substantially cylindrical magazine; and
a seed cartridge provided on a tip of the magazine and having a plate shape with a thickness thinner than a diameter of the magazine,
the seed cartridge can be loaded with the sources thereinside so that a surface of the seed cartridge is parallel to the axial direction of the sources,
the holding device holds the cartridge tightly enclosed in a bag,
the holding mechanism comprises:
a clearance extending along a moving direction of the holding device and having a height narrower than the thickness of the seed cartridge,
the clearance is provided with a tip holding region of space communicating with one aperture of the clearance, a fixed groove obtained by recessing a surface having the clearance formed is formed in the tip holding region, and the fixed groove is formed so that a tip surface thereof is parallel to the axial direction of the slit and a distance from a bottom surface of the fixed groove to the other surface having the clearance formed is smaller than a thickness obtained by adding a thickness of the bag including the cartridge and the thickness of the seed cartridge to an extent that a tip portion of the seed cartridge can be inserted into the tip holding region.

18. The apparatus of claim 17, wherein a coupling region of space coupling between an end of the one aperture and the tip holding region is formed at the clearance, and an inclined plane coupling between the bottom surface of the fixed groove and the end of the one aperture is formed in the coupling region.

19. The apparatus of claim 17, wherein a width of the clearance is formed so as to be wider than a width of the bag, and the clearance comprises:
 a magazine holding region provided between one aperture of the clearance and the tip holding region, the magazine holding region being space communicating with the tip holding region formed by recessing both surfaces of the clearance and substantially cylindrical space for housing the magazine.

20. The apparatus of claim 19, wherein a coupling region of space coupling between the tip holding region and the magazine holding region is formed at the clearance, and an inclined plane coupling between the bottom surface of the fixed groove and a concave surface of the magazine holding region is formed in the coupling region.

21. The apparatus of claim 16, further comprising a supplying device for supplying the cartridge enclosed in a bag to the holding device, wherein the sources are loaded in the cartridge so that the axial direction is perpendicular to an axial direction of the magazine in the cartridge, the supplying device comprises:
 a bag holding mechanism for holding the bag including the cartridge;
 a positioning mechanism provided between the bag holding mechanism and the holding mechanism, the positioning mechanism moving relatively close to and apart from the bag holding mechanism in a direction of a reference axis coaxial with a central axis of the magazine in the cartridge held by the holding device; and
 a cartridge supplying mechanism for supplying the cartridge positioned by a positioning portion of the positioning mechanism to the holding device, and the positioning mechanism comprises:
 the positioning portion for positioning the cartridge so that the positioning portion approaches the cartridge enclosed in the bag held by the bag holding mechanism and the central axis of the magazine of the cartridge becomes coaxial with the reference axis.

22. The apparatus of claim 21, wherein the bag holding mechanism comprises:
 a pair of bag holding portions provided at positions sandwiching an perpendicular plane with respect to the axial direction of the slit, the pair of bag holding portions are provided so as to hold the bag in the vicinity of a central plane including the reference axis and perpendicular to the perpendicular plane, the positioning portion of the positioning mechanism comprises:
 a pair of positioning members provided so as to sandwich the central plane, magazine housing space is formed between the pair of positioning members, the magazine housing space housing the magazine of the cartridge so as to be positioned when the positioning mechanism approaches the bag holding mechanism, the magazine housing space is formed so that a central axis thereof is coaxial with the reference axis, and opposite surfaces of the magazine housing space in the pair of positioning members are formed in a shape allowing a posture of the cartridge to change so that the central axis of the magazine in the cartridge becomes coaxial with the reference axis when the magazine of the cartridge is housed in the magazine housing space.

23. The apparatus of claim 22, wherein one of the pair of positioning members comprises:
 a pair of shaft-like members whose axial direction is parallel to the reference axis, the other positioning member comprises:
 a supporting member provided so as to sandwich the central plane with the pair of shaft-like members and form the magazine housing space between the supporting member and the pair of shaft-like members, the positioning mechanism comprises:
 a shaft-like member moving portion causing the pair of shaft-like members to move close to and apart from the bag holding mechanism along a direction of the reference axis, the pair of shaft-like members are provided so that a distance between the pair of the shaft-like members and/or a distance between the pair of the shaft-like members and the supporting member is shorter than a diameter of the magazine in the cartridge, and a distance from the reference axis becomes longer as getting close to a tip of a tip portion of each shaft-like member.

24. The apparatus of claim 23, wherein the supporting member comprises:
 a pair of shaft-like portions parallel to the pair of shaft-like members and provided so as to form the magazine housing space between the pair of shaft-like members and the pair of shaft-like portions, and the pair of shaft-like portions are provided so that a distance between the pair of shaft-like portions is shorter than the diameter of the magazine in the cartridge and a distance between one of the shaft-like members and one of the shaft-like portions located on a diagonal line in the magazine housing space is slightly longer than the diameter of the magazine in the cartridge.

25. The apparatus of claim 21, wherein the positioning mechanism comprises:
 a position changing portion for changing a relative position between the positioning portion and the bag holding mechanism along a direction perpendicular to the perpendicular plane and parallel to the central plane.

26. The apparatus of claim 25, wherein the position changing portion causes the bag holding mechanism to move back and forth.

27. The apparatus of claim 21, wherein
the positioning portion is provided on the holding device.

28. The apparatus of claim 16, wherein
the housing portion of the radiation intensity measuring device comprises:
  a slit plate provided with a slit communicating between the housing space and an outside and having a pair of slit forming plates,
one end surface of each of the slit forming plates is provided with a reference surface, a slide surface parallel to the reference surface and offset with respect to the reference surface by a width of the slit, and a coupling surface for coupling the slide surface and the reference surface, and
the slit plate is formed by coupling the reference surface of one the pair of slit forming plates to the slide surface of the other slit forming plate so as to come into surface contact with each other.

29. The apparatus of claim 16, wherein
the housing portion of the radiation intensity measuring device comprises:
  a slit plate having the slit formed; and
  a body portion having the slit plate fixed thereto,
the slit plate is formed by joining two plate-like members with end surfaces thereof coming into surface contact with each other, and
a concave portion is provided on the end surface coming into surface contact with the other plate-like member of the plate-like members, the concave portion forming the slit obtained by recessing the end surface.

30. The apparatus of claim 16, wherein
the radiation intensity measuring device comprises:
  a radiation-blocking member provided so as to surround a periphery of the slit, and
the radiation-blocking member comprises:
  a measuring apparatus housing portion having the measuring apparatus provided therein.

* * * * *